United States Patent
Sato et al.

(10) Patent No.: US 11,447,569 B2
(45) Date of Patent: Sep. 20, 2022

(54) ANTI-PAD4 ANTIBODY

(71) Applicants: PUBLIC UNIVERSITY CORPORATION YOKOHAMA CITY UNIVERSITY, Yokohama (JP); PUBLIC UNIVERSITY CORPORATION NAGOYA CITY UNIVERSITY, Nagoya (JP); PHARMA FOODS INTERNATIONAL CO., LTD., Kyoto (JP)

(72) Inventors: Mamoru Sato, Yokohama (JP); Michiyuki Yamada, Yokohama (JP); Satoshi Kanazawa, Nagoya (JP); Masayoshi Toyoura, Kyoto (JP); Yuji Shoya, Kyoto (JP); Kenji Saito, Kyoto (JP); Chihiro Yamazaki, Kyoto (JP)

(73) Assignees: PUBLIC UNIVERSITY CORPORATION YOKOHAMA CITY UNIVERSITY, Yokohama (JP); PUBLIC UNIVERSITY CORPORATION NAGOYA CITY UNIVERSITY, Nagoya (JP); PHARMA FOODS INTERNATIONAL CO., LTD., Kyoto (JP)

( * ) Notice: Subject to any disclaimer, the term of this patent is extended or adjusted under 35 U.S.C. 154(b) by 0 days.

(21) Appl. No.: 15/555,808

(22) PCT Filed: Mar. 7, 2016

(86) PCT No.: PCT/JP2016/057030
§ 371 (c)(1),
(2) Date: Sep. 5, 2017

(87) PCT Pub. No.: WO2016/143753
PCT Pub. Date: Sep. 15, 2016

(65) Prior Publication Data
US 2018/0044434 A1 Feb. 15, 2018

(30) Foreign Application Priority Data

Mar. 6, 2015 (JP) .............................. JP2015-044518

(51) Int. Cl.
| | |
|---|---|
| *A61K 39/395* | (2006.01) |
| *C07K 16/40* | (2006.01) |
| *C12N 15/63* | (2006.01) |
| *C12N 9/99* | (2006.01) |
| *C12N 15/09* | (2006.01) |
| *A61K 39/00* | (2006.01) |

(52) U.S. Cl.
CPC ............ *C07K 16/40* (2013.01); *A61K 39/395* (2013.01); *A61K 39/3955* (2013.01); *C12N 9/99* (2013.01); *C12N 15/09* (2013.01); *C12N 15/63* (2013.01); *C12Y 305/03015* (2013.01); *A61K 2039/505* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/622* (2013.01); *C07K 2317/76* (2013.01); *C07K 2317/92* (2013.01)

(58) Field of Classification Search
CPC .. A61K 39/3955; A61K 39/395; A61K 38/43; C07K 16/18; C07K 16/40; C12N 9/00; C12N 9/99; C12Y 305/03015
See application file for complete search history.

(56) References Cited

U.S. PATENT DOCUMENTS

| | | | | |
|---|---|---|---|---|
| 2013/0101611 | A1* | 4/2013 | Andrade | C12N 9/78 424/185.1 |
| 2015/0153356 | A1 | 6/2015 | Meng et al. | |

FOREIGN PATENT DOCUMENTS

| | | |
|---|---|---|
| JP | 2009-156615 A | 7/2009 |
| WO | WO-2012/026309 A1 | 3/2012 |
| WO | WO-2013/143026 A1 | 10/2013 |
| WO | WO-2016155745 A1 * | 10/2016 |

OTHER PUBLICATIONS

Abcam datasheet for anti-PAD4 antibody "ab96758"; downloaded Jul. 15, 2019; 3 total pages.*
Kolodziej et al. PADI4 acts as a coactivator of Tal1 by counteracting repressive histone arginine methylation. Nature Comm 5: 3995, 2014.*
Lloyd et al. Modelling the human immune response: performance of a 10x11 human antibody repertoire against a broad panel of therapeutically relevant antigens. Protein Engineer Design Sei 22(3): 159-168, 2009.*
Sato et al. English language translation of WO 2012/026309, Jul. 12, 2019.*

(Continued)

*Primary Examiner* — Bridget E Bunner
(74) *Attorney, Agent, or Firm* — Clark & Elbing LLP; Susan M. Michaud

(57) ABSTRACT

Provided are anti-PAD4 antibodies having excellent properties and an excellent method for treatment of RA. Used are anti-PAD4 antibodies that specifically bind to an epitope containing positions 345, 347, and 348 of PAD4. These anti-PAD4 antibodies may inhibit the citrullination activity of PAD4. In addition, these anti-PAD4 antibodies may have a KD (M) of $9.0 \times 10^{-9}$ or less. Optionally, the anti-PAD4 antibody and a TNFα inhibitor are used in combination.

21 Claims, 26 Drawing Sheets

Specification includes a Sequence Listing.

(56) References Cited

OTHER PUBLICATIONS

Lipman et al. Monoclonal versus polyclonal antibodies: distinguishing characteristics, applications, and information resources. ILAR J 46(3): 258-268, 2005.*
Paul, William E., Fundamental Immunology, 3rd Edition, Raven Press, New York, Chapt. 8, pp. 292-295 (1993).*
Rudikoff et al. Single amino acid substitution altering antigen-binding specificity. Proc Natl Acad Sci USA 79: 1979-1983, 1982.*
Arita et al. Structural basis for Ca2+-induced activation of human PAD4. Nature Structural Mol Biol 11(8): 777-783, 2004.*
Rohrbach et al. Activation of PAD4 in NET formation. Front Immunol 3: article 360, 2012.*
Sato et al. English language translation of WO 2012/026309, Jul. 12, 2019 (large font version).*
International Search Report for International Application No. PCT/JP2016/057030, filed Mar. 7, 2016, Sato et al., "Novel Anti-PAD4 Antibody," dated Jun. 7, 2016 (6 pages).
Ishigami et al., "Two novel sandwich ELISAs identify PAD4 levels and PAD4 autoantibodies in patients with rheumatoid arthritis," Mod Rheumatol. 23(4):794-803 (2013).
Shelef et al., "Peptidylarginine deiminase 4 contributes to tumor necrosis factor alpha-induced inflammatory arthritis," Arthritis Rheumatol. 66(6):1482-91 (2014).
Suzuki et al., "Functional haplotypes of PADI4, encoding citrullinating enzyme peptidylarginine deiminase 4, are associated with rheumatoid arthritis," Nat Genet. 34(4):395-402 (2003).
Office Action dated May 13, 2019 for European Patent Application No. 16761721.6, Sato et al., "Novel Anti-PAD4 Antibody," filed Mar. 7, 2016 (8 pages).
Reineke, "Antibody epitope mapping using arrays of synthetic peptides," DNA Repair Protocols. Methods in Molecular Biology. Humana Press. 248:443-463, 2004.
Andrade et al., "Autocitrullination of human peptidyl arginine deiminase type 4 regulates protein citrullination during cell activation," Arthritis Rheum. 62(6):1630-40 (2010).
Extended European Search Report dated Dec. 20, 2017 for European Patent Application No. 16761721.6, Sato et al., "Novel Anti-PAD4 Antibody," filed Mar. 7, 2016 (13 pages).
Stave et al., "Antibody and antigen contact residues define epitope and paratope size and structure," J Immunol. 191(3):1428-35 (2013).
Wu et al., "Humanization of a murine monoclonal antibody by simultaneous optimization of framework and CDR residues," J Mol Biol. 294(1):151-62 (1999).
Bardelli et al., "Epitope Mapping by Solution NMR Spectroscopy," J Mol Recognit. 28(6):393-400 (2015).
Communication Pursuant to Article 94(3) EPC for European Application No. 16761721.6, dated Apr. 17, 2020 (11 pages).
Simonyan et al., "Conformational Epitope Mapping by Cross-link Mass Spectrometry: Analysis of Ipilimumab, Nivolumab and Pembrolizumab," https://covalx.com/pdf/171113-CovalX-XLMS%20Xray%20Comparions-PEGSEU17.pdf, dated Nov. 15, 2017, retrieved May 27, 2020 (1 page).
Abbott et al., "Current approaches to fine mapping of antigen-antibody interactions," Immunology 142(4):526-535 (2014).
Summons to attend oral proceedings pursuant to Rule 115(1) EPC dated Apr. 7, 2022, for European Application No. 16761721.6, Sato et al., "Novel Anti-PAD4 Antibody," filed Mar. 7, 2016 (13 pages).

* cited by examiner

[Fig.1]

ELISA

【Fig.4】
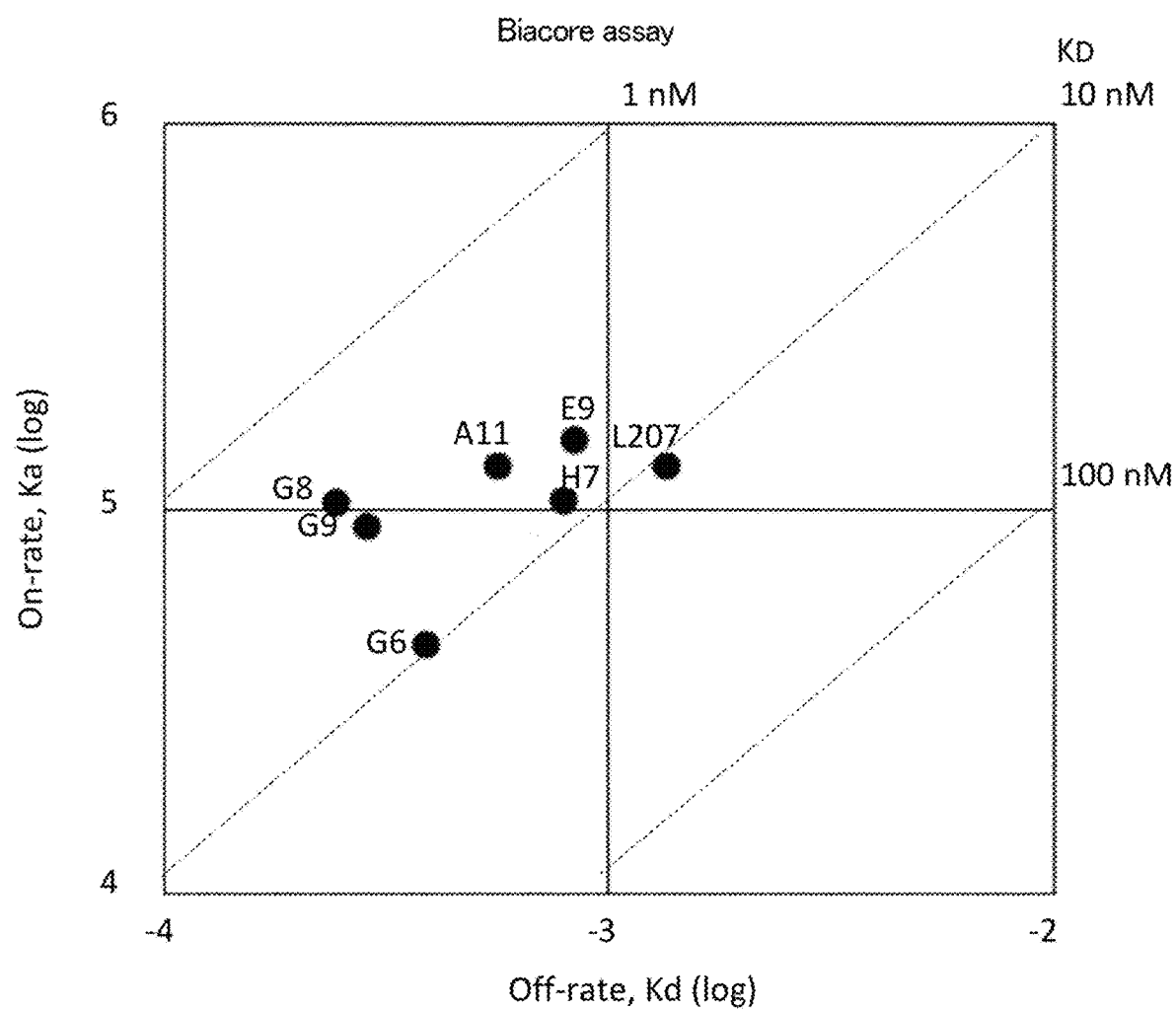

[Fig 5]

| Amino acid No. | 340 | 341 | 342 | 343 | 344 | 345 | 346 | 347 | 348 | 349 | 350 | 351 | 352 | 353 | 354 | 355 | 356 |
|---|---|---|---|---|---|---|---|---|---|---|---|---|---|---|---|---|---|
| Amino acid | E | E | N | M | D | D | Q | W | M | Q | D | E | M | E | I | G | Y |
| A11 | 1.954 | 2.001 | 2.054 | 2.03 | 1.667 | 0.628 | 2.086 | 0.021 | 0.023 | 1.907 | 1.799 | 1.885 | 1.893 | 1.855 | 1.853 | 1.875 | 1.924 |
|  |  | 1.984 |  |  | 0.039 |  |  | 0.043 |  |  | 1.253 |  |  | 1.87 |  |  | 1.886 |
| E9 | 1.892 | 1.995 | 1.922 | 1.914 | 1.381 | 0.177 | 1.925 | 0.047 | 0.017 | 1.904 | 1.201 | 1.91 | 1.771 | 1.819 | 1.804 | 1.833 | 1.877 |
|  |  | 1.903 |  |  | 0.022 |  |  | 0.027 |  |  | 1.336 |  |  | 1.815 |  |  | 1.852 |
| G6 | 1.913 | 1.987 | 1.951 | 1.922 | 1.774 | 0.035 | 1.978 | 0.042 | 0.015 | 1.849 | 1.846 | 1.915 | 1.835 | 1.861 | 1.866 | 1.871 | 1.871 |
|  |  | 1.919 |  |  | 0.018 |  |  | 0.083 |  |  | 1.729 |  |  | 1.852 |  |  | 1.88 |
| G8 | 1.955 | 1.941 | 1.907 | 1.927 | 1.854 | 0.083 | 1.975 | 0.04 | 0.233 | 1.918 | 1.878 | 1.906 | 1.875 | 1.892 | 1.847 | 1.86 | 1.918 |
|  |  | 1.896 |  |  | 0.065 |  |  | 0.178 |  |  | 1.856 |  |  | 1.883 |  |  | 1.862 |
| G9 | 1.926 | 1.963 | 1.944 | 2.034 | 1.479 | 0.039 | 1.981 | 0.038 | 0.253 | 1.874 | 1.878 | 1.955 | 1.874 | 1.883 | 1.887 | 1.852 | 1.881 |
|  |  | 1.919 |  |  | 0.019 |  |  | 0.131 |  |  | 1.849 |  |  | 1.885 |  |  | 1.918 |
| H7 | 1.9 | 1.952 | 1.904 | 1.952 | 0.462 | 0.033 | 1.871 | 0.066 | 0.065 | 1.867 | 1.857 | 1.99 | 1.81 | 1.859 | 1.828 | 1.851 | 1.874 |
|  |  | 1.904 |  |  | 0.016 |  |  | 0.044 |  |  | 1.667 |  |  | 1.867 |  |  | 1.864 |
| L207 | 1.418 | 1.552 | 1.57 | 1.409 | 1.485 | 1.53 | 1.486 | 1.32 | 1.325 | 1.534 | 0.025 | 1.269 | 1.437 | 1.485 | 0.01 | 0.143 | 1.35 |
|  |  | 1.522 |  |  | 1.504 |  |  | 0.094 |  |  | 0.031 |  |  | 0.014 |  |  | 0.934 |

*Shaded regions are amino acid residues where no significant reactivity was observed after Ala scan.
*The upper rows represent the case of single amino acid substitution and the lower rows represent the case of 3-amino-acid substitution.
*The cut-off threshold is 50% of the affinity of the anti-PAD4 polyclonal antibody.

[Fig.6]
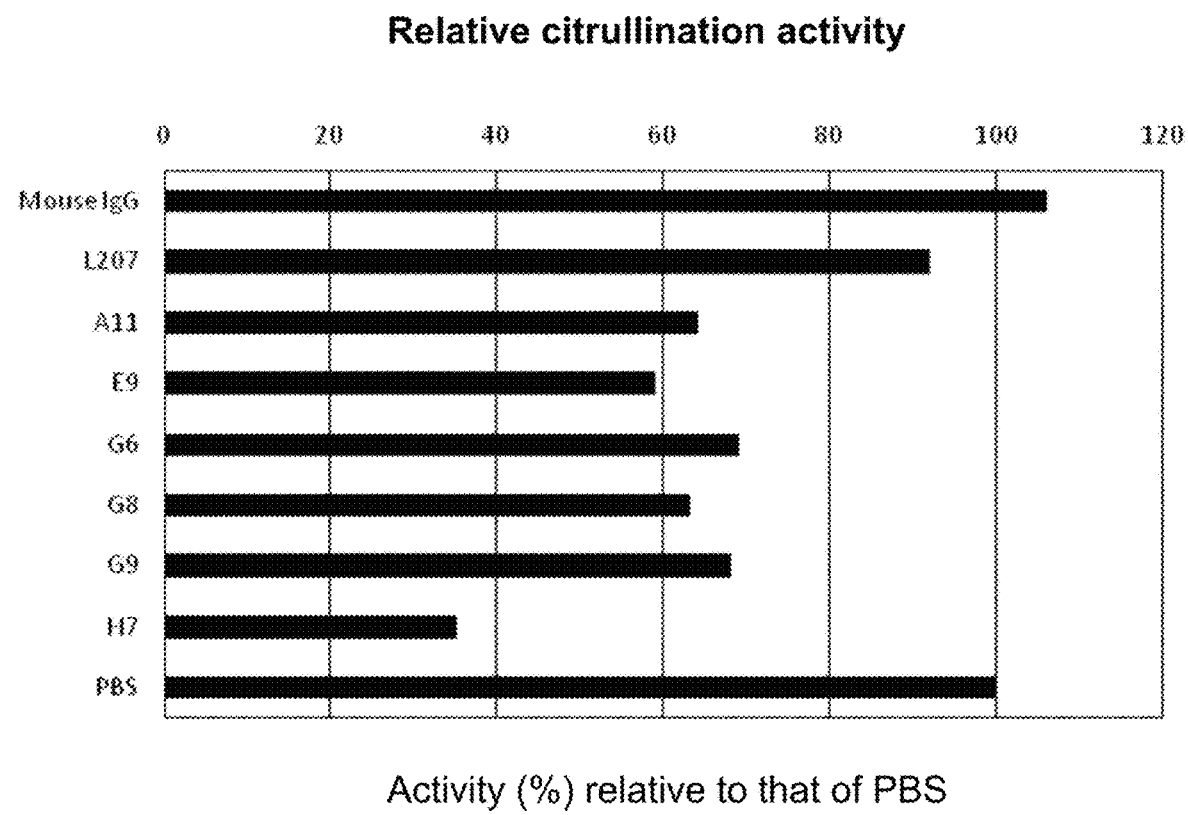

[Fig.7]

[Fig.8]
In vivo Experiment using a CAIA model mouse
-Samples-
- Anti-PAD4 antibody (G8), n = 7
- Anti-DNP antibody, n = 7
- vehicle (PBS), n = 5
-Inflammation model-
- Collagen antibody-induced arthritis model mouse
- Dosage/Method: 1 mg/body (50 mg/kg) × 5/intraperitoneal administration
-Endpoints-
- Arthritis score
- Swelling measurement (insteps and joints)
-Schedule-
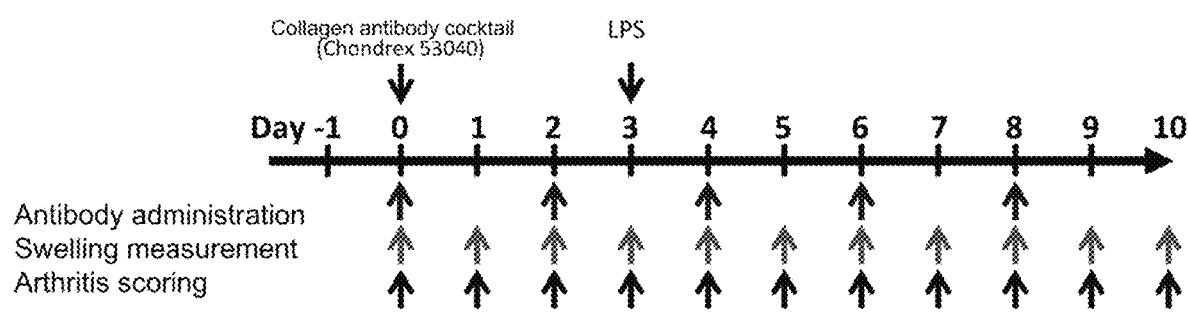

[Fig.9]

[Fig.10]
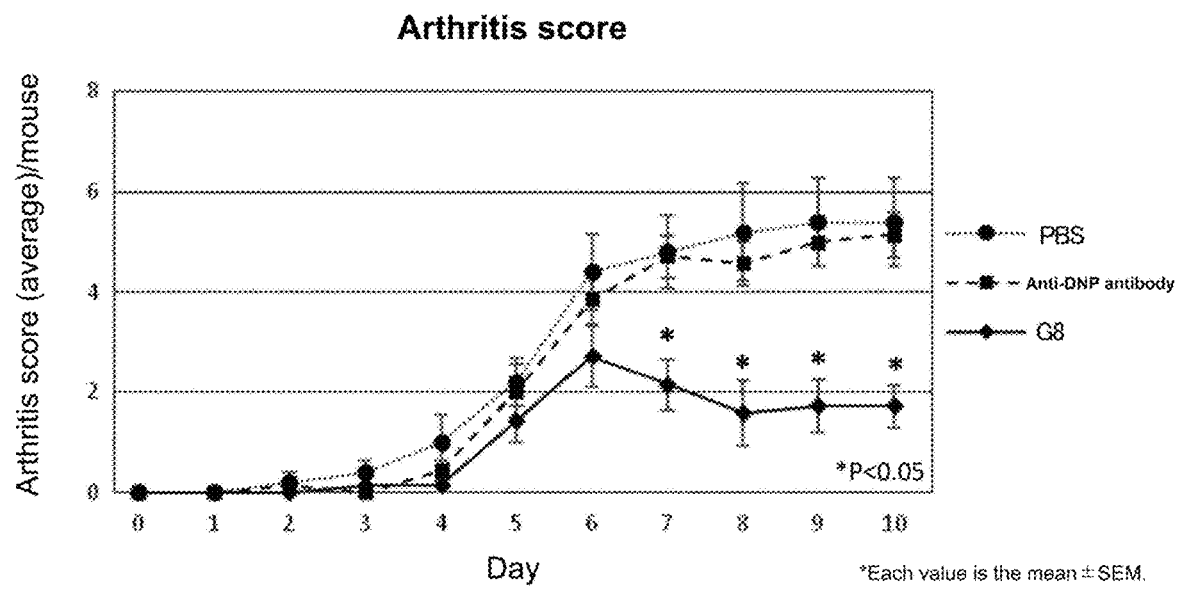
[Fig.11]
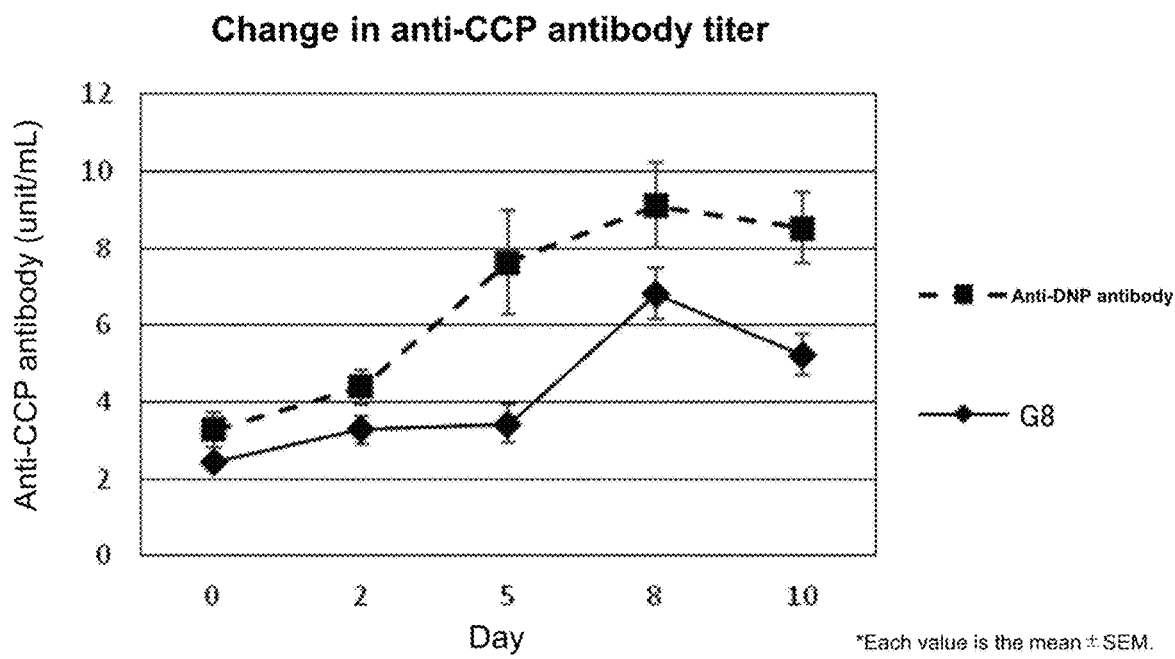

[Fig.12]
Figure 12A — Section images at or near a finger joint (G8)
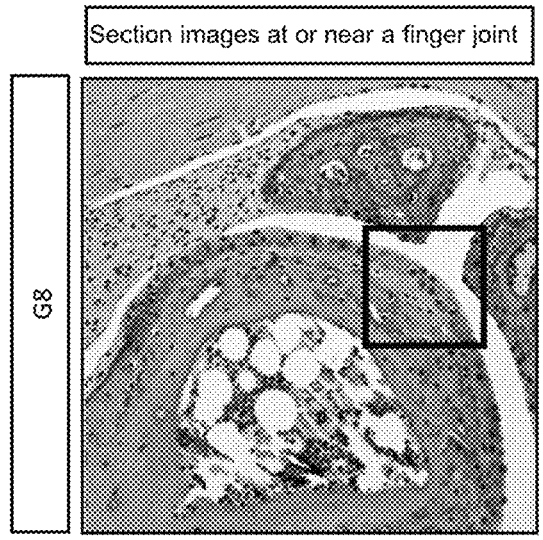
Figure 12B — Magnified views at or near a chondrocyte layer
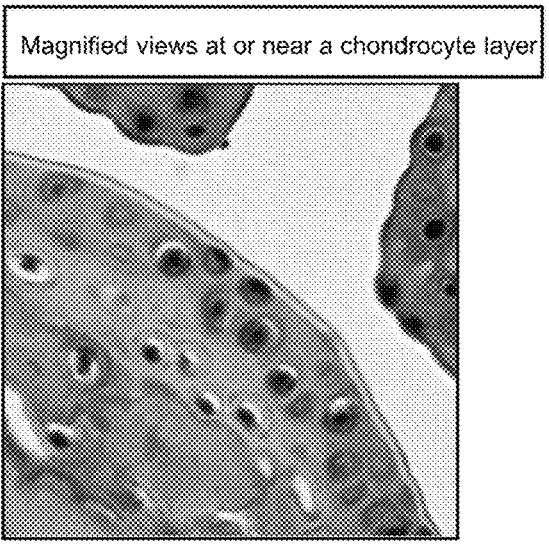
Figure 12C — Anti-DNP antibody
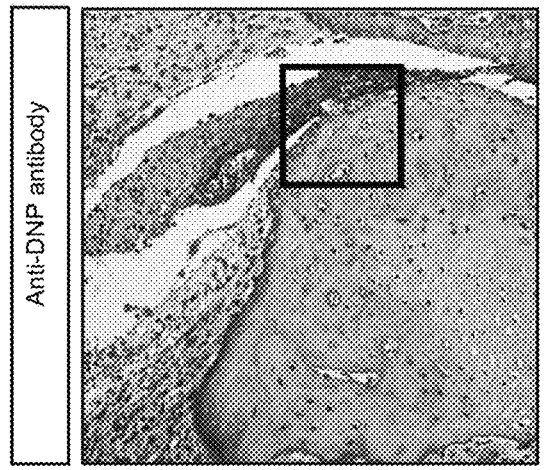
Figure 12D
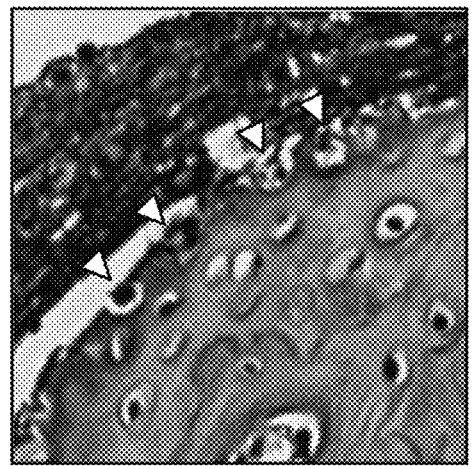
Figure 12E — PBS, Finger joint bone
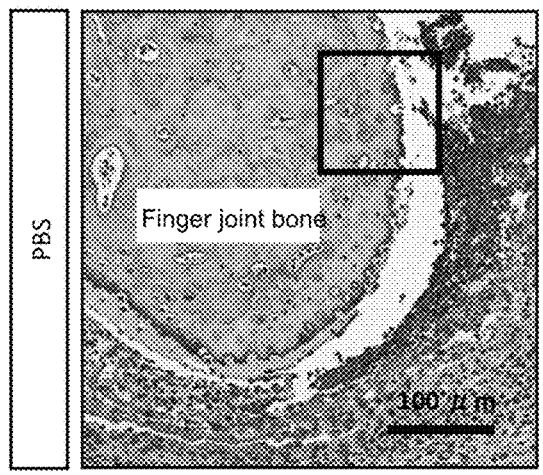
Figure 12F
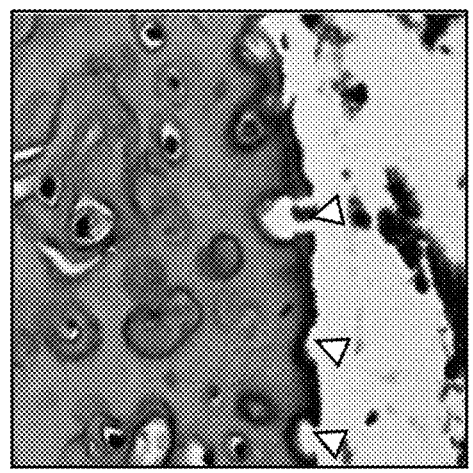

[Fig.13]
_In vivo_ Experiment using a CAIA model mouse
-Samples-
- Anti-PAD4 antibody (G8), n = 7
- Anti-PAD4 antibody (H7), n = 5
- Anti-DNP antibody, n = 5
-Inflammation model-
- Collagen antibody-induced arthritis model mouse
- Dosage/Method: 1 mg/body (50 mg/kg) × 5/intraperitoneal administration
-Endpoints-
- Arthritis score
- Swelling measurement (insteps and joints)
-Schedule-
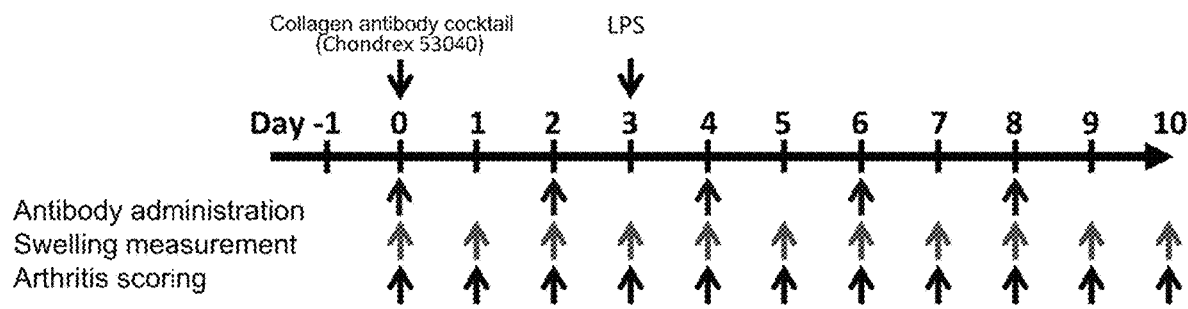

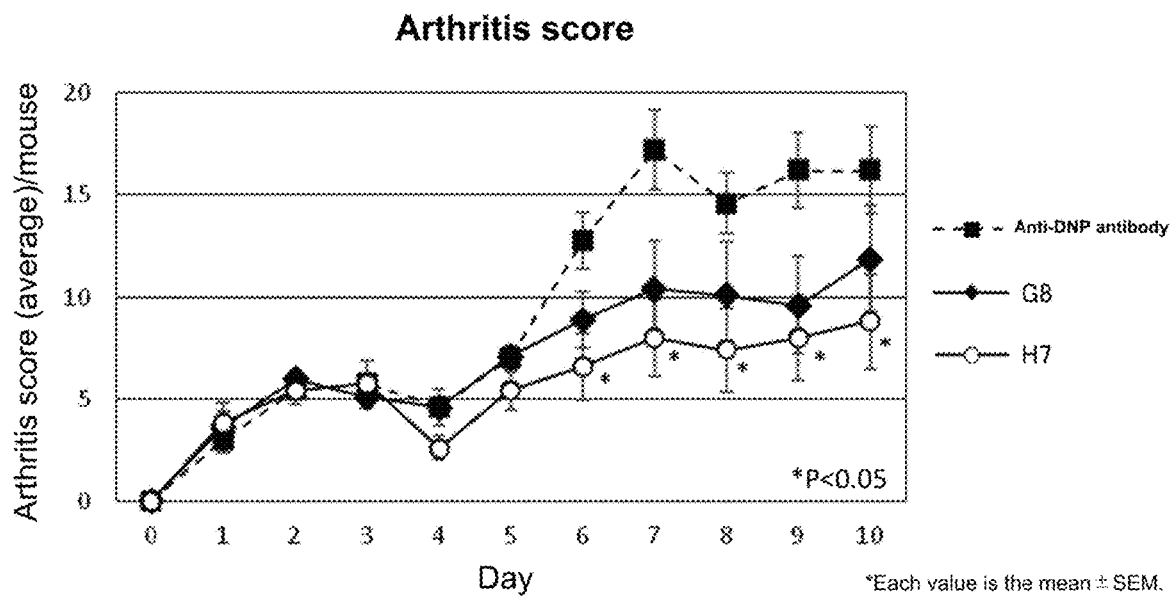

[Fig.16]

>H-chain constant region (SEQ ID NO: 153)
ASTKGPSVFPLAPSSKSTSGGTAALGCLVKDYFPEPVTVSWNSGALTSGVHTFPAVLQSSGLYSLSSVVTVPSSSLGTQTYICNVNHKPSN
TKVDKKVEPKSCDKTHTCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGK >L-chain constant region (SEQ ID NO: 154)
GTVAAPSVFIFPPSDEQLKSGTASVVCLLNNFYPREAKVQWKVDNALQSGNSQESVTEQDSKDSTYSLSSTLTLSKADYEKHKVYACEVTH
QGLSSPVTKSFNRGEC

[Fig.17]

>G8H7-H4.00 (SEQ ID NO:155)
EVQLLESGGGLVQPGGSLRLSCAASGFTFSTYAMGWVRQAPGKGLEFVAAIRNDGSWTGYGAAVKGRFTISRDNSKNTLYLQMNSLRAEDT
AVYYCAKYTGSSGGSIGAWGQGTLVTVSS

>G8H7-H4.15 (SEQ ID NO:156)
EVQLLESGGGLVQPGGSLRLSCAASGFTFSTYAMGWVRQAPGKGLEFVSAIRNDGSWTGYGAAVKGRFTISRDNSKNTVYLQMNSLRAEDT
AVYYCAKYTGSSGGSIGAWGQGTLVTVSS

>G8H7-H4.32 (SEQ ID NO:157)
EVQLLESGGGLVQPGGSLRLSCAASGFTFSTYAMGWVRQAPGKGLEFVAAIRNDGSWTGYGAAVKGRVTISRDNSKNTVYLQMNSLRAEDT
AVYYCAKYTGSSGGSIGAWGQGTLVTVSS

>G8-L4.00 (SEQ ID NO:158)
SYELTQPPSVSVSPGQTARITCSGGNRNYYYGWYQQKPGQAPVLVIYANDKRPSGIPERFSGSSSGTTVTLTISGVQAEDEADYYCGTADT
GKYVFGGGTKLTVL

>G8-L4.06 (SEQ ID NO:159)
SYELTQPPSVSVSPGQTARITCSGGNRNYYYGWYQQKPGQAPVTVIYANDKRPSGIPERFSGSYSGNTTTLTISGVQAEDEADYYCGTADT
GKYVFGGGTKLTVL

>G8-L4.17 (SEQ ID NO:160)
SYELTQPPSVSVSPGQTARITCSGGNRNYYYGWYQQKPGQAPVTVIYANDKRPSGIPERFSGSTSGNTTTLTISGVQAEDEADYYCGTADT
GKYVFGGGTKLTVL

>G8-L4.29 (SEQ ID NO:161)
SYELTQPPSVSVSPGQTARITCSGGNRNYYYGWYQQKPGQAPVTVIYANDKRPSGIPERFSGSNSGSTTTLTISGVQAEDEADYYCGTADT
GKYVFGGGTKLTVL

CDRs are underlined.

[Fig.18]

>G8H7-H4.00 (SEQ ID NO:162)
EVQLLESGGGLVQPGGSLRLSCAASGFTFS<u>TYAMG</u>WVRQAPGKGLEFVAA<u>IRNDGSWTGYGAAVKG</u>RFTISRDNSKNTLYLQMNSLRAEDT
AVYYCAK<u>YTGSSGGSIGAW</u>GQGTLVTVSS

>G8H7-H4.15 (SEQ ID NO:163)
EVQLLESGGGLVQPGGSLRLSCAASGFTFS<u>TYAMG</u>WVRQAPGKGLEFVSA<u>IRNDGSWTGYGAAVKG</u>RFTISRDNSKNTVYLQMNSLRAEDT
AVYYCAK<u>YTGSSGGSIGAW</u>GQGTLVTVSS SEQ ID NO:

>G8H7-H4.32 (SEQ ID NO:164)
EVQLLESGGGLVQPGGSLRLSCAASGFTFS<u>TYAMG</u>WVRQAPGKGLEFVAA<u>IRNDGSWTGYGAAVKG</u>RVTISRDNSKNTVYLQMNSLRAEDT
AVYYCAK<u>YTGSSGGSIGAW</u>GQGTLVTVSS

>H7-L4.00 (SEQ ID NO:165)
SYELTQPPSVSVSPGQTARITC<u>SGGSGRYYYG</u>WYQQKPGQAPVLVIY<u>SSTHRPSG</u>IPERFSGSSSGTTVTLTISGVQAEDEADYYC<u>GTADS
SSYV</u>FGGGTKLTVL

>H7-L4.06 (SEQ ID NO:166)
SYELTQPPSVSVSPGQTARITC<u>SGGSGRYYYG</u>WYQQKPGQAPVTVIY<u>SSTHRPSG</u>IPERFSGSYSGNTTTLTISGVQAEDEADYYC<u>GTADS
SSYV</u>FGGGTKLTVL

>H7-L4.15 (SEQ ID NO:167)
SYELTQPPSVSVSPGQTARITC<u>SGGSGRYYYG</u>WYQQKPGQAPVTVIY<u>SSTHRPSG</u>IPERFSGSNSGNTTTLTISGVQAEDEADYYC<u>GTADS
SSYV</u>FGGGTKLTVL

>H7-L4.17 (SEQ ID NO:168)
SYELTQPPSVSVSPGQTARITC<u>SGGSGRYYYG</u>WYQQKPGQAPVTVIY<u>SSTHRPSG</u>IPERFSGSTSGNTTTLTISGVQAEDEADYYC<u>GTADS
SSYV</u>FGGGTKLTVL

>H7-L4.29 (SEQ ID NO:169)
SYELTQPPSVSVSPGQTARITC<u>SGGSGRYYYG</u>WYQQKPGQAPVTVIY<u>SSTHRPSG</u>IPERFSGSNSGSTTTLTISGVQAEDEADYYC<u>GTADS
SSYV</u>FGGGTKLTVL

CDRs are underlined.

IgG1-type full length (H4.00)SEQ ID NO: 170)
EVQLLESGGGLVQPGGSLRLSCAASGFTFSSYGMGWVRQAPGKGLEFVAAIRNDGSWTGYGAAVKGRFTISRDNSKNTLYLQMNSLRAEDT
AVYYCAKTTGSRGGSIDAWGQGTLVTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNVFSCSVMHEALHNHYTQKSLSLSPGK*

L-chain: κ-type full length (L4.29)(the sequence of the L-chain is the same as of G9)(SEQ ID NO: 171)
SYELTQPPSVSVSPGQTARITCSGGGRYYYGWYQQKPGQAPVTVIYANDKRPSGIPERFSGSNSGSTTTLTISGVQAEDEADYYCGSAETS
SYVFGGGTKLTVLGTVAAPSVFIFPPSDEQLKSGTASVVCLLNNFYPREAKVQWKVDNALQSGNSQESVTEQDSKDSTYSLSSTLTLSKAD
YEKHKVYACEVTHQGLSSPVTKSFNRGEC*

G8

IgG1-type full length (H4.00)(the sequence of the H-chain is identical among G8, G9, and H7)(SEQ ID NO: 172)
EVQLLESGGGLVQPGGSLRLSCAASGFTFSTYAMGWVRQAPGKGLEFVAAIRNDGSWTGYGAAVKGRFTISRDNSKNTLYLQMNSLRAEDT
AVYYCAKYTGSSGGSIGAWGQGTLVTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNVFSCSVMHEALHNHYTQKSLSLSPGK*

L-chain: κ-type full length (L4.29)(SEQ ID NO: 173)
SYELTQPPSVSVSPGQTARITCSGGNRNYYYGWYQQKPGQAPVTVIYANDKRPSGIPERFSGSNSGSTTTLTISGVQAEDEADYYCGTADT
GKYVFGGGTKLTVLGTVAAPSVFIFPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC*

CDRs are underlined.
Constant regions are double-underlined.

IgG1-type full length (H4.00)(the sequence of the H-chain is identical among G8, G9, and H7)(SEQ ID NO: 174)
EVQLLESGGGLVQPGGSLRLSCAASGFTFSTYAMGWVRQAPGKGLEFVAAIRNDGSWTGYGAAVKGRFTISRDNSKNTLYLQMNSLRAEDT
AVYYCAKYTGSSGGSIGAWGQGTLVTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNVFSCSVMHEALHNHYTQKSLSLSPGK*

L-chain: κ-type full length (L4.29)(the sequence of the L-chain is the same as of A11)(SEQ ID NO: 175)
SYELTQPPSVSVSPGQTARITCSGGGRYYYGWYQQKPGQAPVTVIYANDKRPSGIPERFSGSNSGSTTTLTISGVQAEDEADYYCGSAETS
SYVFGGGTKLTVLGTVAAPSVFIFPPSDEQLKSGTASVVCLLNNFYPREAKVQWKVDNALQSGNSQESVTEQDSKDSTYSLSSTLTLSKAD
YEKHKVYACEVTHQGLSSPVTKSFNRGEC*

H7

IgG1-type full length (H4.00)(the sequence of the H-chain is identical among G8, G9, and H7)(SEQ ID NO: 176)
EVQLLESGGGLVQPGGSLRLSCAASGFTFSTYAMGWVRQAPGKGLEFVAAIRNDGSWTGYGAAVKGRFTISRDNSKNTLYLQMNSLRAEDT
AVYYCAKYTGSSGGSIGAWGQGTLVTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNVFSCSVMHEALHNHYTQKSLSLSPGK*

L-chain: κ-type full length (L4.29)(SEQ ID NO: 177)
SYELTQPPSVSVSPGQTARITCSGGGSGRYYYGWYQQKPGQAPVTVIYSSTHRPSGIPERFSGSNSGSTTTLTISGVQAEDEADYYCGTADS
SSYVFGGGTKLTVLGTVAAPSVFIFPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC*

CDRs are underlined.
Constant regions are double-underlined.

| Ab conc. (μg/ml) | H4.00/L4.00 | H4.00/L4.06 | H4.00/L4.17 | H4.00/L4.29 | H4.15/L4.00 | H4.15/L4.06 | H4.15/L4.17 | H4.15/L4.29 | H4.32/L4.00 | H4.32/L4.06 | H4.32/L4.17 | H4.32/L4.29 |
|---|---|---|---|---|---|---|---|---|---|---|---|---|
| 1 | 1.881 | 1.801 | 1.798 | 1.796 | 1.846 | 1.775 | 1.835 | 1.837 | 1.867 | 1.786 | 1.825 | 1.837 |
| 0.5 | 1.839 | 1.83 | 1.8 | 1.82 | 1.859 | 1.79 | 1.822 | 1.811 | 1.913 | 1.811 | 1.831 | 1.843 |
| 0.25 | 1.7 | 1.807 | 1.813 | 1.841 | 1.87 | 1.874 | 1.807 | 1.862 | 1.836 | 1.853 | 1.834 | 1.848 |
| 0.125 | 1.311 | 1.854 | 1.819 | 1.851 | 1.869 | 1.913 | 1.868 | 1.858 | 1.763 | 1.861 | 1.865 | 1.886 |
| 0.0625 | 0.806 | 1.946 | 1.891 | 1.882 | 1.843 | 1.915 | 1.925 | 1.906 | 1.52 | 1.913 | 1.884 | 1.902 |
| 0.03125 | 0.454 | 1.834 | 1.845 | 1.881 | 1.517 | 1.902 | 1.858 | 1.846 | 1.052 | 1.825 | 1.835 | 1.882 |
| 0.015625 | 0.247 | 1.64 | 1.622 | 1.549 | 1.107 | 1.68 | 1.658 | 1.564 | 0.649 | 1.601 | 1.56 | 1.693 |
| 0.0078125 | 0.131 | 1.217 | 1.312 | 1.196 | 0.707 | 1.315 | 1.236 | 1.146 | 0.364 | 1.211 | 1.199 | 1.259 |

H7

| Ab conc. (μg/ml) | H4.00/L4.00 | H4.00/L4.06 | H4.00/L4.15 | H4.00/L4.17 | H4.15/L4.06 | H4.15/L4.15 | H4.15/L4.17 | H4.32/L4.00 | H4.32/L4.06 | H4.32/L4.15 | H4.32/L4.17 |
|---|---|---|---|---|---|---|---|---|---|---|---|
| 1 | 1.924 | 1.86 | 1.861 | 1.857 | 1.865 | 1.837 | 1.819 | 1.772 | 1.823 | 1.767 | 1.789 | 1.791 |
| 0.5 | 1.914 | 1.859 | 1.869 | 1.848 | 1.879 | 1.824 | 1.83 | 1.817 | 1.815 | 1.806 | 1.782 | 1.81 |
| 0.25 | 1.894 | 1.892 | 1.891 | 1.864 | 1.897 | 1.816 | 1.84 | 1.814 | 1.848 | 1.863 | 1.839 | 1.861 |
| 0.125 | 1.882 | 1.868 | 1.873 | 1.872 | 1.844 | 1.839 | 1.83 | 1.814 | 1.772 | 1.823 | 1.866 | 1.856 |
| 0.0625 | 1.716 | 1.997 | 1.916 | 1.907 | 1.708 | 1.829 | 1.867 | 1.897 | 1.648 | 1.936 | 1.935 | 1.975 |
| 0.03125 | 1.209 | 1.896 | 1.891 | 1.853 | 1.23 | 1.822 | 1.821 | 1.813 | 1.173 | 1.901 | 1.891 | 1.948 |
| 0.015625 | 0.752 | 1.749 | 1.713 | 1.707 | 0.764 | 1.68 | 1.653 | 1.633 | 0.713 | 1.644 | 1.767 | 1.771 |
| 0.0078125 | 0.441 | 1.258 | 1.31 | 1.298 | 0.429 | 1.215 | 1.245 | 1.31 | 0.389 | 1.22 | 1.337 | 1.284 |

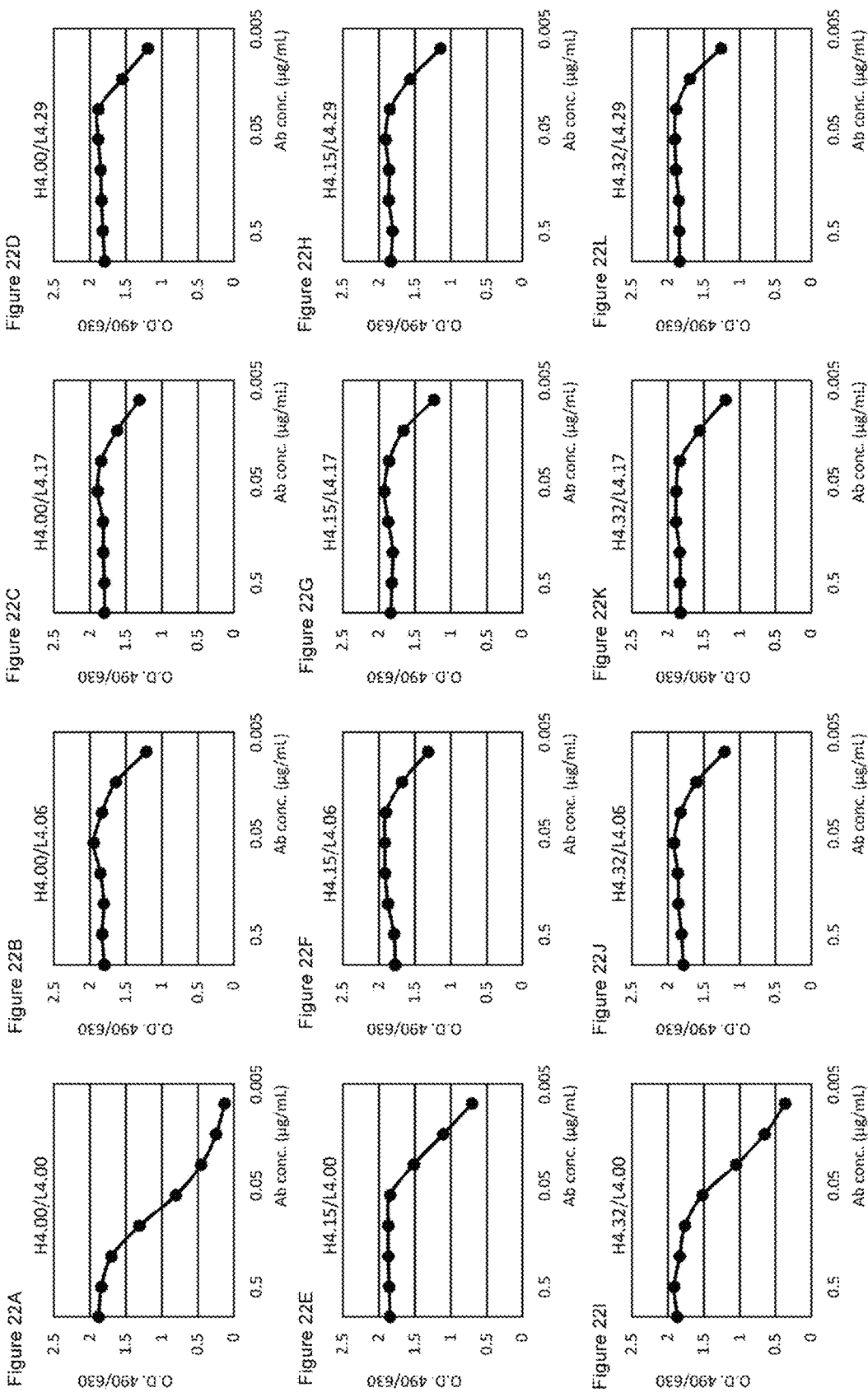
[Fig. 22]

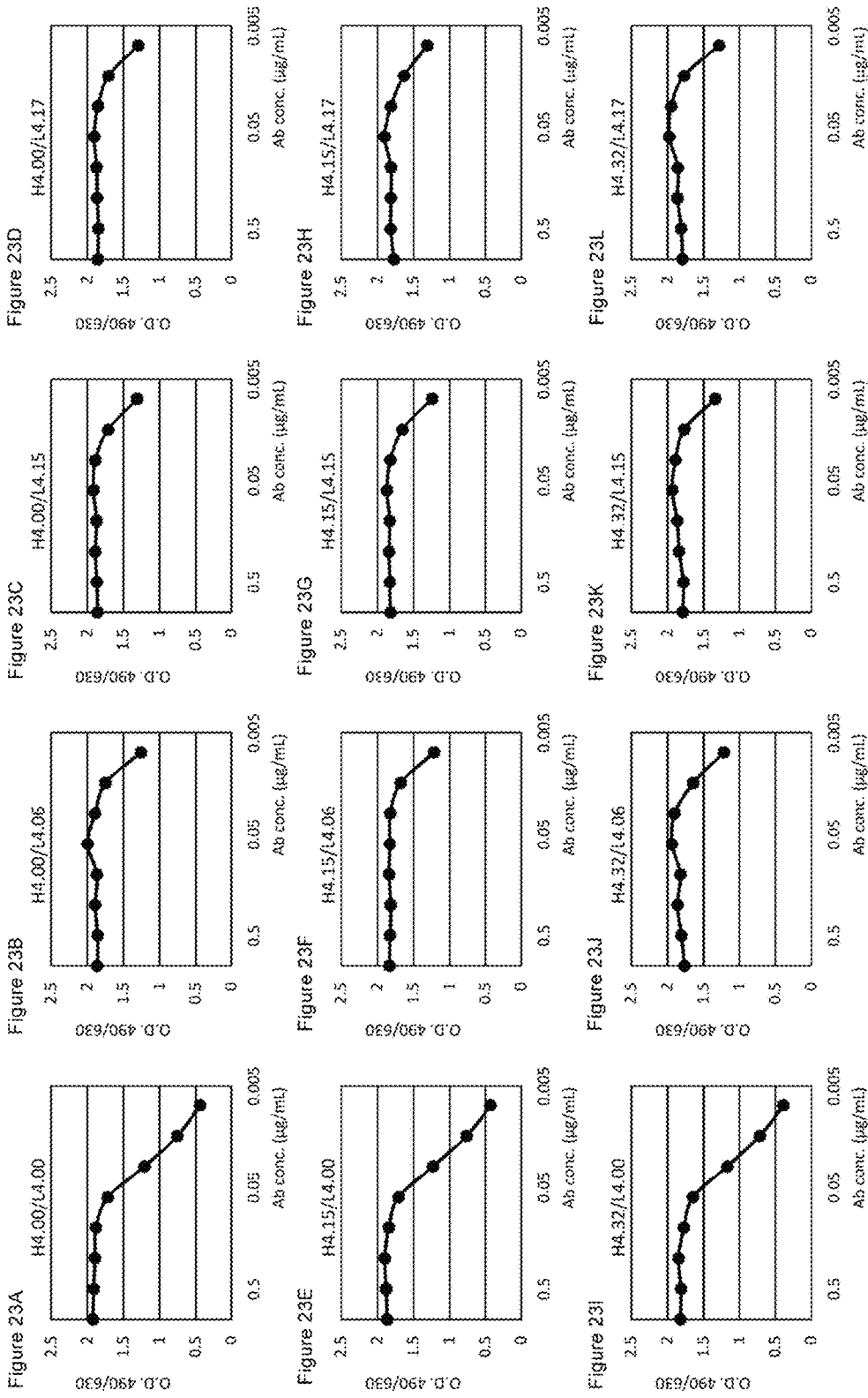
[Fig. 23]

[Fig.24]

| Ab conc. (μg/mL) | A11 | G8 | G9 | H7 |
|---|---|---|---|---|
| 1 | 2.077 | 2.057 | 2.057 | 2.080 |
| 0.2 | 2.080 | 2.101 | 2.034 | 2.066 |
| 0.04 | 2.075 | 2.124 | 2.088 | 2.101 |
| 0.008 | 1.700 | 1.790 | 1.662 | 1.723 |
| 0.0016 | 0.733 | 0.851 | 0.785 | 0.766 |
| 0.00032 | 0.245 | 0.287 | 0.252 | 0.269 |
| 0.000064 | 0.122 | 0.139 | 0.116 | 0.130 |
| 0 | 0.064 | 0.069 | 0.069 | 0.083 |

[Fig.25]

>H-chain variable region (SEQ ID NO: 178)
GAGGTGCAGCTGTTGGAGTCTGGGGGAGGACTGGTGCAGCCTGGCGGAAGCCTGAGACTGTCTTGTGCCGCCAGCGGCTTCACCTTCAGCA
CCTATGCCATGGGCTGGGTGCGCCAGGCCCCTGGAAAGGGCCTGGAATTTGTGGCCGCCATCCGGAACGATGGCAGCTGGACAGGATATGG
CGCCGCTGTGAAGGGCCGGTTCACCATCAGCCGGGACAACAGCAAGAACACCCTGTACCTGCAGATGAACAGCCTGCGGGCCGAGGACACC
GCCGTGTACTACTGTGCCAAGTACACCGGCAGCAGCGGCGGCTCTATTGGAGCTTGGGGACAGGGAACCCTGGTCACCGTCTCCTCA >H-chain constant region (SEQ ID NO: 179)
GCCAGCACCAAGGGCCCCAGCGTGTTCCCTCTGGCCCCTTGTAGCAGAAGCACCAGCGAGTCTACAGCCGCCCTGGGCTGCCTCGTGAAGG
ACTACTTTCCCGAGCCCGTGACCGTGTCCTGGAACTCTGGCGCTCTGACAAGCGGCGTGCACACCTTCCAGCCGTGCTGCAGAGCAGCGG
CCTGTACTCTCTGAGCAGCGTCGTGACTGTGCCCAGCAGCTCTCTGGGCACCAAGACCTACACCTGTAACGTGGACCACAAGCCCAGCAAC
ACCAAGGTGGACAAGCGGGTGGAATCTAAGTACGGCCCTCCCTGCCCTCCTTGCCCAGCCCCTGAATTTCTGGGCGGACCCTCCGTGTTCC
TGTTCCCCCCAAAGCCCAAGGACACCCTGATGATCAGCCGGACCCCCGAAGTGACCTGCGTGGTGGTGGATGTGTCCCAGGAAGATCCCGA
GGTGCAGTTCAATTGGTACGTGGACGGCGTGGAAGTGCACAACGCCAAGACCAAGCCTAGAGAGGAACAGTTCAACAGCACCTACCGGGTG
GTGTCCGTGCTGACAGTGCTGCATCAGGACTGGCTGAACGGCAAAGAGTACAAGTGCAAGGTGTCCAACAAGGGCCTGCCCAGCTCCATCG
AGAAAACCATCAGCAAGGCCAAGGGCCAGCCCCGCGAACCCCAGGTGTACACACTGCCTCCAAGCCAGGAAGAGATGACCAAGAACCAGGT
GTCCCTGACCTGTCTCGTGAAAGGCTTCTACCCCTCCGATATCGCCGTGGAATGGGAGAGCAACGGCCAGCCGAGAACAACTACAAGACA
ACCCCCCCTGTGCTGGACAGCGACGGCTCATTCTTCCTGTACAGCAGACTGACCGTGGACAAGAGCCGGTGGCAGGAAGGCAACGTGTTCA
GCTGCAGCGTGATGCACGAGGCCCTGCACAACCACTACACCCAGAAGTCCCTGTCTCTGAGCCTGGGCAAGTGA >L-chain variable region (SEQ ID NO: 180)
AGCTATGAGCTGACTCAGCCACCCTCGGTGTCAGTGTCTCCTGGCCAGACCGCCAGAATCACATGTAGCGGCGGCAGCGGCCGGTACTACT
ACGGCTGGTATCAGCAGAAGCCCGGCCAGGCCCCTGTGACCGTGATCTACAGCAGCACCCACAGACCCAGCGGCATCCCCGAGAGATTCAG
CGGCAGCAATAGCGGCTCCACCACCACCCTGACAATCAGCGGAGTGCAGGCCGAGGACGAGGCCGATTACTACTGTGGCACCGCCGACAGC
AGCAGCTACGTGTTCGGCGGAGGAACCAAGCTGACCGTCCTG >L-chain constant region (SEQ ID NO: 181)
GGTCAGCCCAAGGCTGCCCCCTCGGTCACTCTGTTCCCGCCCTCCTCTGAGGAGCTTCAAGCCAACAAGGCCACACTGGTGTGTCTCATAA
GTGACTTCTACCCGGGAGCCGTGACAGTGGCCTGGAAGGCAGATAGCAGCCCCGTCAAGGCGGGAGTGGAGACCACCACACCCTCCAAACA
AAGCAACAACAAGTACGCGGCCAGCAGCTATCTGAGCCTGACGCCTGAGCAGTGGAAGTCCCACAGAAGCTACAGCTGCCAGGTCACGCAT
GAAGGGAGCACCGTGGAGAAGACAGTGGCCCCTACAGAATGTTCATAG

[Fig.26]

>H-chain variable region (SEQ ID NO: 182)
EVQLLESGGGLVQPGGSLRLSCAASGFTFSTYAMGWVRQAPGKGLEFVAAIRNDGSWTGYGAAVKGRFTISRDNSKNTLYLQMNSLRAEDT
AVYYCAKYTGSSGGSIGAWGQGTLVTVSS >H-chain constant region (SEQ ID NO: 183)
ASTKGPSVFPLAPCSRSTSESTAALGCLVKDYFPEPVTVSWNSGALTSGVHTFPAVLQSSGLYSLSSVVTVPSSSLGTKTYTCNVDHKPSN
TKVDKRVESKYGPPCPPCPAPEFLGGPSVFLFPPKPKDTLMISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLPPSQEEMTKNQVSLTCLVKGFYPSDIAVEWESNGQPENNYKT
TPPVLDSDGSFFLYSRLTVDKSRWQEGNVFSCSVMHEALHNHYTQKSLSLSLGK >L-chain variable region (SEQ ID NO: 184)
SYELTQPPSVSVSPGQTARITCSGGSGRYYYGWYQQKPGQAPVTVIYSSTHRPSGIPERFSGSNSGSTTTLTISGVQAEDEADYYCGTADS
SSYVFGGGTKLTVL >L-chain constant region (SEQ ID NO: 185)
GQPKAAPSVTLFPPSSEELQANKATLVCLISDFYPGAVTVAWKADSSPVKAGVETTTPSKQSNNKYAASSYLSLTPEQWKSHRSYSCQVTH
EGSTVEKTVAPTECS.

[Fig.27]
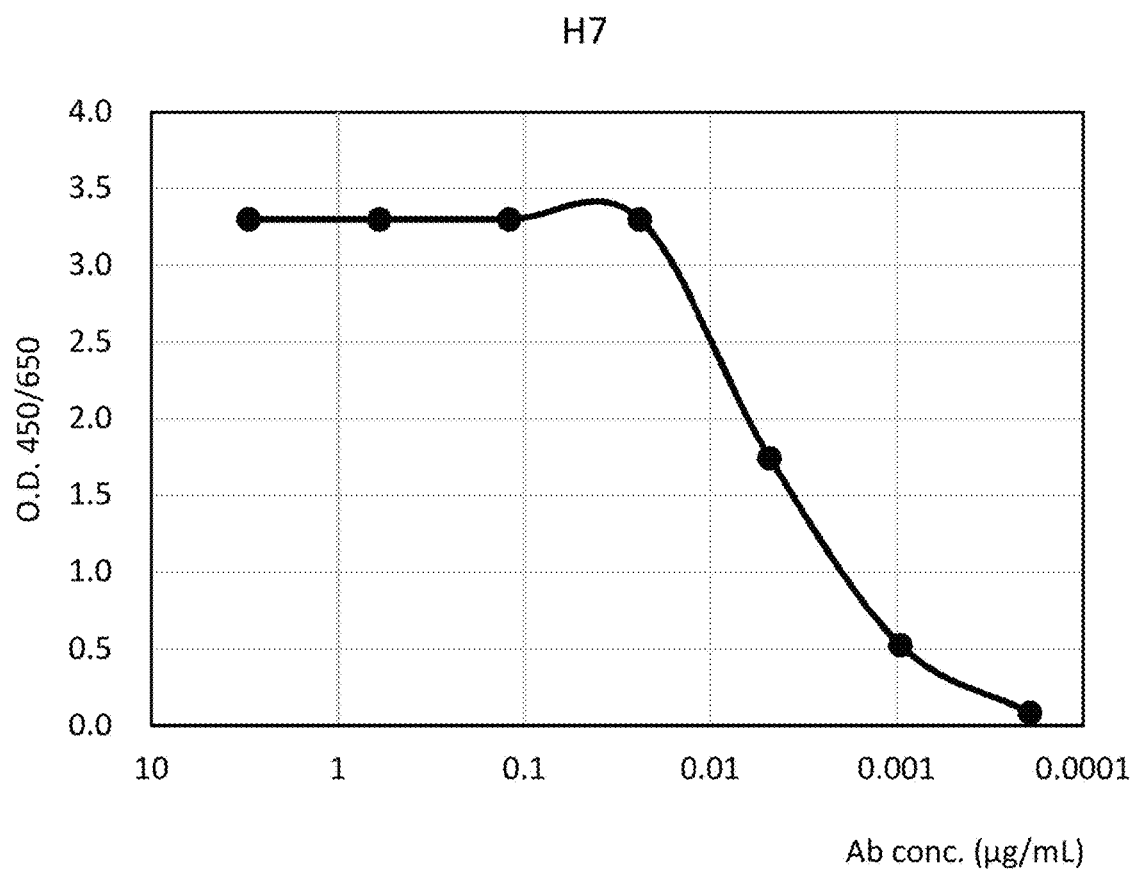
| Ab conc. (μg/mL) | H7 |
|---|---|
| 3 | 3.300 |
| 0.6 | 3.300 |
| 0.12 | 3.300 |
| 0.024 | 3.300 |
| 0.0048 | 1.741 |
| 0.00096 | 0.527 |
| 0 | 0.087 |

[Fig.28]
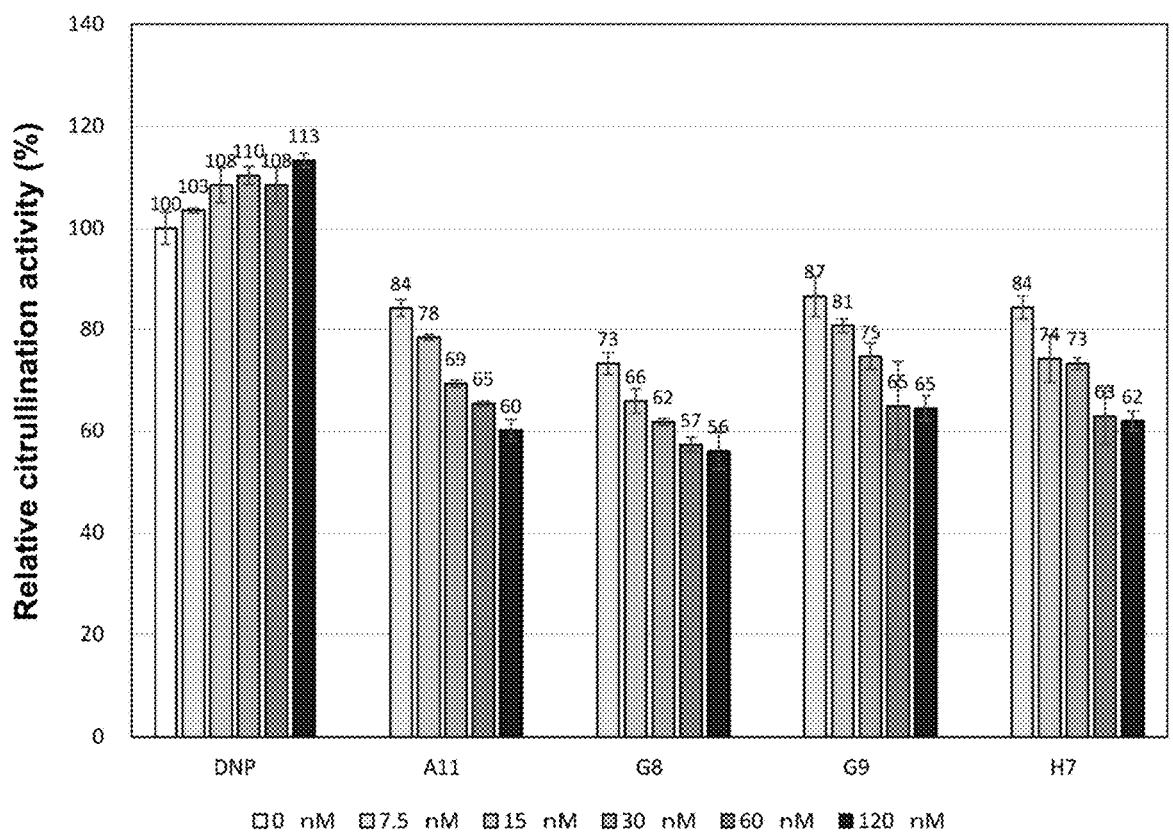

ANTI-PAD4 ANTIBODY

TECHNICAL FIELD

The present invention relates to novel anti-PAD4 antibodies.

BACKGROUND ART

Peptidylarginine deiminase 4 (PAD4) is known as an enzyme that participates in citrullination of an arginine in a protein. This citrullination involves a reaction such that an arginine, which is the most basic amino acid among amino acids constituting a protein, is converted to a neutral citrulline. This is important for the structure of the protein and the protein-mediated reaction.

The citrullination reportedly involves rheumatoid arthritis (RA). For example, in RA, a cyclic citrullinated peptide (CCP) is present as an antigen on a synovial membrane. Thus, an anti-CCP antibody is commercially available as an RA diagnostic agent.

There are some reports on PAD4 and RA. For example, Non-Patent Literature 1 reports the association between the onset of RA and a single nucleotide polymorphism of the PAD4 gene. In addition, Non-Patent Literature 2 reports use of an anti-PAD4 antibody for diagnosis of RA. Also, Patent Literature 1 describes that a mixture containing 4 different anti-PAD4 antibodies is administered to mice so as to suppress RA (see Example 2 of Patent Literature 1).

CITATION LIST

Patent Literature

[Patent Literature 1] WO2012/026309

Non-Patent Literature

[Non-Patent Literature 1] "Functional haplotypes of PADI4, encoding citrullinating enzyme peptidylarginine deiminase 4, are associated with rheumatoid arthritis.", Suzuki et al., Nat Genet. 2003 August; 34(4):395-402.

[Non-Patent Literature 2] "Two novel sandwich ELISAs identify PAD4 levels and PAD4 autoantibodies in patients with rheumatoid arthritis.", Ishigami et al., Mod Rheumatol. 2013 July; 23(4):794-803.

SUMMARY OF INVENTION

Technical Problem

Unfortunately, in Patent Literature 1, the mixture containing 4 different anti-PAD4 antibodies has to be used to suppress RA, and there has been room for improvement. In addition, there are no conventional anti-PAD4 antibodies effective in treating RA.

The present invention has been made in light of the above situations. The purpose of the present invention is to provide anti-PAD4 antibodies having excellent properties or to provide an excellent method for treatment of RA and so on.

Solution to Problem

The present inventors have found out that anti-PAD4 antibodies which specifically bind to an epitope containing positions 345, 347, and 348 of PAD4 exert surprisingly potent therapeutic effects on RA as described in the below-described Examples. In addition, these antibodies have stronger affinity toward PAD4 and higher citrullination activity-inhibitory function than the anti-PAD4 antibodies described in Patent Literature 1.

In addition, to our surprise, when a combination of an anti-PAD4 antibody and a TNFα inhibitor was administered to human rheumatoid arthritis model mice, a synergistic therapeutic benefit was observed.

Specifically, an aspect of the present invention provides an anti-PAD4 antibody which specifically binds to an epitope containing positions 345, 347, and 348 of PAD4. Use of this antibody enables treatment of RA.

In addition, another aspect of the present invention provides a polynucleotide or vector which encodes the above anti-PAD4 antibody. In addition, another aspect of the present invention provides a composition comprising the above anti-PAD4 antibody. In addition, another aspect of the present invention provides an inhibitor of citrullination activity of PAD4, comprising the above anti-PAD4 antibody. In addition, another aspect of the present invention provides a pharmaceutical composition for treatment of RA or arthritis, comprising the above anti-PAD4 antibody. In addition, another aspect of the present invention provides a process for producing an anti-PAD4 antibody, comprising the step of causing a cell containing the above polynucleotide or vector to proliferate.

In addition, in another aspect of the present invention, the above anti-PAD4 antibody may inhibit citrullination activity of PAD4. In addition, in another aspect of the present invention, the above anti-PAD4 antibody may have a KD (M) of $9.0 \times 10^{-9}$ or less. In addition, in another aspect of the present invention, the epitope of the above anti-PAD4 antibody may be identified by alanine scan in which a single amino acid is replaced. In addition, in another aspect of the present invention, the above anti-PAD4 antibody may be a monoclonal antibody. In addition, in another aspect of the present invention, the above anti-PAD4 antibody may be a humanized antibody. In addition, in another aspect of the present invention, the above anti-PAD4 antibody may be an antigen-binding fragment.

In addition, another aspect of the present invention provides a pharmaceutical composition comprising an anti-PAD4 antibody and a TNFα inhibitor. In addition, another aspect of the present invention provides an anti-PAD4 antibody-containing pharmaceutical composition used when the anti-PAD4 antibody and a TNFα inhibitor are used in combination. In addition, another aspect of the present invention provides a TNFα inhibitor-containing pharmaceutical composition used when an anti-PAD4 antibody and the TNFα inhibitor are used in combination. In addition, another aspect of the present invention provides a treatment kit comprising an anti-PAD4 antibody and a TNFα inhibitor.

In addition, another aspect of the present invention provides the above pharmaceutical composition as a pharmaceutical composition for treatment of RA or arthritis. In addition, in another aspect of the present invention, the above anti-PAD4 antibody may be a humanized antibody. In addition, another aspect of the present invention provides the above treatment kit as a kit for treatment of RA or arthritis.

Advantageous Effects of Invention

The present invention provides anti-PAD4 antibodies having excellent properties or an excellent method for treatment of RA or arthritis and so on.

BRIEF DESCRIPTION OF DRAWINGS

FIG. 4 is a plot showing the results of affinity assay.
FIG. 5 is a diagram illustrating the results of alanine scan.
FIG. 6 is a graph showing the results of evaluating citrullination activity-inhibitory function.
FIG. 8 provides an outline of experimental conditions during drug efficacy evaluation.
FIG. 10 is a graph showing the results of evaluating an arthritis score.
FIG. 11 is a graph showing the results of evaluating the titer of an anti-CCP antibody.
FIGS. 12A-12F are pictures showing the results of histological analysis.
FIG. 13 provides an outline of experimental conditions during drug efficacy evaluation.
FIG. 15 is a graph showing the results of evaluating an arthritis score.
FIG. 16 shows the amino acid sequence of the constant region of each of the H-chain (IgG1) and the L-chain (κ) of a humanized antibody of Example 6.
FIG. 17 shows the sequences of variable regions of a humanized antibody G8.
FIG. 18 shows the sequences of variable regions of a humanized antibody H7 (the H-chain sequence is the same as of G8).
FIG. 19 shows the complete amino acid sequence of an A11- or G8-derived humanized antibody.
FIG. 20 shows the complete amino acid sequence of an G9- or H7-derived humanized antibody.
FIG. 21 is a set of tables showing the results of ELISA.
FIGS. 22A-22L are graphs showing the results of ELISA.
FIGS. 23A-23L are graphs showing the results of ELISA.
FIG. 25 shows DNA sequences used for construction of a humanized anti-PAD4 antibody (IgG4λ).
FIG. 26 shows the amino acid sequences of the anti-PAD4 antibody (IgG4λ) of Example 6.
FIG. 27 is a table and a graph showing the results of ELISA.
FIG. 28 is a graph showing the results of evaluating citrullination activity-inhibitory function.

DESCRIPTION OF EMBODIMENTS

Figure 1A:
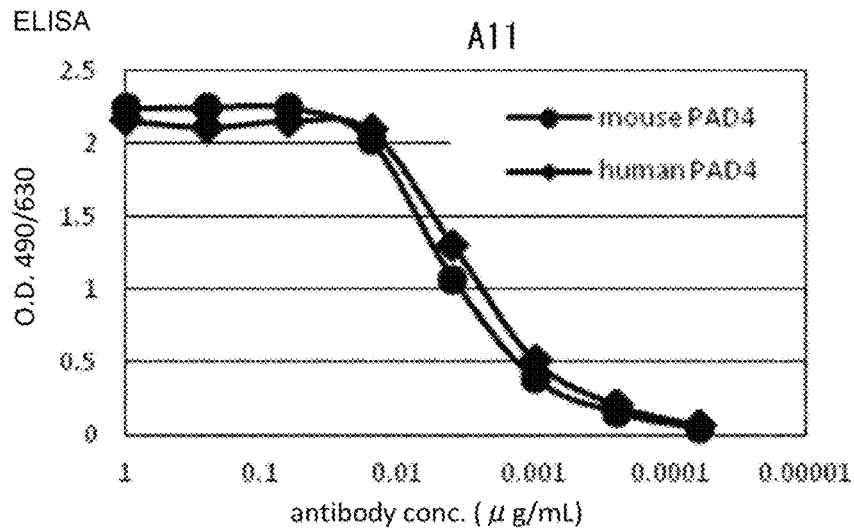
FIGS. 1A-1C are graphs showing the results of ELISA.

Hereinafter, embodiments of the present invention will be described in detail. Note that descriptions are not repeated so as to avoid redundancy.

An embodiment of the present invention provides a novel anti-PAD4 antibody. This antibody is, for example, an anti-PAD4 antibody that specifically binds to an epitope containing positions 345, 347, and 348 of PAD4. Use of this antibody enables treatment of rheumatoid arthritis (RA) or arthritis. This treatment protocol is excellent in view of safety because use of an antibody gives a small side effect.

PAD4 is known as an enzyme that participates in citrullination of an arginine in a protein. Detailed information on the amino acid sequence of PAD4, etc., can be seen in, for example, the website of NCBI (National Center for Biotechnology Information) or HGNC (HUGO Gene Nomenclature Committee). Examples of the accession number of PAD4 deposited in NCBI includes NP_036519.2. Examples of the amino acid sequence of PAD4 include SEQ ID NO: 2. The source organisms of PAD4 are not limited as long as the PAD4 has such activity. Asp, Trp, and Met are normally located at the positions 345, 347, and 348 of PAD4, respectively.

As used herein, the "anti-PAD4 antibodies" include an antibody that can bind to PAD4. Examples of a process for producing this anti-PAD4 antibody may include, but are not particularly limited to, a process in which a mammal or bird is immunized with PAD4. The anti-PAD4 antibody which specifically binds to an epitope containing positions 345, 347, and 348 of PAD4 may be obtained by selecting, for example, an anti-PAD4 antibody that exhibits binding to wild-type PAD4 but exhibits no binding to a PAD4 mutant in which an amino acid at the position 345, 347, or 348 is replaced by alanine.

An anti-PAD4 antibody according to an embodiment of the present invention may inhibit the citrullination activity of PAD4.

An anti-PAD4 antibody according to an embodiment of the present invention may be a monoclonal antibody. The monoclonal antibody can act on PAD4 more efficiently than a polyclonal antibody counterpart. From the viewpoint of efficiently producing an anti-PAD4 monoclonal antibody having a desired effect, a chicken is preferably immunized with PAD4. Unless otherwise indicated, examples of PAD4 used as an antigen include full-length PAD4 or peptide fragments of PAD4.

The antibody class of an anti-PAD4 antibody according to an embodiment of the present invention is not particularly limited. Examples of the class may include IgM, IgD, IgG, IgA, IgE, and IgY. In addition, examples of the antibody subclass may include, but are not particularly limited to, IgG1, IgG2, IgG3, IgG4, IgA1, and IgA2.

An anti-PAD4 antibody according to an embodiment of the present invention may be an antibody fragment having PAD4-binding activity (hereinafter, sometimes referred to as an "antigen-binding fragment"). In this case, effects involving increased stability or antibody production efficiency are exerted.

An anti-PAD4 antibody according to an embodiment of the present invention may be a fusion protein. This fusion protein may be produced by attaching a polypeptide or oligopeptide to the N-terminal or C-terminal end of the anti-PAD4 antibody. As used herein, the oligopeptide may be a His-tag. In addition, this fusion protein may be created by fusing the anti-PAD4 antibody and a portion of the sequence of a mouse, human, or chicken antibody. Such a fusion protein can be included as a form of the anti-PAD4 antibody according to this embodiment.

An anti-PAD4 antibody according to an embodiment of the present invention may be obtained after a step of immunizing a chicken with PAD4. The antibody may be an antibody having a CDR set of the antibody obtained after a step of immunizing a chicken with PAD4. The CDR set is a set containing heavy chain CDRs 1, 2, and 3 and light chain CDRs 1, 2, and 3.

An anti-PAD4 antibody according to an embodiment of the present invention may have a KD (M) of, for example, $9.9 \times 10^{-9}$, $9.5 \times 10^{-9}$, $9.0 \times 10^{-9}$, $8.5 \times 10^{-9}$, $8.0 \times 10^{-9}$, $7.0 \times 10^{-9}$, $6.0 \times 10^{-9}$, $5.0 \times 10^{-9}$, $4.0 \times 10^{-9}$, $3.0 \times 10^{-9}$, $2.0 \times 10^{-9}$, or less. The number may be between any two of the above values. From the viewpoint of enhancing RA treatment effects, the KD (M) is preferably $9.0 \times 10^{-9}$ or less.

An anti-PAD4 antibody according to an embodiment of the present invention may bind to wild-type PAD4 or a mutant of PAD4. The term "mutant" includes being responsible for a DNA sequence variation, like SNPs, among individuals. Homology between the amino acid sequence of wild-type PAD4 or a mutant of PAD4 and the amino acid sequence set forth in SEQ ID NO: 2 is preferably 80% or higher, more preferably 90% or higher, still more preferably 95% or higher, and still more preferably 98% or higher.

An anti-PAD4 antibody according to an embodiment of the present invention may be an antibody which can bind to wild-type PAD4 but cannot bind to a PAD4 mutant in which an amino acid at position 345, 347, or 348 is replaced by Ala. The wording "cannot bind to" refers to there being no substantial binding.

An anti-PAD4 antibody according to an embodiment of the present invention may be an antibody obtained by a production process including: selecting an antibody which can significantly react with wild-type PAD4; or selecting an antibody which cannot bind to a PAD4 mutant in which an amino acid at position 345, 347, or 348 is replaced by Ala.

Regarding an anti-PAD4 antibody according to an embodiment of the present invention, the binding of the antibody to a PAD4 mutant in which an amino acid at position 345, 347, or 348 is replaced by Ala may be 50% or less than that of an anti-PAD4 polyclonal antibody. The term "50% or less" may mean, for example, 50, 45, 40, 35, 30, 25, 20, 15, 10, 5, 1, or 0%. The number may be between any two of the above values. The binding may be evaluated by, for example, ELISA or Biacore. As used herein, the term "anti-PAD4 polyclonal antibody" includes, for example, antiserum. The term "binding" or "reactivity" includes affinity.

An anti-PAD4 antibody according to an embodiment of the present invention may specifically bind to positions 345, 347, and 348 of PAD4. This antibody may bind to another amino acid residue within the epitope as long as the antibody can specifically bind to the positions 345, 347, and 348 of PAD4. Examples of another amino acid residue within the epitope may include an amino acid residue at position 344 of PAD4. An antibody which specifically binds to a specific site may be an antibody which recognize the specific site.

An epitope to which an anti-PAD4 antibody according to an embodiment of the present invention binds may contain, in addition to the amino acid residues at positions 345, 347, and 348 of PAD4, an amino acid residue(s) other than those amino acid residues at positions 345, 347, and 348. For example, the above epitope may contain an amino acid residue at position 344. In addition, this epitope may not contain an amino acid at position 340, 341, 342, 343, 344, 346, 349, 350, 351, 352, 353, 354, 355, or 356 of PAD4.

An anti-PAD4 antibody according to an embodiment of the present invention may specifically bind to an epitope containing amino acids at positions 6, 8, and 9 of a peptide, the amino acid sequence of which is set forth in SEQ ID NO: 1.

An anti-PAD4 antibody according to an embodiment of the present invention may be an antibody which can bind to a peptide, the amino acid sequence of which is set forth in SEQ ID NO: 1, but cannot bind to a peptide, the amino acid sequence of which is set forth in SEQ ID NO: 32, 34, or 35.

Regarding an anti-PAD4 antibody according to an embodiment of the present invention, the binding of the antibody to a peptide, the amino acid sequence of which is set forth in SEQ ID NO: 32, 34, or 35, may be 50% or less than that of an anti-PAD4 polyclonal antibody. The term "50% or less" may mean, for example, 50, 45, 40, 35, 30, 25, 20, 15, 10, 5, 1, or 0%. The number may be between any two of the above values. The binding may be evaluated by, for example, ELISA or Biacore.

An anti-PAD4 antibody according to an embodiment of the present invention may specifically bind to positions 6, 8, and 9 of a peptide, the amino acid sequence of which is set forth in SEQ ID NO: 1. This antibody may bind to another amino acid residue within the epitope as long as the antibody can specifically bind to the positions 6, 8, and 9 of a peptide, the amino acid sequence of which is set forth in SEQ ID NO: 1. Examples of another amino acid residue within the epitope may include an amino acid residue at position 5 of a peptide, the amino acid sequence of which is set forth in SEQ ID NO: 1.

An epitope to which an anti-PAD4 antibody according to an embodiment of the present invention binds may contain, in addition to the amino acid residues at positions 6, 8, and 9 of a peptide, the amino acid sequence of which is set forth in SEQ ID NO: 1, an amino acid residue at position 5. In addition, this epitope may not contain an amino acid at position 1, 2, 3, 4, 5, 7, 10, 11, 12, 13, 14, 15, 16, or 17 of a peptide, the amino acid sequence of which is set forth in SEQ ID NO: 1.

An epitope to which an anti-PAD4 antibody according to an embodiment of the present invention binds may be an epitope identified by, for example, alanine scan. As used herein, the term "alanine scan" refers to a technique in which an amino acid of a protein, for example, is replaced by alanine and characteristics of an antibody binding to the protein are examined. The epitope identified by alanine scan may be an epitope that can be determined after a step (i) of replacing a single amino acid residue of an antigen by Ala to create an Ala mutant; a step (ii) of measuring the affinity of a test antibody toward the Ala mutant; and/or a step (iii) of evaluating, as an epitope, an original amino acid residue before the Ala replacement with respect to the Ala mutant with which the test antibody is not significantly reacted. The above step (i) may include a step of replacing a plurality of single amino acid residues of the antigen by Ala to create a plurality of Ala mutants. The epitope evaluation method may include a step (iv) of measuring the affinity of an anti-PAD4 polyclonal antibody toward each Ala mutant. The epitope evaluation method may include a step (v) of determining that when the affinity of the test antibody toward the Ala mutant is 50% or less than the affinity of an anti-PAD4 polyclonal antibody toward the Ala mutant, the test antibody does not exhibit significant reactivity. The term "50% or less" may mean 50, 45, 40, 35, 30, 25, 20, 15, 10, 5, 1% or less, or 0%. The number may be between any two of the above values. The alanine scan may be executed by replacing a single amino acid. An antigen used for the alanine scan may be PAD4 or a peptide fragment thereof. The affinity may be evaluated by, for example, ELISA or Biacore.

As used herein, the term "antibody" refers to a molecule which can specifically bind to a specific epitope localized on an antigen, and also refers to a population of the molecule. In addition, the term "antibody" may include polyclonal and monoclonal antibodies. In addition, antibodies have a wide variety of forms. Examples may include at least one form selected from the group consisting of a full-length antibody (an antibody having Fab regions and an Fc region), an Fv antibody, a Fab antibody, a F(ab')$_2$ antibody, a Fab' antibody, a diabody, a single-chain antibody (e.g., an scFv), a dsFv, a multivalent antibody (e.g., a divalent antibody), an antigen-binding peptide or polypeptide, a chimeric antibody, a mouse antibody, a chicken antibody, a humanized antibody, a human antibody, and an equivalent thereof. Also, the antibodies may be or may not be modified. With regard to the modified antibodies, various molecules such as polyethylene glycol may be conjugated to an antibody. The modified antibodies may be obtained by subjecting an antibody to chemical modification using a known method. The amino acid sequence, class, or subclass of the antibody may be those derived from, for example, a human, a non-human mammal (e.g., a mouse, a rat, a rabbit, a cow, a monkey), or a bird (e.g., a chicken). In addition, examples of the antibody include an isolated antibody, a purified antibody, and a recombinant antibody. Also, the antibody may be used, for example, in vitro or in vivo.

As used herein, a "polyclonal antibody" can be produced by immunizing, for example, a mammal (e.g., a rat, mouse, guinea pig, rabbit, cow, monkey) or a bird (e.g., a chicken) with an immunogen containing an antigen of interest. The immunization may require co-injection of one or more immunizing agents and an adjuvant. The adjuvant may be used to increase an immune response. The adjuvant may include Freund's adjuvant (complete or incomplete), a mineral gel (e.g., aluminum hydroxide), and/or a surfactant (e.g., lysolecithin). An immunization protocol is publicly known in the art. Any method for inducing an immune response in a selected host organism may be performed depending on the selected host species ("Protein Experiment Handbook", YODOSHA CO., LTD. (2003), 86-91).

As used herein, the term "monoclonal antibody" includes antibodies obtained when individual antibodies constituting a population react with substantially the same epitope. Alternatively, the monoclonal antibody may be obtained when individual antibodies constituting a population are substantially the same (naturally occurring mutations are permitted). Monoclonal antibodies are highly specific and differ from a regular polyclonal antibody, which typically contains different antibodies binding to different epitopes. A process for producing a monoclonal antibody has no particular limitation. For example, the monoclonal antibody may be produced by a method similar to the hybridoma method disclosed in "Köhler G and Milstein C, Nature, 1975, Aug. 7, 256 (5517), 495-497". Alternatively, the monoclonal antibody may be produced by a method similar to the recombinant technology disclosed in U.S. Pat. No. 4,816,567. In addition, the monoclonal antibody may be isolated from a phage antibody library by a method similar to the technology described in "Clackson et al., Nature, 1991, Aug. 15, 352 (6336), 624-628" or "Marks et al., J Mol Biol., 1991, Dec. 5, 222(3), 581-597". Furthermore, the antibody may be generated by a procedure disclosed in "Protein Experiment Handbook, YODOSHA CO., LTD., (2003), 92-96".

As used herein, an "Fv antibody" is an antibody fragment that contains an antigen recognition site. The Fv consists of a dimer between one heavy chain variable domain and one light chain variable domain, which domains are coupled by noncovalent bonds. Using this structure, three CDRs of the respective variable domains can interact with one another to form an antigen binding site on the surface of the VH-VL dimer.

As used herein, a "Fab antibody" is an antibody fragment produced by digesting, for example, an antibody containing Fab regions and an Fc region by a protease papain, the fragment having the N-terminal half of the H chain and the whole L chain linked by a disulfide bond. For example, a Fab can be obtained by digesting, by a protease papain, an anti-PAD4 antibody containing Fab regions and an Fc region according to an embodiment of the present invention.

As used herein, a "F(ab')$_2$ antibody" is an antibody fragment containing two Fab regions derived from a fragment as produced by digesting, for example, an antibody containing Fab regions and an Fc region by a protease pepsin. For example, a F(ab')$_2$ can be obtained by digesting, by a protease pepsin, an anti-PAD4 antibody containing Fab regions and an Fc region according to an embodiment of the present invention. Also, the F(ab')$_2$ can be produced by linking, for example, the following Fab's via a thioether bond or a disulfide bond.

As used herein, a "Fab' antibody" is an antibody fragment as produced, for example, by cleaving the disulfide bond in the hinge region of a F(ab')$_2$ fragment. The Fab' can be produced by treating the F(ab')$_2$ with a reducing agent such as dithiothreitol.

As used herein, an "scFv antibody" is an antibody fragment in which VH and VL are linked via a suitable peptide linker. The scFv antibody can be produced by obtaining cDNAs encoding the VH and VL of an anti-PAD4 antibody according to the above embodiment of the present invention, constructing a polynucleotide encoding a VH-peptide linker-VL fragment, cloning the polynucleotide into a vector, and using cells expressing the vector to produce an scFv.

As used herein, a "diabody" is an antibody fragment having a divalent antigen-binding activity. Both two antigen-binding activities can be identical, or one of them can be a distinct antigen-binding activity. The diabody can be produced by constructing a polynucleotide containing a nucleotide sequence encoding, for example, scFvs linked using a peptide linker having an amino acid sequence of 8 residues or less, cloning the resulting polynucleotide into a vector, and using cells expressing the vector to produce a diabody.

As used herein, a "dsFv" is an antibody fragment in which a VH polypeptide containing a cysteine residue and a VL polypeptide containing a cysteine residue are linked via a disulfide bond between the above cysteine residues. The amino acid residue substituted by the cysteine residue can be selected based on an antibody conformation prediction in accordance with a procedure indicated by Reiter et al. (Reiter et al., Protein Eng., 1994, May, 7(5), 697-704).

As used herein, an "antigen-binding peptide or polypeptide" is an antibody fragment containing the VH and/or VL of an antibody or CDRs 1, 2, and/or 3 thereof. A plurality of peptides containing a CDR(s) can be linked directly or indirectly via a suitable peptide linker.

A process for producing the above Fv antibody, Fab antibody, F(ab')$_2$ antibody, Fab' antibody, scFv antibody, diabody, dsFv antibody, and antigen-binding peptide or polypeptide (hereinafter, sometimes referred to as "Fv antibody etc.") is not particularly limited. For example, the Fv antibody, etc., can be produced by cloning a DNA encoding a region (such as an Fv antibody etc.) of an anti-PAD4 antibody according to an embodiment of the present invention into an expression vector and by using cells expressing the vector for their production. In addition, a chemical synthesis process such as an Fmoc (fluorenylmethyloxycarbonyl) process and a tBOC (t-butyloxycarbonyl) process may be used for their production. Note that as used herein, an anti-binding fragment may include at least one of the above Fv antibody, etc.

As used herein, a "chimeric antibody" can be produced, for example, by linking variable regions of an antibody derived from one species to constant regions of an antibody derived from another species, and can be easily constructed using gene recombinant technology. Examples include a mouse-human chimeric antibody, a chicken-human chimeric antibody, and a chicken-mouse chimeric antibody. For example, a mouse-human chimeric antibody can be produced by a process disclosed in "Roguska et al., Proc Natl Acad Sci USA., 1994, Feb. 1, 91(3), 969-973". For example, a basic procedure for producing a mouse-human chimeric antibody includes: isolating a mouse leader sequence and a variable region sequence present in a cloned cDNA; and linking these sequences to a sequence encoding a constant region of a human antibody, the sequence being present in a mammalian expression vector. Alternatively, a mouse leader sequence and a variable region sequence present in a cloned cDNA may be first linked to a sequence encoding a constant region of a human antibody and the resulting sequence is then ligated into a mammalian expression vector. A constant region fragment of the human antibody can be a constant region of the H chain or a constant region of the L chain of any human antibody. Examples of the constant region of the human H chain can include Cγ1, Cγ2, Cγ3 and Cγ4. Examples of the constant region of the L chain can include CΔ and Cκ.

As used herein, a "humanized antibody" has, for example, one or more CDRs derived from a non-human species, human-immunoglobulin-derived framework regions (FRs), and human-immunoglobulin-derived constant regions. The humanized antibody binds to a desired antigen. An antibody can be humanized by using various techniques known in the art (Almagro et al., Front Biosci., 2008, Jan. 1, 13, 1619-1633). Examples of the techniques can include CDR grafting (Ozaki et al., Blood, 1999, Jun. 1, 93(11), 3922-3930), re-surfacing (Roguska et al., Proc Natl Acad Sci USA., 1994, Feb. 1, 91(3), 969-973), and FR shuffling (Damschroder et al., Mol Immunol., 2007, April, 44(11), 3049-3060, Epub 2007, Jan. 22). In order to modify or improve the antigen binding, amino acid residues in the human FR regions may be substituted by residues corresponding to those of the CDR-donor antibody. This FR substitution can be implemented using a procedure well-known in the art (Riechmann et al., Nature, 1988, Mar. 24; 332(6162): 323-327). For example, the interaction between CDRs and FRs may be simulated to identify FR residues that are critical in antigen binding. Alternatively, their sequences may be compared to identify FR residues that are abnormal at a specific position. Note that an antibody is preferably humanized by the method described in Nishibori et al., Mol Immunol. 2006 February; 43(6):634-42.

As used herein, a "human antibody" has, for example, a heavy chain variable region and a constant region and a light chain variable region and a constant region, all of which are derived from genes encoding a human immunoglobulin. Examples of a basic method for generating a human antibody include a method using a human-antibody-producing transgenic mouse, phage display, and the like. The method using a human-antibody-producing transgenic mouse includes: introducing a functional human Ig gene into an endogenous-Ig-knockout mouse; and producing, instead of mouse antibodies, human antibodies having versatile antigen-binding abilities. Further, if this mouse is immunized, a human monoclonal antibody can be obtained using a conventional hybridoma procedure. For example, a human antibody can be prepared using the method disclosed in "Lonberg et al., Int Rev Immunol., 1995, 13(1), 65-93". The phage display is typically a system in which an exogenous gene is made to be expressed as a fusion protein at an N-terminal portion of a coat protein (e.g., g3p, g10p) of a filamentous phage such as M13 or T7, an *E. coli* virus, without losing infectivity of the phage. For example, a human antibody can be generated using the method disclosed in "Vaughan et al., Nat Biotechnol., 1996, Mar., 14(3), 309-314".

As used herein, a "heavy chain" is typically a main component of a full-length antibody. The heavy chain is usually linked to a light chain via a disulfide bond and noncovalent bonds. The N-terminal domain of the heavy chain has what is called a variable region (VH), the amino acid sequence of which is not the same even in the same class of antibodies derived from the same species. Generally speaking, the VH is known to contribute largely to specificity and affinity toward an antigen. An article "Reiter et al., J Mol Biol., 1999, Jul. 16; 290(3): 685-98", for example, has reported that a molecule containing only a VH was able to bind to an antigen with high specificity and affinity. Further, an article "Wolfson W, Chem Biol., 2006, Dec.; 13(12): 1243-1244" has reported that among camel antibodies, an antibody having only a heavy chain but not a light chain is present.

As used herein, "CDRs (complementarity determining regions)" are antibody regions which actually contact an antigen to form a binding site. Generally speaking, the CDRs are localized in the Fv (variable regions including a heavy chain variable region (VH) and a light chain variable region (VL)) of an antibody. Also, the CDRs, in general, include CDR1, CDR2, and CDR3 having about 5 to 30 amino acid residues. Here, the heavy chain CDRs, in particular, are known to contribute to binding of an antibody to an antigen. Among the CDRs, CDR3 is known to contribute most to the binding of an antibody to an antigen. An article "Willy et al., Biochemical and Biophysical Research Communications Volume 356, Issue 1, 27, April 2007, Pages 124-128", for example, discloses that modification of the heavy chain CDR3 increased the binding ability of an antibody. Fv regions other than the CDRs are called framework regions (FR). The FR regions include FR1, FR2, FR3, and FR4 and are relatively well conserved among antibodies (Kabat et al., "Sequence of Proteins of Immunological Interest" US Dept. Health and Human Services, 1983).

Several reports have disclosed CDR definitions and methods for determining a CDR position. For example, Kabat's definition (Sequences of Proteins of Immunological Interest, 5th ed., Public Health Service, National Institutes of Health, Bethesda, Md. (1991)) or Chothia's definition (Chothia et al., J. Mol. Biol., 1987; 196: 901-917) may be used. As used herein, the Kabat's definition is used as a preferable definition. The definition, however, is not limited to the above. In addition, the CDRs may be determined by considering both the Kabat's definition and the Chothia's definition. For example, a portion in which the CDRs defined by each definition overlap one another may be determined as a CDR. Alternatively, a portion containing both the CDRs defined by each definition may be determined as a CDR. Specific examples of such a method include Martin's method (Proc. Natl. Acad. Sci. USA, 1989; 86: 9268-9272) using Oxford Molecular's AbM antibody modeling software. The Martin's method involves a proposal in which the Kabat's definition and the Chothia's definition are compromised.

According to an embodiment of the present invention, at least one anti-PAD4 antibody is selected from the group consisting of: (a) an antibody containing the amino acid sequences of heavy chain CDRs 1 to 3 and light chain CDRs 1 to 3 represented by respective SEQ ID NOs: 50 to 55; (b) an antibody containing the amino acid sequences of heavy chain CDRs 1 to 3 and light chain CDRs 1 to 3 represented by respective SEQ ID NOs: 56 to 61; (c) an antibody containing the amino acid sequences of heavy chain CDRs 1 to 3 and light chain CDRs 1 to 3 represented by respective SEQ ID NOs: 62 to 67; (d) an antibody containing the amino acid sequences of heavy chain CDRs 1 to 3 and light chain CDRs 1 to 3 represented by respective SEQ ID NOs: 68 to 73; (e) an antibody containing the amino acid sequences of heavy chain CDRs 1 to 3 and light chain CDRs 1 to 3 represented by respective SEQ ID NOs: 74 to 79; and (f) an antibody containing the amino acid sequences of heavy chain CDRs 1 to 3 and light chain CDRs 1 to 3 represented by respective SEQ ID NOs: 80 to 85. Use of each antibody enables treatment of RA or arthritis. In another embodiment of the present invention, an anti-PAD4 antibody contains at least one set selected from amino acid sequence sets of the heavy chain CDRs 1 to 3 and the light chain CDRs 1 to 3 listed above. Here, the above term "respective" has the same meaning as "in sequence".

Note that the amino acid sequences set forth in the above (a) to (f) correspond to the respective CDR amino acid sequences of antibodies A11, E9, G6, G8, G9, and H7 as described in the following Examples. Specifically, the amino acid sequences of heavy chain CDRs 1, 2, and 3 and light chain CDRs 1, 2, and 3 of A11 are amino acid sequences represented by SYGMG (SEQ ID NO: 50), AIRNDGSWTGYGAAVKG (SEQ ID NO: 51), TTGSRGGSIDA (SEQ ID NO: 52), SGGGRYYYG (SEQ ID NO: 53), ANDKRPS (SEQ ID NO: 54), and GSAETSSYV (SEQ ID NO: 55), respectively. In addition, the amino acid sequences of heavy chain CDRs 1, 2, and 3 and light chain CDRs 1, 2, and 3 of E9 are amino acid sequences represented by SYGMG (SEQ ID NO: 56), AIRNDGSWTGYGSAVKG (SEQ ID NO: 57), TSGSSGGSVDA (SEQ ID NO: 58), SGGGRYYYG (SEQ ID NO: 59), ANDKRPS (SEQ ID NO: 60), and GSAETSSYV (SEQ ID NO: 61), respectively. In addition, the amino acid sequences of heavy chain CDRs 1, 2, and 3 and light chain CDRs 1, 2, and 3 of G6 are amino acid sequences represented by SYGME (SEQ ID NO: 62), AIRNDGSWTGYGAAVKG (SEQ ID NO: 63), TTGSSGGSIDA (SEQ ID NO: 64), SGGGNYYYG (SEQ ID NO: 65), ANDKRPS (SEQ ID NO: 66), and GTADTGKYV (SEQ ID NO: 67), respectively. In addition, the amino acid sequences of heavy chain CDRs 1, 2, and 3 and light chain CDRs 1, 2, and 3 of G8 are amino acid sequences represented by TYAMG (SEQ ID NO: 68), AIRNDGSWTGYGAAVKG (SEQ ID NO: 69), YTGSSGGSIGA (SEQ ID NO: 70), SGGNRNYYYG (SEQ ID NO: 71), ANDKRPS (SEQ ID NO: 72), and GTADTGKYV (SEQ ID NO: 73), respectively. In addition, the amino acid sequences of heavy chain CDRs 1, 2, and 3 and light chain CDRs 1, 2, and 3 of G9 are amino acid sequences represented by TYAMG (SEQ ID NO: 74), AIRNDGSWTGYGAAVKG (SEQ ID NO: 75), YTGSSGGSIGA (SEQ ID NO: 76), SGGGRYYYG (SEQ ID NO: 77), ANDKRPS (SEQ ID NO: 78), and GSAETSSYV (SEQ ID NO: 79), respectively. In addition, the amino acid sequences of heavy chain CDRs 1, 2, and 3 and light chain CDRs 1, 2, and 3 of H7 are amino acid sequences represented by TYAMG (SEQ ID NO: 80), AIRNDGSWTGYGAAVKG (SEQ ID NO: 81), YTGSSGGSIGA (SEQ ID NO: 82), SGGSGRYYYG (SEQ ID NO: 83), SSTHRPS (SEQ ID NO: 84), and GTADSSSYV (SEQ ID NO: 85)), respectively.

The above antibody (a) may contain the amino acid sequences of heavy chain FRs 1 to 4 and light chain FRs 1 to 4 represented by respective SEQ ID NOs: 86 to 93. The above antibody (b) may contain the amino acid sequences of heavy chain FRs 1 to 4 and light chain FRs 1 to 4 represented by respective SEQ ID NOs: 94 to 101. The above antibody (c) may contain the amino acid sequences of heavy chain FRs 1 to 4 and light chain FRs 1 to 4 represented by respective SEQ ID NOs: 102 to 109. The above antibody (d) may contain the amino acid sequences of heavy chain FRs 1 to 4 and light chain FRs 1 to 4 represented by respective SEQ ID NOs: 110 to 117. The above antibody (e) may contain the amino acid sequences of heavy chain FRs 1 to 4 and light chain FRs 1 to 4 represented by respective SEQ ID NOs: 118 to 125. The above antibody (f) may contain the amino acid sequences of heavy chain FRs 1 to 4 and light chain FRs 1 to 4 represented by respective SEQ ID NOs: 126 to 133. Note that these FR amino acid sequences correspond to the respective FR amino acid sequences of antibodies A11, E9, G6, G8, G9, and H7 as described in the following Examples. In another embodiment of the present invention, an anti-PAD4 antibody contains at least one set selected from amino acid sequence sets of the heavy chain FRs 1 to 4 and the light chain FRs 1 to 4 listed above.

As long as the above antibody (a) exerts desired effects, its heavy chain CDR3 may contain the amino acid sequence set forth in SEQ ID NO: 70 instead of SEQ ID NO: 52; and its light chain CDR3 may contain the amino acid sequence set forth in SEQ ID NO: 67 instead of SEQ ID NO: 55. As long as the above antibody (b) exerts desired effects, its heavy chain CDR2 may contain the amino acid sequence set forth in SEQ ID NO: 51 instead of SEQ ID NO: 57; its heavy chain CDR3 may contain the amino acid sequence set forth in SEQ ID NO: 70 instead of SEQ ID NO: 58; and its light chain CDR3 may contain the amino acid sequence set forth in SEQ ID NO: 67 instead of SEQ ID NO: 61. As long as the above antibody (c) exerts desired effects, its heavy chain CDR1 may contain the amino acid sequence set forth in SEQ ID NO: 50 instead of SEQ ID NO: 62; its heavy chain CDR3 may contain the amino acid sequence set forth in SEQ ID NO: 70 instead of SEQ ID NO: 64; its light chain CDR1 may contain the amino acid sequence set forth in SEQ ID NO: 53 instead of SEQ ID NO: 65; and its light chain CDR3 may contain the amino acid sequence set forth in SEQ ID NO: 55 instead of SEQ ID NO: 67. As long as the above antibody (d) exerts desired effects, its light chain CDR1 may contain the amino acid sequence set forth in SEQ ID NO: 53 instead of SEQ ID NO: 71; and its light chain CDR3 may contain the amino acid sequence set forth in SEQ ID NO: 55 instead of SEQ ID NO: 73. As long as the above antibody (e) exerts desired effects, its light chain CDR3 may contain the amino acid sequence set forth in SEQ ID NO: 67 instead of SEQ ID NO: 79. As long as the above antibody (f) exerts desired effects, its light chain CDR1 may contain the amino acid sequence set forth in SEQ ID NO: 53 instead of SEQ ID NO: 83; its light chain CDR2 may contain the amino acid sequence set forth in SEQ ID NO: 54 instead of SEQ ID NO: 84; and its light chain CDR3 may contain the amino acid sequence set forth in SEQ ID NO: 55 or 67 instead of SEQ ID NO: 85.

As long as an anti-PAD4 antibody according to an embodiment of the present invention exerts desired effects, its heavy chain CDR1 may contain the amino acid sequence set forth in SEQ ID NO: 50, 56, 62, 68, 74, or 80; its heavy chain CDR2 may contain the amino acid sequence set forth in SEQ ID NO: 51, 57, 63, 69, 75, or 81; its heavy chain CDR3 may contain the amino acid sequence set forth in SEQ ID NO: 52, 58, 64, 70, 76, or 82; its light chain CDR1 may contain the amino acid sequence set forth in SEQ ID NO: 53, 59, 65, 71, 77, or 83; its light chain CDR2 may contain the amino acid sequence set forth in SEQ ID NO: 54, 60, 66, 72, 78, or 84; and its light chain CDR3 may contain the amino acid sequence set forth in SEQ ID NO: 55, 61, 67, 73, 79, or 85.

An anti-PAD4 antibody according to an embodiment of the present invention may have a form of scFv. In this case, a linker may be provided between a heavy chain and a light chain. Representative examples of the linker include, but are not limited to, a sequence containing 0 to 5 amino acids consisting of G and P. The linker may have, for example, the amino acid sequence set forth in SEQ ID NO: 134. The linker is dispensable and may not be present.

An anti-PAD4 antibody according to an embodiment of the present invention may be at least one anti-PAD4 antibody selected from the group consisting of: an antibody containing the amino acid sequences of a heavy chain variable region and a light chain variable region as set forth in SEQ ID NO: 186 and 187, respectively; an antibody containing the amino acid sequences of a heavy chain variable region and a light chain variable region as set forth in SEQ ID NO: 188 and 189, respectively; an antibody containing the amino acid sequences of a heavy chain variable region and a light chain variable region as set forth in SEQ ID NO: 190 and 191, respectively; an antibody containing the amino acid sequences of a heavy chain variable region and a light chain variable region as set forth in SEQ ID NO: 192 and 193, respectively; and an antibody containing the amino acid sequences of a heavy chain variable region and a light chain variable region as set forth in SEQ ID NO: 194 and 195, respectively. Because this antibody has FR sequences derived from a human antibody, the antibody is preferable in view of safety. Note that the above term "respectively" has the same meaning as "in sequence".

An anti-PAD4 antibody according to an embodiment of the present invention may be at least one antibody selected from the group consisting of: an antibody containing the amino acid sequences of a heavy chain and a light chain as set forth in SEQ ID NO: 170 and 171, respectively; an antibody containing the amino acid sequences of a heavy chain and a light chain as set forth in SEQ ID NO: 172 and 173, respectively; an antibody containing the amino acid sequences of a heavy chain and a light chain as set forth in SEQ ID NO: 174 and 175, respectively; an antibody containing the amino acid sequences of a heavy chain and a light chain as set forth in SEQ ID NO: 176 and 177, respectively; and an antibody containing the amino acid sequences of a heavy chain and a light chain as set forth in SEQ ID NO: 196 and 197, respectively. Because this antibody has FR sequences and constant region sequences derived from a human antibody, the antibody is preferable in view of safety. Note that the above term "respectively" has the same meaning as "in sequence".

As long as an anti-PAD4 antibody according to an embodiment of the present invention exerts desired effects, its heavy chain variable region may contain the amino acid sequence set forth in 186, 188, 190, 192, 194, 155, 156, 157, 162, 163, or 164; the light chain variable region may contain the amino acid sequence set forth in 187, 189, 191, 193, 195, 158, 159, 160, 161, 165, 166, 167, 168, or 169. At this time, the combination of the heavy chain variable region and the light chain variable region has no particular limitation, and any combination may be allowed. Because this antibody has FR sequences derived from a human antibody, the antibody is preferable in view of safety.

As long as an anti-PAD4 antibody according to an embodiment of the present invention exerts desired effects, its heavy chain may contain the amino acid sequence set forth in SEQ ID NO: 170, 172, 174, 176, or 196; and its light chain may contain the amino acid sequence set forth in SEQ ID NO: 171, 173, 175, 177, or 197. At this time, the combination of the heavy chain and the light chain has no particular limitation, and any combination may be allowed. Because this antibody has FR sequences and constant region sequences derived from a human antibody, the antibody is preferable in view of safety.

As long as the anti-PAD4 antibody exerts desired effect, its amino acid sequence listed above may be at least one amino acid sequence selected from the group consisting of: (i) amino acid sequences having one or several amino acid deletions, substitutions, insertions, or additions in the above amino acid sequences; (ii) amino acid sequences having 90% or higher homology to the above amino acid sequences; and (iii) amino acid sequences encoded by polynucleotides specifically hybridized, under a stringent condition, with polynucleotides having nucleotide sequences complementary to nucleotide sequences encoding the above amino acid sequences. The above (i) to (iii) are applicable to the amino acid sequences listed in the sequence listing. When the sequences refer to nucleic acid, the amino acid sequences may be converted to and read as nucleotide sequences.

As used herein, the term "several" may mean that the number is, for example, 10, 8, 6, 5, 4, 3, or 2. The number may be equal to or smaller than any of the above values. It has been known that a polypeptide having its amino acid sequence modified by one or several amino acid residue deletions, additions, insertions, or substitutions with other amino acids can maintain its biological activity (Mark et al., Proc Natl Acad Sci USA., 1984, September, 81(18), 5662-5666; Zoller et al., Nucleic Acids Res., 1982, Oct. 25, 10(20), 6487-6500; and Wang et al., Science, 1984, Jun. 29, 224(4656), 1431-1433). For example, the antibody having such deletions, etc., can be produced using site-specific mutagenesis, random mutagenesis, or biopanning using an antibody phage library. In the site-specific mutagenesis, a KOD-Plus-Mutagenesis kit (TOYOBO CO., LTD.), for example, can be used. In order to select an antibody having substantially the same activity as the wild type from mutant antibodies having deletions, etc., various kinds of characterization can be carried out using FACS analysis, ELISA, etc.

As used herein, the term "90% or more" may mean that the number is, for example, 90, 95, 96, 97, 98, 99% or more, or 100%. The number may be between any two of the above values. The above term "homology" may refer to a ratio of the number of identical amino acids between two or among a plurality of amino acid sequences to the total number of amino acids as calculated in accordance with a method known in the art. Before the calculation of the ratio, amino acid sequences selected from the group of amino acid sequences compared are aligned. If the ratio of the identical amino acids is required to be optimized, gaps are inserted in some portions of the amino acid sequence. Alignment methods, ratio calculation methods, comparison methods, and related computer programs have been conventionally well-known in the art (e.g., BLAST, GENETYX). As used herein, unless otherwise indicated, the term "homology" can be represented by a value determined by the NCBI BLAST program. Blastp can be used in default setting as an algorithm when BLAST is used for amino acid sequence comparison. The numerical values of the measured results are designated under "Positives" or "Identities".

The following conditions, for example, can be used as the above "stringent condition". (1) A low ionic strength solution is used for washing at a high temperature (e.g., a 50° C.

solution containing 0.015 M sodium chloride/0.0015 M sodium citrate/0.1% sodium dodecyl sulfate); (2) a denaturing agent such as formamide is used during hybridization (e.g., a 42° C. solution containing 50% (v/v) formamide, 0.1% bovine serum albumin/0.1% Ficoll/0.1% polyvinylpyrrolidone/50 mM sodium phosphate buffer at pH 6.5, 750 mM sodium chloride, and 75 mM sodium citrate); or (3) a filter is incubated overnight at 37° C. in a solution containing 20% formamide, 5×SSC, 50 mM sodium phosphate (pH 7.6), 5×Denhardt's solution, 10% dextran sulfate, and 20 mg/ml denatured sheared salmon sperm DNA, and the filter is then washed with 1×SSC at about 37 to 50° C. Note that the concentration of formamide may be 50% or more. The washing time may be 5, 15, 30, 60, 120 minutes or longer. A plurality of factors such as a temperature and a salt concentration seem to affect the stringency of a hybridization reaction. The details can be found in Ausubel et al., Current Protocols in Molecular Biology, Wiley Interscience Publishers, (1995).

As used herein, the term "amino acid" means the general term for an organic compound having an amino group and a carboxyl group. When an antibody according to an embodiment of the present invention contains a "specific amino acid sequence", any of amino acids in the amino acid sequence may be chemically modified. In addition, any of amino acids in the amino acid sequence may involve the formation of a salt or a solvate. Also, any of amino acids in the amino acid sequence may be an L-form or D-form amino acid. Even in such a case, an antibody according to an embodiment of the present invention can be said to contain the above "specific amino acid sequence". Known examples of in vivo chemical modifications of amino acids in a protein include: N-terminal modifications (e.g., acetylation, myristylation); C-terminal modifications (e.g., amidation, glycosylphosphatidylinositol addition); and side chain modifications (e.g., phosphorylation, glycosylation).

An embodiment of the present invention provides a polynucleotide or vector which encodes an anti-PAD4 antibody according to the above embodiment of the present invention. This polynucleotide or vector may be introduced into a cell to generate a transformant. The transformants may be cells derived from a human or a non-human mammal (e.g., a rat, mouse, guinea pig, rabbit, cow, monkey, etc.). Examples of the mammalian cells include Chinese hamster ovary (CHO) cells, COS-7 monkey cells, and human embryonic kidney cells (e.g., HEK293 cells). Also, the transformants may be *Escherichia coli* cells, yeast, etc. The above polynucleotide or vector may be constructed so as to enable expression of an anti-PAD4 antibody. The above polynucleotide or vector may contain, for example, a promoter, an enhancer, a replication origin, and/or an antibiotic resistance gene, which are essential components for protein expression. The above polynucleotide or vector may have a foreign nucleotide sequence. The foreign nucleotide sequence may contain nucleotide sequences derived from at least two organisms selected from the group consisting of human and non-human organisms (e.g., bacteria, archaea, yeast, insects, birds, viruses, mammals excluding a human).

Examples of the above vector that can be used include: *E. coli*-derived plasmids (e.g., pET-Blue); *Bacillus subtilis*-derived plasmids (e.g., pUB110); yeast-derived plasmids (e.g., pSH19); expression plasmids for animal cells (e.g., pA1-11, pcDNA3.1-V5/His-TOPO); bacteriophages such as λ phage; and virus-derived vectors. The above vector may be an expression vector and may be a circular one.

Examples of a method for introducing the above polynucleotide or vector into a cell include a calcium phosphate method, lipofection, electroporation, an adenovirus-mediated method, a retrovirus-mediated method, microinjection, and the like ("Genetic Engineering Handbook", 4th Edition, YODOSHA CO., LTD. (2003): 152-179). Each method described in, for example, "Protein Experiment Handbook", YODOSHA CO., LTD., (2003), 128-142 can be used as a process for producing an antibody by using cells.

An embodiment of the present invention provides a process for producing an anti-PAD4 antibody, comprising the step of causing a cell containing a polynucleotide or vector according to the above embodiment of the present invention to proliferate. The above proliferation step includes a culturing step. In addition, this production process may include a step of collecting an anti-PAD4 antibody. In addition, this production process may include a step of preparing a cell culture medium. In addition, this production process may include a step of purifying an anti-PAD4 antibody.

As used herein, examples of a method for purifying an antibody include: ammonium sulfate precipitation; ethanol precipitation; Protein A, Protein G, or gel filtration chromatography; anion- or cation-exchange chromatography; phosphocellulose chromatography; hydrophobic interaction chromatography; affinity chromatography; hydroxylapatite chromatography; lectin chromatography; and the like ("Protein Experiment Handbook", YODOSHA CO., LTD., 2003, 27-52).

An embodiment of the present invention provides a composition containing an anti-PAD4 antibody according to the above embodiment of the present invention. Use of this composition makes it possible to efficiently detect PAD4. In addition, citrullination of PAD4 can be inhibited efficiently. In addition, RA or arthritis can be treated. This composition may contain any component without limitation, and may contain, for example, a buffer. At least one of various embodiments (e.g., a carrier may be included) of the below-described inhibitors and pharmaceutical compositions is applicable to this composition.

An embodiment of the present invention provides an inhibitor of the citrullination activity of PAD4, comprising an anti-PAD4 antibody according to the above embodiment of the present invention. When used, this inhibitor can inhibit the citrullination of PAD4 efficiently. The above inhibitor may decrease the citrullination activity by 20, 30, 40, 60, or 80% or more. The decrease may be between any two of the above values. This decrease may be expressed in a relative percentage while a decrease when PBS is used is set to 0%. As used herein, the term "agent (e.g., an inhibitor)" includes, for example, a composition used for research or treatment. The above inhibitor includes, for example, a therapeutic agent for RA or arthritis. The above inhibitor may be used, for example, in vitro or in vivo. The above inhibitor may contain a composition according to the above embodiment of the present invention. An embodiment of the present invention provides a method for inhibiting the citrullination activity of PAD4, comprising a step of causing an anti-PAD4 antibody according to the above embodiment of the present invention to contact PAD4. An embodiment of the present invention provides a method for inhibiting the citrullination activity of PAD4, comprising a step of administering to a patient an anti-PAD4 antibody according to the above embodiment of the present invention. The above inhibition method includes an inhibition protocol for research or treatment. An embodiment of the present invention provides use of an anti-PAD4 antibody according to the above embodiment of the present invention so as to produce an inhibitor of the citrullination activity of PAD4.

An embodiment of the present invention provides a pharmaceutical composition comprising an anti-PAD4 antibody according to the above embodiment of the present invention. Use of this pharmaceutical composition enables treatment of RA or arthritis. The above pharmaceutical composition may contain at least one pharmacologically acceptable carrier. The above pharmaceutical composition contains, for example, a pharmaceutical composition for treatment of RA or arthritis. The above pharmaceutical composition may contain a composition according to the above embodiment of the present invention. An embodiment of the present invention provides a method for treating a disease, comprising a step of administering to a patient an anti-PAD4 antibody (or a pharmaceutical composition containing an anti-PAD4 antibody) according to the above embodiment of the present invention. The above disease includes, for example, RA or arthritis. An embodiment of the present invention provides use of an anti-PAD4 antibody according to the above embodiment of the present invention so as to produce a pharmaceutical composition.

A report said that the number of patients with RA is as large as 70 million all over the world. Some drugs are currently commercially available, but in a certain percentage of patients, the existing drugs are ineffective. It can be said that 60 to 80% of the patients have not received satisfactory treatment. In addition, it has been pointed out that the existing drugs may also have a side effect problem. Use of an anti-PAD4 antibody according to the above embodiment of the present invention makes it possible to treat RA by a new mechanism of action.

An embodiment of the present invention provides a diagnostic agent for RA or arthritis, comprising an anti-PAD4 antibody according to the above embodiment of the present invention. Use of this diagnostic agent allows for efficient diagnosis of RA or arthritis. An embodiment of the present invention provides a method for diagnosing RA or arthritis, comprising a step of causing a patient's sample to contact an anti-PAD4 antibody according to the above embodiment of the present invention. An embodiment of the present invention provides a reagent for detecting PAD4, comprising an anti-PAD4 antibody according to the above embodiment of the present invention. Use of this reagent allows for efficient detection of PAD4. An embodiment of the present invention provides a method for detecting PAD4, comprising a step of causing a test sample to contact an anti-PAD4 antibody according to the above embodiment of the present invention. An embodiment of the present invention provides a kit comprising an anti-PAD4 antibody according to the above embodiment of the present invention. Use of this kit allows for treatment and diagnosis of a disease or detection of PAD4. This kit may include, for example, a composition, an inhibitor, a pharmaceutical composition, a diagnostic agent, or a detection reagent according to the above embodiments of the present invention. This kit may also include a package insert, a buffer, a container (e.g., a vial or a syringe), or a wrapping.

An embodiment of the present invention provides a pharmaceutical composition comprising an anti-PAD4 antibody and a TNFα inhibitor. Use of this pharmaceutical composition enables treatment of RA or arthritis. A combination of the anti-PAD4 antibody and the TNFα inhibitor can exert a synergistic therapeutic effect on RA or arthritis. In view of the above, this two-component combination can be said to be very excellent as a two-component drug selected when combination therapy is used for treatment of RA or arthritis. In addition, the synergistic therapeutic effect permits a dosage to be reduced, which can achieve very safe treatment.

When an anti-PAD4 antibody and a TNFα inhibitor are used in combination, kinds of the anti-PAD4 antibody have no particular limitation. Examples may include: an anti-PAD4 antibody which specifically binds to an epitope containing positions 345, 347, and 348 of PAD4; antibodies set forth in the above (a) to (f); and antibodies containing heavy chain CDRs 1 to 3 and light chain CDRs 1 to 3 derived from a chicken. In addition, the anti-PAD4 antibody of interest may be an antibody according to the above embodiment of the present invention. Further, commercially available anti-PAD4 antibodies or anti-PAD4 antibodies described in publications may also be used. It is preferable to use a humanized anti-PAD4 antibody as the anti-PAD4 antibody from the viewpoints of safety and increased synergistic effects when the anti-PAD4 antibody and a TNFα inhibitor are used in combination to treat RA or arthritis.

When an anti-PAD4 antibody and a TNFα inhibitor are used in combination, examples of the kind of the TNFα inhibitor may include, but are not particularly limited to, an anti-TNFα antibody, a TNF receptor-fusion protein, a dominant negative TNFα mutant, and an RNAi molecule, miRNA molecule, or antisense nucleic acid against TNFα, and polynucleotides encoding the RNAi molecule, miRNA molecule, or antisense nucleic acid against TNFα. Examples of the anti-TNFα antibody may include infliximab, adalimumabm, golimumab, certolizumab pegol, ozoralizumab, and ABT0122 (anti-IL-17/anti-TNFα bispecific antibody). Examples of the TNF receptor fusion protein may include etanercept. The form of the RNAi molecule may be siRNA or shRNA and the manufacturing thereof can be carried out as a service from a service company (e.g., TAKARA BIO INC.). Any of these biological preparations may be used as the TNFα inhibitor used. It is preferable to use an anti-TNFα antibody or a TNF receptor fusion protein as the TNFα inhibitor from the viewpoint of increased synergistic effects when an anti-PAD4 antibody and the TNFα inhibitor are used in combination to treat RA or arthritis. Particularly preferred is a TNF receptor fusion protein.

An embodiment of the present invention provides an anti-PAD4 antibody-containing pharmaceutical composition used when the anti-PAD4 antibody and a TNFα inhibitor are used in combination. Use of this pharmaceutical composition enables treatment of RA or arthritis. Note that a package insert attached to the above pharmaceutical composition may indicate use of the combination.

An embodiment of the present invention provides a TNFα inhibitor-containing pharmaceutical composition used when an anti-PAD4 antibody and the TNFα inhibitor are used in combination. Use of this pharmaceutical composition enables treatment of RA or arthritis. Note that a package insert attached to the above pharmaceutical composition may indicate use of the combination.

An embodiment of the present invention provides a product comprising an anti-PAD4 antibody-containing pharmaceutical composition and a package or package insert indicating use of a combination of the anti-PAD4 antibody and a TNFα inhibitor. An embodiment of the present invention provides a product comprising a TNFα inhibitor-containing pharmaceutical composition and a package or package insert indicating use of a combination of an anti-PAD4 antibody and the TNFα inhibitor. Use of this product enables treatment of RA or arthritis.

An embodiment of the present invention provides a treatment kit comprising an anti-PAD4 antibody and a TNFα inhibitor. Use of this kit enables treatment of RA or arthritis. This kit may further contain, for example, a buffer, a package insert describing information on an active ingredient, a container for storing the active ingredient, or a package.

As used herein, the wording "used in combination" means that an anti-PAD4 antibody and a TNFα inhibitor may be administered simultaneously or separately. In addition, the wording "used in combination" includes a dosage form where an anti-PAD4 antibody and a TNFα inhibitor are administered as a combination. Further, the wording "used in combination" includes use during combination therapy. Meanwhile, regarding the order of administration, an anti-PAD4 antibody may be first administered or a TNFα inhibitor may be first administered. An embodiment of the present invention provides a combination comprising an anti-PAD4 antibody and a TNFα inhibitor. An embodiment of the present invention provides use of an anti-PAD4 antibody in the manufacture of a pharmaceutical composition used when the anti-PAD4 antibody and a TNFα inhibitor are used in combination. An embodiment of the present invention provides use of a TNFα inhibitor in the manufacture of a pharmaceutical composition used when an anti-PAD4 antibody and the TNFα inhibitor are used in combination.

An embodiment of the present invention provides a treatment method comprising a step of administering, to a subject, an anti-PAD4 antibody and a TNFα inhibitor. Use of this treatment method enables treatment of RA or arthritis. The combination of the anti-PAD4 antibody and the TNFα inhibitor can exert a synergistic therapeutic effect on RA or arthritis. In view of the above, this two-component combination can be said to be very excellent as a two-component drug selected when combination therapy is used for treatment of RA or arthritis. In addition, an embodiment of the present invention provides a treatment method comprising a step of administering, to a subject, an anti-PAD4 antibody and/or a TNFα inhibitor. In addition, an embodiment of the present invention provides use of an anti-PAD4 antibody and/or a TNFα inhibitor in the manufacture of a pharmaceutical composition. The subject may be a patient who has already received an anti-PAD4 antibody or a TNFα inhibitor.

As used herein, the term "treatment" includes exerting a prophylactic effect, an inhibitory effect, or a symptom-improving effect on a disease of a patient or on one or more symptoms involving the disease. As used herein, the "therapeutic drug" may be a pharmaceutical composition containing an active ingredient and at least one pharmacologically acceptable carrier. As used herein, the "pharmaceutical composition" can be produced by any process known in the art of drug formulation. Examples of the process include: mixing an active ingredient with the above carrier. In addition, the dosage form of the pharmaceutical composition is not limited as long as the pharmaceutical composition can be used for treatment. The pharmaceutical composition may be an active ingredient alone or a mixture of an active ingredient and any component. Further, examples of the dosage form of the above carrier include, but are not particularly limited to, a solid and a liquid (e.g., a buffer). The content of the above carrier may be, for example, a pharmaceutically effective dose. This effective dose may be a sufficient amount in view of delivery or pharmaceutical safety of the active ingredient. For example, a buffer is effective in stabilizing the active ingredient in a vial.

An administration route effective in treatment is preferably used for the pharmaceutical composition. Examples of the administration route include intravenous, subcutaneous, intramuscular, intraperitoneal, and oral administration. Examples of the dosage form may include an injection, a capsule, a tablet, and granules. When an antibody is administered, use of an injection is effective. An aqueous solution for an injection may be stored in, for example, a vial or a stainless container. In addition, the aqueous solution for an injection may be formulated with, for example, a saline solution, a sugar (e.g., trehalose), NaCl, or NaOH. Further, the pharmaceutical composition may be formulated with effective amounts of, for example, a buffer (e.g., a phosphate buffer), a pH modifier, and/or a stabilizer.

Examples of the dose include, but are not particularly limited to, 0.01 to 200 mg/kg body weight per dosing. An administration interval is not particularly limited, and the drug may be dosed, for example, once or twice per 1 to 28 days. In addition, the dose, the administration interval, and the administration method can be appropriately selected depending on the age, body weight, symptom, affected organ, etc., of a patient. Further, the pharmaceutical composition preferably contains a therapeutically effective amount or a dose, which is effective in exerting a desired effect, of an active ingredient. When an anti-PAD4 antibody and a TNFα inhibitor are used in combination, the dose of each drug may be lower than the therapeutically effective amount when these drugs are dosed singly.

The therapeutic effect of the pharmaceutical composition may be evaluated using, for example, an arthritis score, an RA score, a swelling size, diagnostic imaging, a modified Total Sharp score, or a disease marker. When the swelling size is used for evaluation, it may be determined that there is a therapeutic effect when a decrease in the swelling size of an affected site during administration of the pharmaceutical composition is significantly more than a decrease in swelling size in the case without administration. Alternatively, it may be determined that there is a therapeutic effect when a decrease in the swelling size of an affected site during administration of the pharmaceutical composition is significantly more than a decrease in the swelling size of an affected site during administration of a negative control substance. The above decrease may be, for example, 40, 50, 60, 70, 80, 90, or 100%. The number may be between any two of the above values.

As used herein, examples of the "patient" include human and non-human mammals (e.g., at least one of a mouse, a guinea pig, a hamster, a rat, a mouse, a rabbit, a pig, a sheep, a goat, a cow, a horse, a cat, a dog, a marmoset, a monkey, and a chimpanzee). Meanwhile, the patient may be a patient who is diagnosed as having RA or arthritis. In addition, the patient may be a patient who is diagnosed as having a disease, treatment of which can be achieved by inhibition of citrullination.

An embodiment of the present invention provides a method for promoting a treatment effect or citrullination activity-inhibitory function of a composition, comprising a step of increasing the compositional proportion of an anti-PAD4 antibody which specifically binds to an epitope containing positions 345, 347, and 348 of PAD4. An embodiment of the present invention provides an anti-PAD4 antibody-containing composition in which at least 90% of the anti-PAD4 antibody in the composition is an anti-PAD4 antibody which specifically binds to an epitope containing positions 345, 347, and 348 of PAD4. An embodiment of the present invention provides an anti-PAD4 antibody-containing antibody population in which at least 90% of the anti-PAD4 antibody is an anti-PAD4 antibody which specifically binds to an epitope containing positions 345, 347, and 348 of PAD4. The above term "at least 90%" may mean that the number is, for example, 90, 95, 96, 97, 98, 99% or more, or 100%. The number may be between any two of the above values.

As used herein, the term "link" may be either a covalent bond or a noncovalent bond, and examples of the link include an ionic bond, a hydrogen bond, a hydrophobic interaction, and a hydrophilic interaction.

As used herein, the term "significantly" may include a case of p<0.05 or p<0.01 when Student's t test (one-sided or two-sided), for example, is used to evaluate a statistically significant difference. Also, the term may include a state in which there is a substantial difference.

Any documents and (patent or patent application) publications, which are cited herein, are incorporated by reference in its entirety.

As used herein, the term "or" may be used when "at least one" matter listed in the text of specification can be employed. The same applies to the term "or". As used herein, when the wording "between any two of the above values" is indicated, the two values are inclusive in the range. As used herein, the phrase "from A to B" means "A or more and B or less".

As described above, the embodiments of the present invention have been illustrated. These embodiments are examples of the present invention. Accordingly, various configurations other than the above embodiments can be adopted. In addition, combinations among the above-described embodiments can also be employed.

EXAMPLES

Hereinafter, the present invention is further illustrated by referring to Examples. The present invention, however, is not limited to them.

<Example 1> Generation of Anti-PAD4 Antibodies

First, three 3-month-old Boris Brown chickens were each intraperitoneally immunized with 333 µg of KLH-modified TA0096 (SEQ ID NO: 1). TA0096 is a peptide antigen corresponding to positions 340 to 356 of PAD4 (SEQ ID NO: 2). Together with the antigen, complete Freund's adjuvant (Wako, 014-09541) was used for the first immunization and incomplete Freund's adjuvant (Wako, 011-09551) was used for the second and third immunization. At the fourth immunization, the antigen diluted in PBS (phosphate buffered saline) was injected intravenously. Blood was drawn from wing vein every other week and ELISA was used to determine the antibody titer. Three chickens were immunized three times and the chicken having the highest antibody titer was immunized four times. This fourth immunization was the final immunization. Three days after the final immunization, the spleen of the chicken was collected. Next, density gradient centrifugation was carried out using Ficoll paque PLUS (GE Healthcare, 17-1440-03) to isolate lymphocytes, from which RNA was extracted using a TRIzole reagent (Life Technologies, 15596026). The extracted RNA was subjected to RT-PCR using a PrimeScript II 1st Strand cDNA Synthesis kit (TAKARA, 6210A) to synthesize cDNA and a scFv phage library was then constructed. An expression vector used was a pPDS expression vector in which a nucleotide sequence encoding a chicken λ chain was inserted instead of a nucleotide sequence encoding a mouse κ chain. The scFv phage library was constructed in accordance with the procedure described in a reference document: "Nakamura et al., J Vet Med Sci., 2004, July, 66(7), 807-814".

The scFv phage antibody library was used for panning using a plate on which a BSA-modified peptide antigen was immobilized. The panning was performed in accordance with the procedure described in a reference document: "Nakamura et al., J Vet Med Sci., 2004, July, 66(7), 807-814". After the fifth panning, the reactivity of the library was examined by ELISA using a plate on which a BSA-modified peptide antigen was immobilized. The library having increased reactivity was subjected to phage screening. In the screening, E. coli were infected with phages and were then plated on 50-µg/ml ampicillin (nacalai, 02739-32)-containing 2×YT Agar plates. The resulting colony was cultured in an ampicillin-containing 2×YT liquid medium. After infection with helper phages, phages of interest were induced in a 2×YT liquid medium containing 50 µg/ml of ampicillin, 25 µg/ml of kanamycin (Meiji Seika Pharma Co., Ltd., GS1-RSS), and 100 µg/ml of IPTG (nacalai, 19742-94). The reactivity of each scFv phage antibody in the resulting culture supernatant was determined by ELISA using an antigen-immobilized plate. The resulting positive clones were sequenced with a DNA sequencer (Applied Biosystems, ABI PRISM 3100-Genetic Analyzer) to determine their sequences.

With respect to each of clones with different sequences, a DNA strand encoding their scFv antibody was used as a template to PCR-amplify the gene encoding an H-chain variable region and an L-chain variable region of a chicken antibody. Then, the PCR products were digested by restriction enzymes SacII (BioLabs Inc., Cat #R0157S) and NheI (BioLabs Inc., Cat #R0131S). Likewise, mouse chimeric antibody (IgG1) expression vectors (H-chain expression vector: pcDNA4/myc-His; L-chain expression vector: pcDNA3/myc-His, Invitrogen) were digested by the restriction enzymes to clone the respective H-chain and L-chain variable region sequences into the respective vectors. After CHO cells were transfected with the H-chain and L-chain constructs prepared, the reactivity of each culture supernatant was examined by ELISA using a plate on which a BSA-modified peptide antigen or a full-length recombinant PAD4 protein was immobilized. As a mouse chimeric antibody expression vector, used was the vector described in Tateishi et al., J Vet Med Sci. 2008 April; 70(4): 397-400. Of the antibody clones as so obtained, A11, E9, G6, G8, G9, and H7 were used in the following experiments. With respect to A11, E9, G6, G8, G9, and H7, the amino acid sequences of their heavy chain variable regions are set forth in SEQ ID NOs: 3 to 8; and the DNA sequences are set forth in SEQ ID NOs: 9 to 14. The amino acid sequences of their light chain variable regions are set forth in SEQ ID NOs: 15 to 20; and the DNA sequences are set forth in SEQ ID NOs: 21 to 26. Hereinafter, these antibodies are sometimes generally referred to as "A11 etc."

For the mass production of each of the antibody clones such as A11 etc., the constructed H-chain and L-chain expression vectors were transfected using an Expi293 Expression system (Invitrogen, A14635). Then, the expressed antibody was purified using Protein G Sepharose 4 Fast Flow (GE healthcare, 17-018-02). Example 2 demonstrates the reactivity of each purified antibody toward PAD4.

<Example 2> Evaluation of the Reactivity of Each Anti-PAD4 Antibody (1) ELISA

ELISA was carried out under the following conditions to evaluate the reactivity of each of A11 etc. toward human or mouse PAD4.

(1-1) Materials

Antigen: full-length recombinant human or mouse PAD4

Antibodies: an anti-dinitrophenyl (DNP) antibody (negative control), L207 (an anti-PAD4 antibody L207-11 describe in Examples of WO2012/026309), A11, E9, G6, G8, G9, and H7

(1-2) Experimental Conditions

TABLE 1

| 1 | Solid-phase antigen immobilization: | 50 µL/well | O/N, at 4° C. | 5 µg/mL of human PAD4 or mouse PAD4 |
|---|---|---|---|---|
| 2 | Blocking: | 250 µL/well | 60 min, at 37° C. | 25% Block Ace/PBS |
| 3 | Primary antibody: | 50 µL/well | 60 min, at 37° C. | 1 µg/mL of each antibody was diluted 4 folds/10% Block Ace |
| 4 | Secondary antibody: | 50 µL/well | 60 min, at 37° C. | HRP-labeled anti-mouse IgG (H + L) in 10% Block Ace/PBS (1:1000) |
| 5 | Chromogenic substrate: | 50 µL/well | 30 min, at RT | OPD solution |
| 6 | Stop solution: | 50 µL/well | | 2N $H_2SO_4$ |
| 7 | Measurement: | Wavelength of 490 nm/630 nm | | |

Figure 1B:
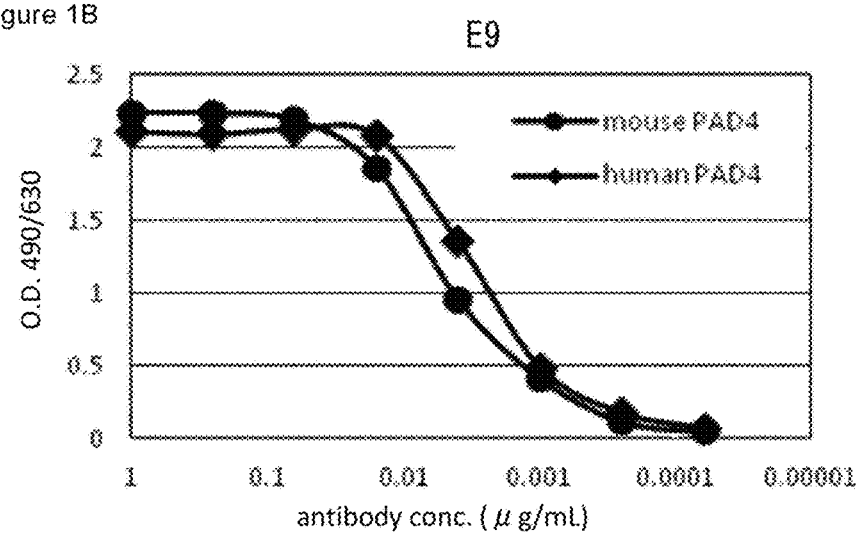
Figure 1C:
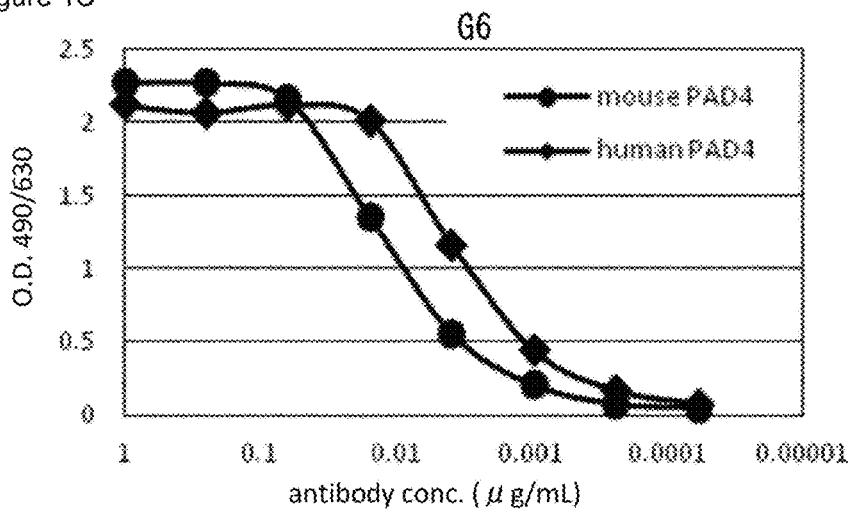
Figure 2A:
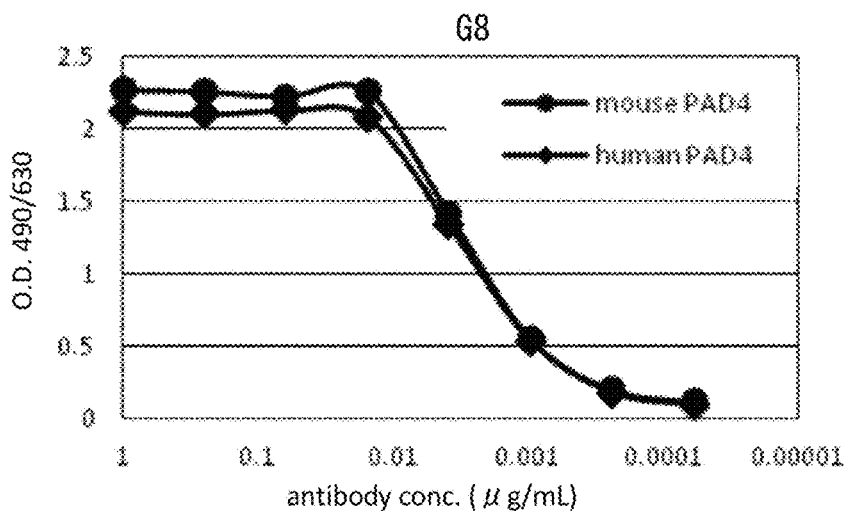
FIGS. 2A-2C are graphs showing the results of ELISA.
Figure 2B:
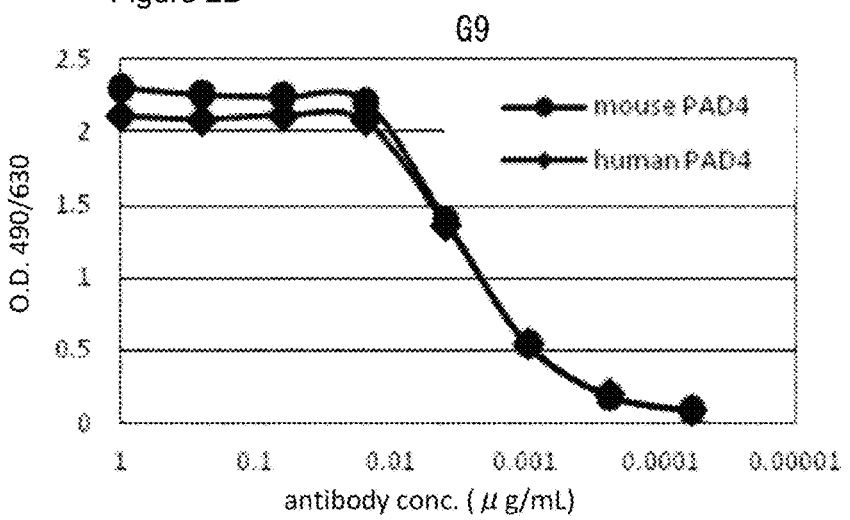
Figure 2C:
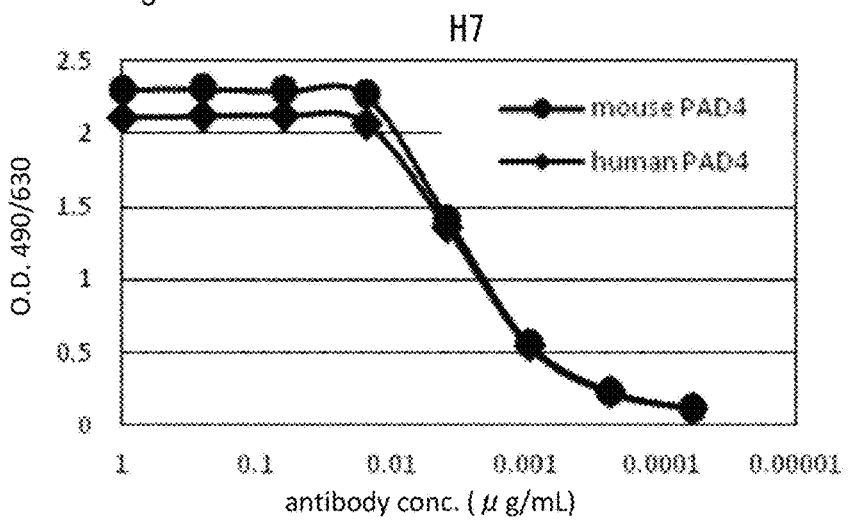
Figure 3A:
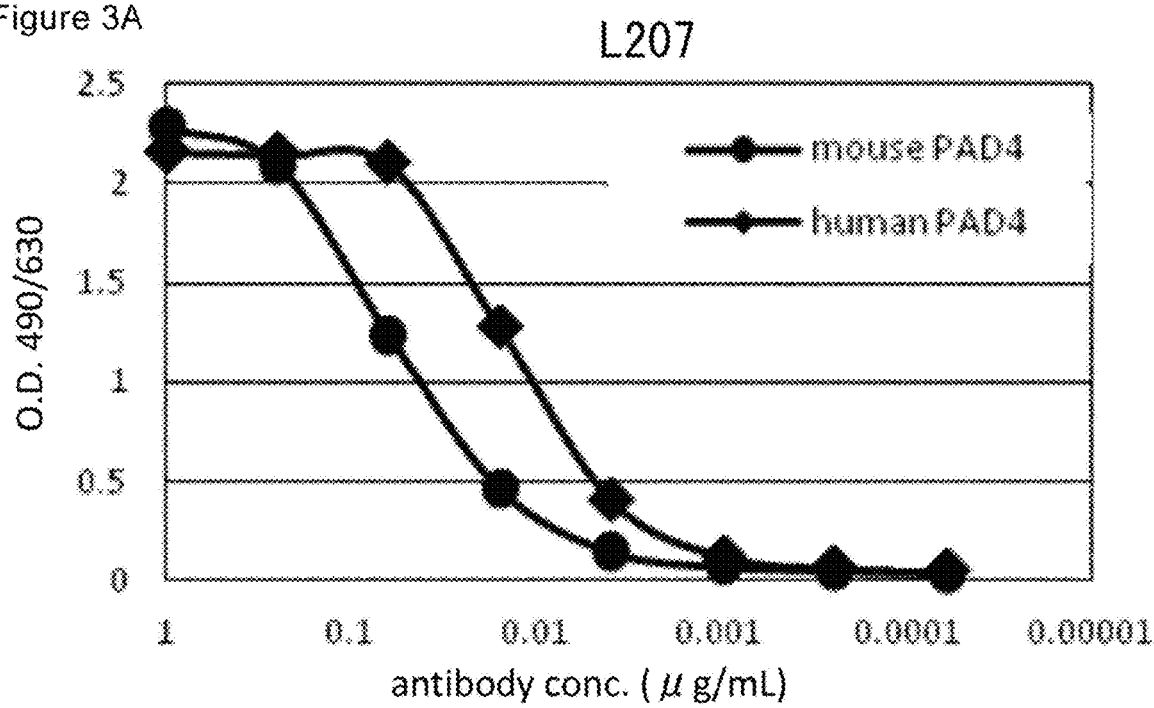
FIGS. 3A-3B are graphs showing the results of ELISA.
Figure 3B:
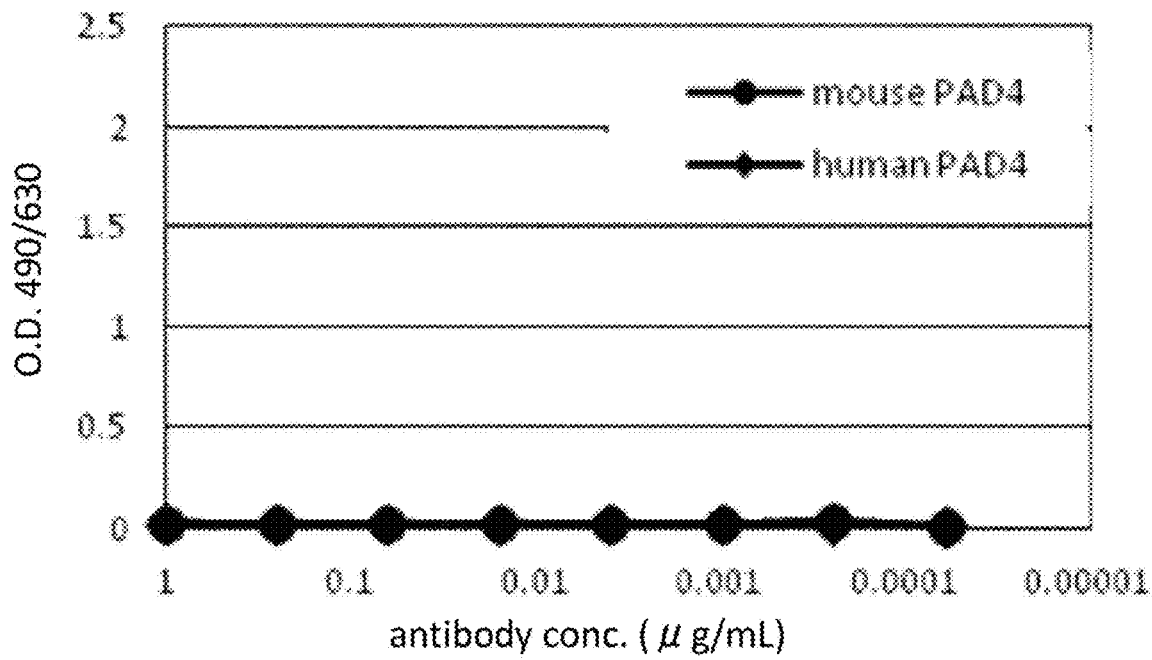

Tables 2 and 3 and FIGS. 1 to 3 show the ELISA results. As seen from the results, any of A11 etc. exhibited a higher affinity than L207.

TABLE 2

Affinity toward human PAD4 (ELISA)

| Antibody concentration (µg/mL) | A11 | E9 | G6 | G8 | G9 | H7 | L207 | Anti-DNP Antibody |
|---|---|---|---|---|---|---|---|---|
| 1 | 2.154 | 2.108 | 2.113 | 2.120 | 2.105 | 2.107 | 2.157 | 0.020 |
| 0.25 | 2.107 | 2.085 | 2.068 | 2.098 | 2.083 | 2.113 | 2.143 | 0.025 |
| 0.0625 | 2.150 | 2.123 | 2.120 | 2.125 | 2.110 | 2.118 | 2.099 | 0.023 |
| 0.015625 | 2.084 | 2.080 | 2.012 | 2.082 | 2.070 | 2.066 | 1.272 | 0.027 |
| 0.0039063 | 1.307 | 1.356 | 1.164 | 1.340 | 1.359 | 1.354 | 0.399 | 0.026 |
| 0.0009766 | 0.511 | 0.489 | 0.437 | 0.544 | 0.534 | 0.537 | 0.116 | 0.023 |
| 0.0002441 | 0.206 | 0.176 | 0.166 | 0.184 | 0.187 | 0.217 | 0.055 | 0.024 |
| 6.104E−05 | 0.063 | 0.070 | 0.075 | 0.100 | 0.082 | 0.111 | 0.042 | 0.009 |

TABLE 3

Affinity toward mouse PAD4 (ELISA)

| Antibody concentration (µg/mL) | A11 | E9 | G6 | G8 | G9 | H7 | L207 | Anti-DNP Antibody |
|---|---|---|---|---|---|---|---|---|
| 1 | 2.242 | 2.235 | 2.275 | 2.264 | 2.304 | 2.304 | 2.28 | 0.028 |
| 0.25 | 2.246 | 2.231 | 2.27 | 2.252 | 2.252 | 2.308 | 2.094 | 0.023 |
| 0.0625 | 2.243 | 2.185 | 2.158 | 2.221 | 2.236 | 2.292 | 1.236 | 0.020 |
| 0.015625 | 2.017 | 1.859 | 1.353 | 2.255 | 2.208 | 2.264 | 0.459 | 0.018 |
| 0.0039063 | 1.072 | 0.956 | 0.550 | 1.417 | 1.385 | 1.414 | 0.137 | 0.024 |
| 0.0009766 | 0.386 | 0.416 | 0.200 | 0.555 | 0.542 | 0.550 | 0.066 | 0.021 |
| 0.0002441 | 0.152 | 0.122 | 0.071 | 0.205 | 0.181 | 0.224 | 0.043 | 0.034 |
| 6.104E−05 | 0.045 | 0.051 | 0.044 | 0.122 | 0.079 | 0.103 | 0.029 | 0.011 |

(2) Affinity Assay

Biacore (GE Healthcare, Biacore T200) was carried out to evaluate the affinity of A11 etc., toward human PAD4. A Mouse Antibody Capture kit (GE Healthcare, BR-1008-38) was used for the affinity assay. Specifically, in accordance with the standard protocol provided by the manufacture, NHS/EDC was used and an amine coupling method, in which a free carboxyl group is fixed on a surface of a CM5 chip, was used to immobilize a rabbit anti-mouse polyclonal antibody on the surface of a CM5 chip. Next, A11 etc., were each captured by the rabbit anti-mouse polyclonal antibody. L207 was likewise captured. Then, human PAD4 at each concentration was subjected to Biacore T200 measurement to create a kinetic sensorgram.

Table 4 and FIG. 4 show the results of affinity assay. As seen from the results, any of A11 etc. exhibited a higher affinity than L207. When the KD (M) thereof was determined, in particular, any of A11 etc. had a high affinity of $9.0 \times 10^{-9}$ or less.

TABLE 4

Affinity toward human PAD4 (Biacore assay)

| | kd (1/s) | ka (1/Ms) | KD (M) |
|---|---|---|---|
| A11 | 5.66E−04 | 1.29E+05 | 4.37E−09 |
| E9 | 8.37E−04 | 1.52E+05 | 5.52E−09 |
| G6 | 3.89E−04 | 4.45E+04 | 8.74E−09 |
| G8 | 2.43E−04 | 1.04E+05 | 2.34E−09 |
| G9 | 2.84E−04 | 9.00E+04 | 3.16E−09 |
| H7 | 7.91E−04 | 1.05E+05 | 7.56E−09 |
| L207 | 1.35E−03 | 1.29E+05 | 1.04E−08 |

<Example 3> Epitope Evaluation

The epitope of each of A11 etc. was identified by alanine scan. Specifically, the following procedures (i) to (iii) were carried out. (i) Each amino acid residue of the antigen sequence (SEQ ID NO: 1) was replaced by another amino acid one by one, and 17 different Ala mutants (SEQ ID Nos: 27 to 43) were synthesized. (ii) The reactivity of each of the Ala mutants toward a test antibody was evaluated (ELISA). (iii) With respect to each of the Ala mutants with which the test antibody was not significantly reacted, an original amino acid residue before the Ala replacement was determined as part of an epitope.

Table 5 shows the experimental conditions of ELISA. The "96 pAb" designated in the table refers to antiserum as obtained by immunizing a chicken with TA0096 (SEQ ID NO: 1). The 96 pAb, which is an anti-PAD4 polyclonal antibody, can substantially keep the affinity toward PAD4 even if any of single amino acids of PAD4 is replaced. When the affinity of the test antibody toward an Ala mutant was 50% or less than the affinity of the 96 pAb toward the Ala mutant, the test antibody was determined to exhibit no significant reactivity.

TABLE 5

| 1 | Solid-phase antigen immobilization: | 50 µL/well | O/N, at 4° C. | 10 µg/mL of a peptide |
|---|---|---|---|---|
| 2 | Blocking: | 250 µL/well | 60 min, at 37° C. | 25% Block Ace/PBS |
| 3 | Primary antibody: | 50 µL/well | 60 min, at 37° C. | 1 µg/mL of each antibody was diluted 4 folds/10% Block Ace (96 pAb was an |

TABLE 5-continued

| | | | |
|---|---|---|---|
| 4 Secondary antibody: | 50 µL/well | 60 min, at 37° C. | exception) 96 pAb (antiserum) was diluted 1000 folds/ 10% Block Ace HRP-labeled anti-mouse IgG (H + L) in 10% Block Ace/PBS (1:1000) HRP-labeled anti-chicken IgG (H + L) in 10% Block Ace/PBS (1:1000) |
| 5 Chromogenic substrate: | 50 µL/well | 30 min, at RT | OPD solution |
| 6 Stop solution: | 50 µL/well | | 2N $H_2SO_4$ |
| 7 Measurement: | Wavelength of 490 nm/630 nm | | |

Table 6 shows the results of ELISA and FIG. 5 shows the results of alanine scan. As seen from the results, A11 etc. were not significantly reacted with Ala mutants, each having a mutation at a position corresponding to position 345, 347, or 348 of PAD4. This revealed that A11 etc. bind specifically to an epitope containing positions 345, 347, and 348 of PAD4.

By contrast, L207 was not significantly reacted with the Ala mutants, each having a mutation at a position corresponding to position 350, 354, or 355 of PAD4. That is, it was revealed that L207 recognizes an epitope different from that of A11 etc.

Note that, as additional experiments, 6 different Ala mutants having 3-amino acid substitution (SEQ ID NOs: 44 to 49) were likewise examined in the experiments. The results demonstrated that all the A11 etc. were not significantly reacted with the Ala mutants, each having a mutation(s) at a position(s) corresponding to position 345, 347, and/or 348 of PAD4.

TABLE 6

| SEQ ID NO of Ala mutant | A11 | E9 | G6 | G8 | G9 | H7 | L207 | 96 pAb | Anti-DNP Antibody |
|---|---|---|---|---|---|---|---|---|---|
| 27 | 1.954 | 1.892 | 1.913 | 1.955 | 1.926 | 1.900 | 1.418 | 1.922 | 0.007 |
| 28 | 2.001 | 1.995 | 1.987 | 1.941 | 1.963 | 1.952 | 1.552 | 1.965 | 0.001 |
| 29 | 2.054 | 1.922 | 1.951 | 1.907 | 1.944 | 1.904 | 1.570 | 1.970 | 0.001 |
| 30 | 2.030 | 1.914 | 1.922 | 1.927 | 2.034 | 1.952 | 1.409 | 1.868 | 0.009 |
| 31 | 1.667 | 1.381 | 1.774 | 1.854 | 1.479 | 0.462 | 1.485 | 1.890 | 0.004 |
| 32 | 0.628 | 0.177 | 0.035 | 0.083 | 0.039 | 0.033 | 1.530 | 1.833 | 0.012 |
| 33 | 2.086 | 1.925 | 1.978 | 1.975 | 1.981 | 1.871 | 1.486 | 1.949 | 0.011 |
| 34 | 0.021 | 0.047 | 0.042 | 0.040 | 0.038 | 0.066 | 1.320 | 1.497 | 0.017 |
| 35 | 0.023 | 0.017 | 0.015 | 0.233 | 0.253 | 0.065 | 1.325 | 1.552 | 0.011 |
| 36 | 1.907 | 1.904 | 1.849 | 1.918 | 1.874 | 1.867 | 1.534 | 1.938 | 0.008 |
| 37 | 1.799 | 1.201 | 1.846 | 1.878 | 1.878 | 1.857 | 0.025 | 1.939 | 0.010 |
| 38 | 1.885 | 1.910 | 1.915 | 1.906 | 1.955 | 1.990 | 1.269 | 1.976 | 0.012 |
| 39 | 1.893 | 1.771 | 1.835 | 1.875 | 1.874 | 1.810 | 1.437 | 1.905 | 0.008 |
| 40 | 1.855 | 1.819 | 1.861 | 1.892 | 1.883 | 1.859 | 1.485 | 1.902 | 0.011 |
| 41 | 1.853 | 1.804 | 1.866 | 1.847 | 1.887 | 1.828 | 0.010 | 1.938 | 0.010 |
| 42 | 1.875 | 1.833 | 1.871 | 1.860 | 1.852 | 1.851 | 0.143 | 1.963 | 0.017 |
| 43 | 1.924 | 1.877 | 1.871 | 1.918 | 1.881 | 1.874 | 1.350 | 1.878 | 0.057 |
| 44 | 1.984 | 1.903 | 1.919 | 1.896 | 1.919 | 1.904 | 1.522 | 1.910 | 0.054 |
| 45 | 0.039 | 0.022 | 0.018 | 0.065 | 0.019 | 0.016 | 1.504 | 1.294 | 0.061 |
| 46 | 0.043 | 0.027 | 0.083 | 0.178 | 0.131 | 0.044 | 0.094 | 1.720 | 0.052 |
| 47 | 1.253 | 1.336 | 1.729 | 1.856 | 1.849 | 1.667 | 0.031 | 1.878 | 0.052 |
| 48 | 1.870 | 1.815 | 1.852 | 1.883 | 1.885 | 1.867 | 0.014 | 1.867 | 0.052 |
| 49 | 1.886 | 1.852 | 1.880 | 1.862 | 1.918 | 1.864 | 0.934 | 1.896 | 0.065 |
| 1 | 1.806 | 1.794 | 1.866 | 1.877 | 1.855 | 1.818 | 1.341 | 1.889 | 0.052 |

<Example 4> Evaluation of Citrullination Activity-Inhibitory Function

The following conditions were used to evaluate the ability of each of A11 etc. to inhibit the citrullination activity of PAD4.

(1) Materials
Recombinant protein: full-length recombinant human or mouse PAD4
Substrate: BAEE (Nα-benzonyl-L-arginine ethyl ester hydrochloride)
Antibodies: a mouse IgG (negative control), an anti-DNP antibody (negative control), L207, A11, E9, G6, G8, G9, and H7

(2) Experimental Conditions
For each of the anti-PAD4 antibodies (L207, A11, E9, G6, G8, G9, and H7) generated, the mouse IgG (negative control), and the anti-DNP antibody (negative control), a 40-nM antibody solution was prepared. This antibody solution was mixed with 5 µL of 3.75 ng/µL (50 nM) human or mouse PAD4 into 20 mM Tris-HCl buffer solution (pH 7.6) containing 1 mM EDTA and 1 mM DTT, such that the total volume was 44 µL. The resulting solution was allowed to stand overnight. Then, 5 µL of 100 mM BAEE (benzoyl arginine ethyl ester) was added under stirring and 1 µL of 0.5 M $CaCl_2$ was further added and well stirred (the total volume: 50 µL; the final concentration of BAEE: 10 mM; the final concentration of calcium ion: 10 mM). This solution was allowed to stand (in a warm water bath) at 37° C. for 3 h. After that, 12.5 µL of 5 M perchloric acid was added to stop the reaction. This solution was allowed to stand for 5 min on ice and centrifuged at 4° C. for 5 min (at 15,000 rpm). Finally, citrullinated BAEE included in the supernatant was subjected to colorimetric quantitative assay.

Table 7 and FIG. 6 show the results of evaluating citrullination activity-inhibitory function. The values of FIG. 6 each indicate the citrullination activity of each antibody when the value in the case of using PBS was set to 100. Any of A11 etc. exhibited a higher citrullination activity-inhibitory function than L207.

TABLE 7

| | Relative citrullination activity |
|---|---|
| Mouse IgG | 106 |
| L207 | 92 |
| A11 | 64 |
| E9 | 59 |
| G6 | 69 |
| G8 | 63 |
| G9 | 68 |
| H7 | 35 |
| PBS | 100 |

Figure 7A:
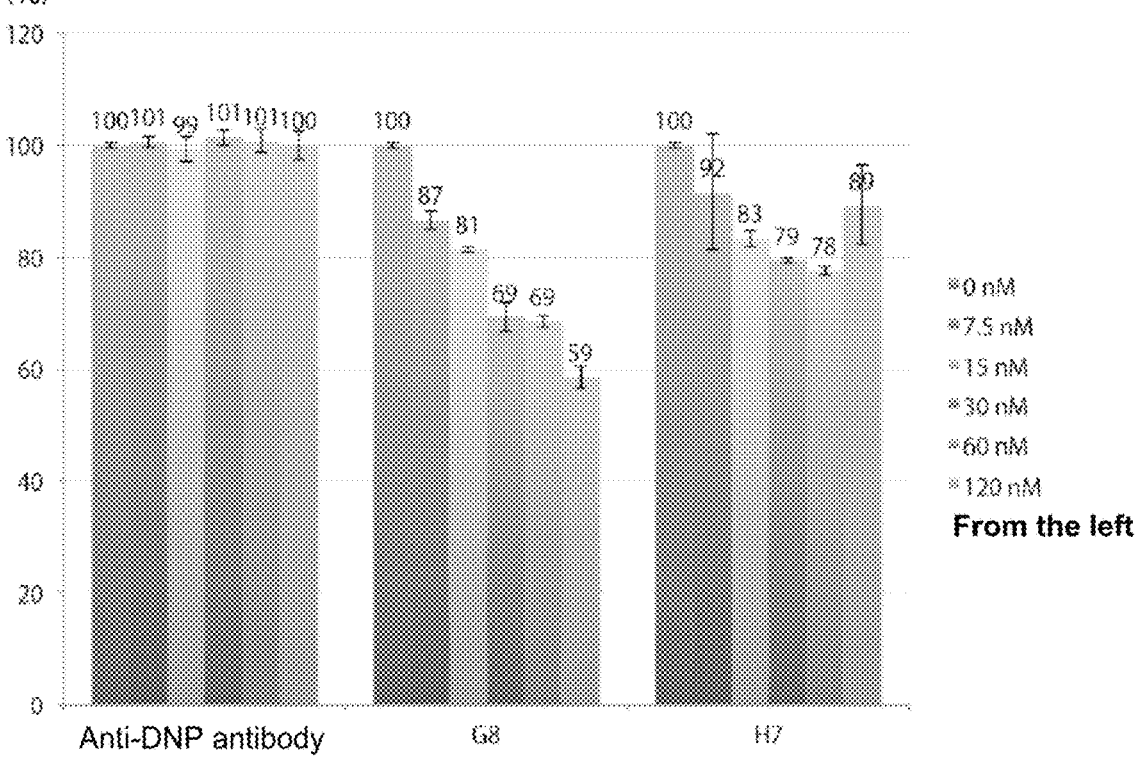
FIGS. 7A-7B are graphs showing the results of evaluating citrullination activity-inhibitory function.
Figure 7B:
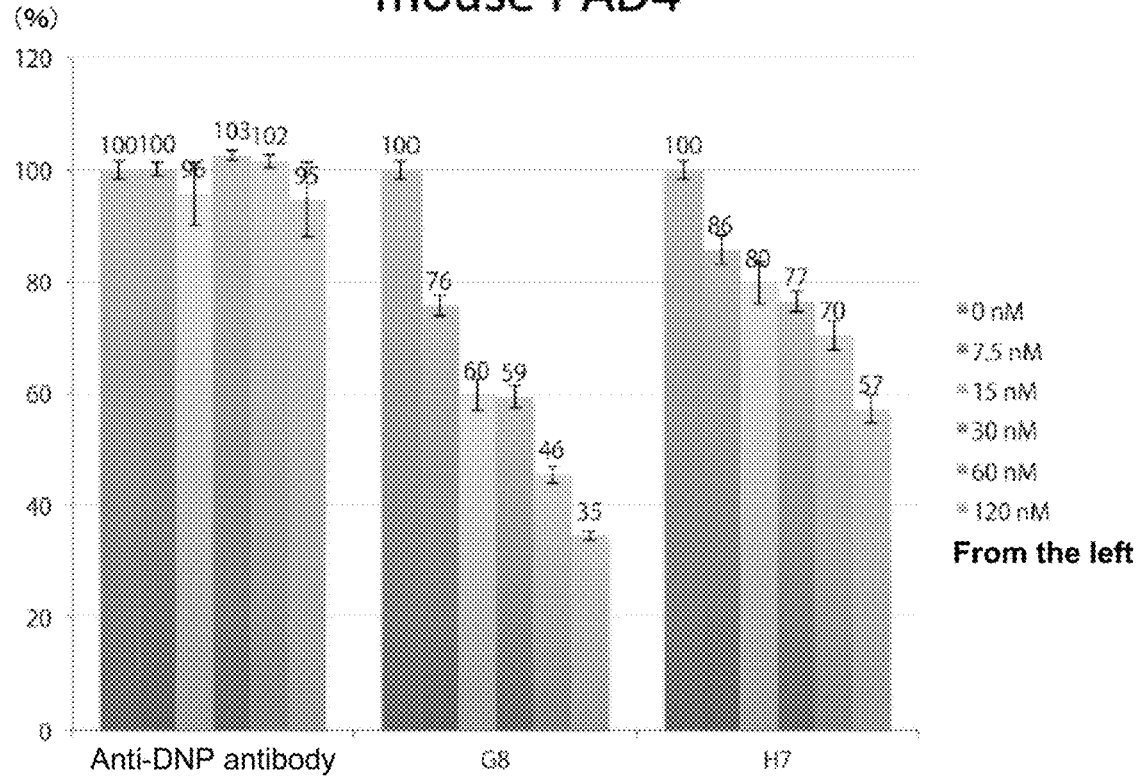

FIG. 7 shows the results as obtained by changing the antibody concentration under substantially the same experimental conditions as above. The values of FIG. 7 each indicate the citrullination activity of G8 or H7 when the value in the case of using the anti-DNP antibody was set to 100. G8 and H7 exhibited a concentration-dependent, citrullination activity-inhibitory function.

<Example 5> Efficacy Evaluation (1) Evaluation of Insteps and Joints
Collagen antibody-induced arthritis (CAIA) model mice were used to evaluate the efficacy of G8. The CAIA model mouse is a model mouse for rheumatoid arthritis (RA) and arthritis. A procedure for generating a CAIA model mouse was in accordance with a protocol using an antibody cocktail (Chondrex Inc., 53040) for triggering mouse arthritis. FIG. 8 shows an outline of the experimental conditions. At day 0, an anti-collagen antibody mixture (1.5 mg) was injected into a tail vein of 8-week-old female Balb/c mouse (5 to 7 mice/group). At day 3, 37.5 μg of LPS (inflammation-inducing substance) was intraperitoneally administered. At days 0, 2, 4, 6, and 8, G8, the anti-DNP antibody, or PBS was intraperitoneally administered as a test substance (at 1 mg/mouse). At days 1 to 10, the size of swelling of each instep (footpad) or each joint (ankle) was measured. The numerical value of the swelling size was designated as the average of the values for both left and right limbs. At days 0 to 10, arthritis of the hind limb was scored in accordance with Table 8 (the maximum value was 8/mouse).

TABLE 8

| Arthritis sign (observed macroscopically) | Arthritis score |
|---|---|
| There were swellings of 1 to 2 fingers. | 1 |
| There were swellings of 3 to 5 fingers. | 2 |
| Moderate swelling was observed throughout the limbs. | 3 |
| Severe swelling was observed throughout the limbs. | 4 |

Figure 9A:
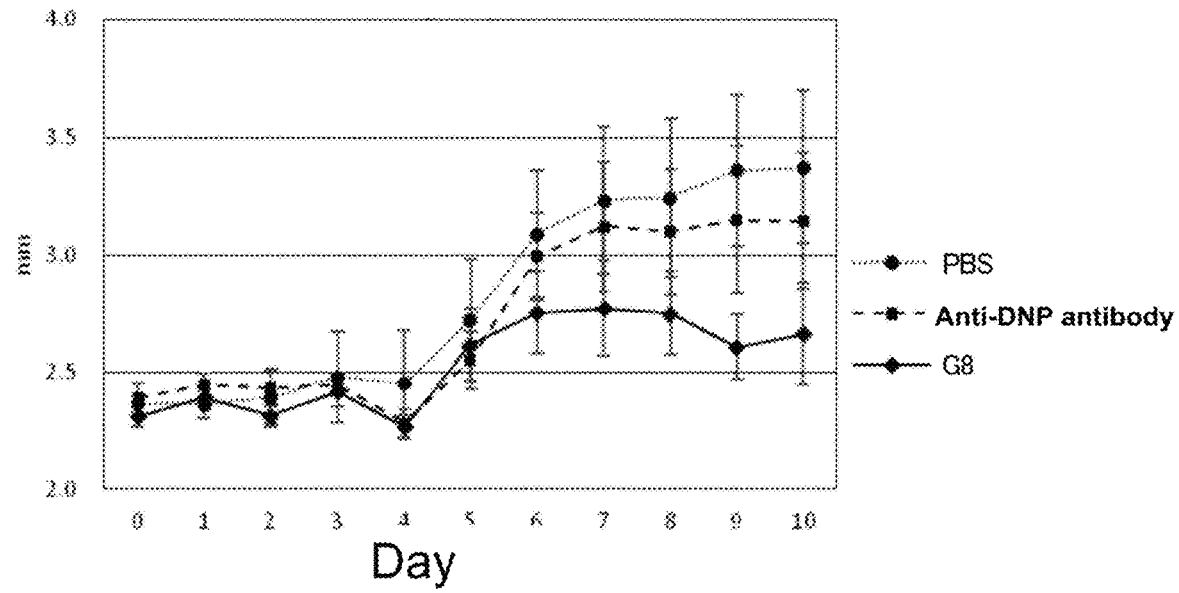
FIGS. 9A-9B are graphs showing the results of evaluating the size of swelling.
Figure 9B:
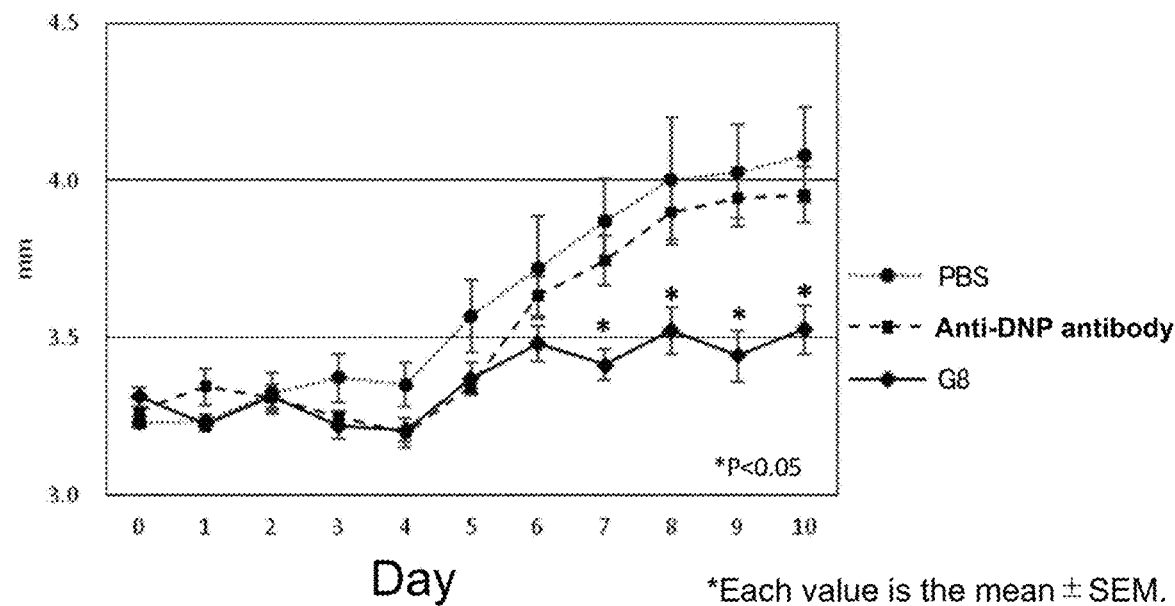

Tables 9 to 10 and FIG. 9 show the results of evaluating the size of swelling. Table 11 and FIG. 10 show the results of evaluating the arthritis score. As seen from the results, G8 exerted an increased therapeutic effect on RA. Note that the present inventors demonstrated, in another experiment, that L207 exerted no significant therapeutic effect on RA.

TABLE 9

The size of swelling of an instep (PBS: n = 5; the anti-DNP antibody and G8: n = 7)

| Day | 0 | 1 | 2 | 3 | 4 | 5 | 6 | 7 | 8 | 9 | 10 |
|---|---|---|---|---|---|---|---|---|---|---|---|
| Average (mm) | | | | | | | | | | | |
| PBS | 2.37 | 2.36 | 2.39 | 2.48 | 2.45 | 2.72 | 3.09 | 3.23 | 3.25 | 3.36 | 3.37 |
| Anti-DNP antibody | 2.39 | 2.44 | 2.43 | 2.45 | 2.28 | 2.55 | 2.99 | 3.12 | 3.10 | 3.15 | 3.15 |
| G8 | 2.31 | 2.39 | 2.31 | 2.41 | 2.27 | 2.62 | 2.76 | 2.77 | 2.75 | 2.61 | 2.66 |
| SEM | | | | | | | | | | | |
| PBS | 0.04 | 0.06 | 0.12 | 0.19 | 0.23 | 0.26 | 0.27 | 0.31 | 0.34 | 0.32 | 0.33 |
| Anti-DNP antibody | 0.06 | 0.05 | 0.08 | 0.04 | 0.06 | 0.12 | 0.19 | 0.27 | 0.27 | 0.31 | 0.29 |
| G8 | 0.04 | 0.03 | 0.04 | 0.06 | 0.05 | 0.16 | 0.17 | 0.21 | 0.18 | 0.14 | 0.22 |

TABLE 10

The size of swelling of a joint (PBS: n = 5; the anti-DNP antibody and G8: n = 7)

| Day | 0 | 1 | 2 | 3 | 4 | 5 | 6 | 7 | 8 | 9 | 10 |
|---|---|---|---|---|---|---|---|---|---|---|---|
| Average (mm) | | | | | | | | | | | |
| PBS | 3.23 | 3.24 | 3.32 | 3.37 | 3.35 | 3.57 | 3.72 | 3.87 | 4.01 | 4.03 | 4.08 |
| Anti-DNP antibody | 3.27 | 3.35 | 3.31 | 3.25 | 3.20 | 3.34 | 3.63 | 3.75 | 3.90 | 3.95 | 3.95 |
| G8 | 3.31 | 3.23 | 3.31 | 3.22 | 3.21 | 3.37 | 3.48 | 3.41 | 3.52 | 3.44 | 3.53 |
| SEM | | | | | | | | | | | |
| PBS | 0.02 | 0.03 | 0.06 | 0.08 | 0.07 | 0.11 | 0.16 | 0.14 | 0.20 | 0.15 | 0.15 |
| Anti-DNP antibody | 0.04 | 0.06 | 0.04 | 0.02 | 0.05 | 0.02 | 0.06 | 0.08 | 0.10 | 0.09 | 0.09 |
| G8 | 0.03 | 0.02 | 0.03 | 0.04 | 0.04 | 0.05 | 0.05 | 0.05 | 0.07 | 0.08 | 0.08 |

TABLE 11

Arthritis score (PBS: n = 5; the anti-DNP antibody and G8: n = 7)

| Day | 0 | 1 | 2 | 3 | 4 | 5 | 6 | 7 | 8 | 9 | 10 |
|---|---|---|---|---|---|---|---|---|---|---|---|
| Average | | | | | | | | | | | |
| PBS | 0.00 | 0.00 | 0.20 | 0.40 | 1.00 | 2.20 | 4.40 | 4.80 | 5.20 | 5.40 | 5.40 |
| Anti-DNP antibody | 0.00 | 0.00 | 0.14 | 0.00 | 0.43 | 2.00 | 3.86 | 4.71 | 4.57 | 5.00 | 5.14 |
| G8 | 0.00 | 0.00 | 0.00 | 0.14 | 0.14 | 1.43 | 2.71 | 2.14 | 1.57 | 1.71 | 1.71 |

TABLE 11-continued

| Arthritis score (PBS: n = 5; the anti-DNP antibody and G8: n = 7) | | | | | | | | | | | |
|---|---|---|---|---|---|---|---|---|---|---|---|
| Day | 0 | 1 | 2 | 3 | 4 | 5 | 6 | 7 | 8 | 9 | 10 |
| | | | | | SEM | | | | | | |
| PBS | 0.00 | 0.00 | 0.20 | 0.24 | 0.55 | 0.49 | 0.75 | 0.73 | 0.97 | 0.87 | 0.87 |
| Anti-DNP antibody | 0.00 | 0.00 | 0.14 | 0.00 | 0.20 | 0.58 | 0.51 | 0.42 | 0.43 | 0.49 | 0.46 |
| G8 | 0.00 | 0.00 | 0.00 | 0.14 | 0.14 | 0.43 | 0.61 | 0.51 | 0.65 | 0.52 | 0.42 |

(2) Evaluation of Titer of Anti-CCP Antibody

Under the same experimental conditions as of the above (1), blood was drawn at days 0, 2, 5, 8, and 10, and the titer of anti-CCP antibody in serum was measured. At that time, G8 or the anti-DNP antibody was used as a test substance.

Table 12 and FIG. 11 show the results of measuring the titer of anti-CCP antibody. As seen from the results, G8 suppressed an increase in the titer of anti-CCP antibody. That is, G8 inhibited the citrullination activity of PAD4.

TABLE 12

| Anti-CCP antibody titer (anti-DNP antibody and G8: n = 7) | | | | | |
|---|---|---|---|---|---|
| Day | 0 | 2 | 5 | 8 | 10 |
| | | Average (unit/mL) | | | |
| Anti-DNP antibody | 3.27 | 4.39 | 7.62 | 9.11 | 8.53 |
| G8 | 2.42 | 3.27 | 3.43 | 6.81 | 5.23 |
| | | SEM | | | |
| Anti-DNP antibody | 0.45 | 0.46 | 1.35 | 1.12 | 0.93 |
| G8 | 0.15 | 0.38 | 0.49 | 0.66 | 0.53 |

(3) Histological Analysis

Under the same experimental conditions as of the above (1), a hind limb removed at day 10 was fixed in 4% formaldehyde, dehydrated, and then embedded in paraffin. Hematoxylin/eosin staining was performed to examine inflammation of a joint. At that time, G8, the anti-DNP antibody, or PBS was used as a test substance.

FIG. 12 shows the results of histological analysis. The left panels of FIG. 12 are photographs at or near a finger joint. Regarding the PBS or anti-DNP antibody administration group, inflammatory cells such as neutrophils and/or macrophages invaded the joint and the surrounding, so that the synovial membrane was damaged. By contrast, in the case of G8, inflammatory cells did not invade. The right panels are magnified views of the boxed regions of the above photographs and display the surface of a cartilage layer. As indicated by arrow heads, the surface was damaged and indented in the PBS or anti-DNP antibody administration group. By contrast, in the case of the G8 administration group, a smooth cartilage layer was maintained. In view of the above, G8 was demonstrated to exert a therapeutic effect on RA.

<Example 6> Efficacy Evaluation

Collagen antibody-induced arthritis (CAIA) model mice were used to evaluate the efficacy of G8 or H7. The CAIA model mouse is a model mouse for rheumatoid arthritis (RA) and arthritis. A procedure for generating a CAIA model mouse was in accordance with a protocol using an antibody cocktail (Chondrex Inc., 53040) for triggering mouse arthritis. FIG. 13 shows an outline of the experimental conditions. At day 0, an anti-collagen antibody mixture (1.5 mg) was injected into a tail vein of 8-week-old female Balb/c mouse (5 to 7 mice/group). At day 3, 37.5 μg of LPS (inflammation-inducing substance) was intraperitoneally administered. At days 0, 2, 4, 6, and 8, G8, H7, or the anti-DNP antibody was intraperitoneally administered as a test substance (at 1 mg/mouse). At days 1 to 10, the size of swelling of each instep (footpad) or each joint (ankle) was measured. The numerical value of the swelling size was designated as the average of the values for both left and right limbs. At days 0 to 10, the arthritis score was determined in accordance with the following (i) to (iii). (i) Evaluation sites included each of the fingers, insteps, and joints of left and right hind limbs. (ii) The arthritis was scored in accordance with Table 13. (iii) The arthritis score (the maximum value was 28/mouse) was obtained by averaging the total score of the fingers, insteps, and joints of left and right hind limbs.

TABLE 13

| Arthritis sign (observed macroscopically) | Arthritis score |
|---|---|
| Moderate swelling | 1 |
| Severe swelling | 2 |

Figure 14A:
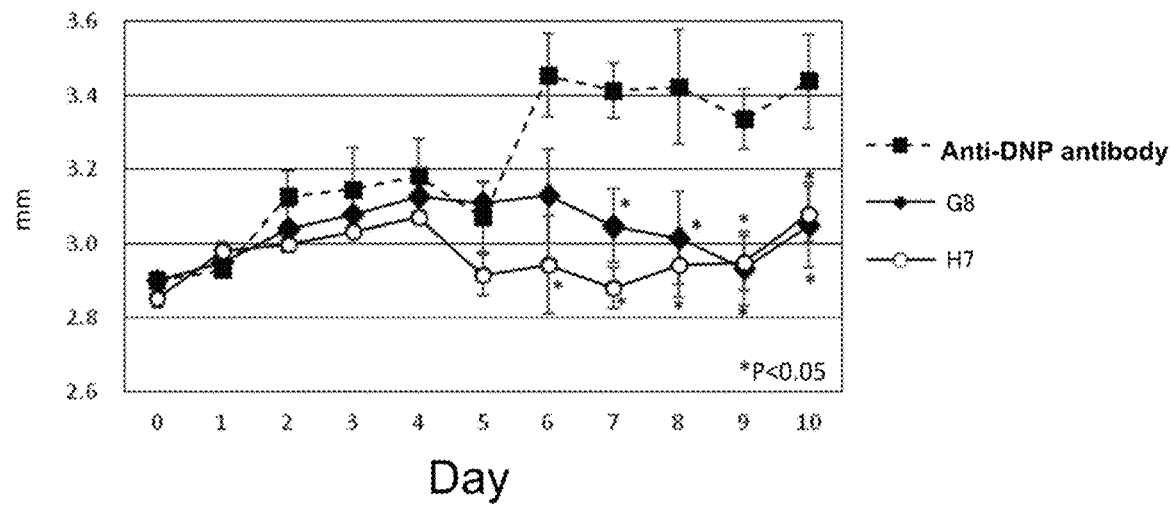
FIGS. 14A-14B are graphs showing the results of evaluating the size of swelling.
Figure 14B:
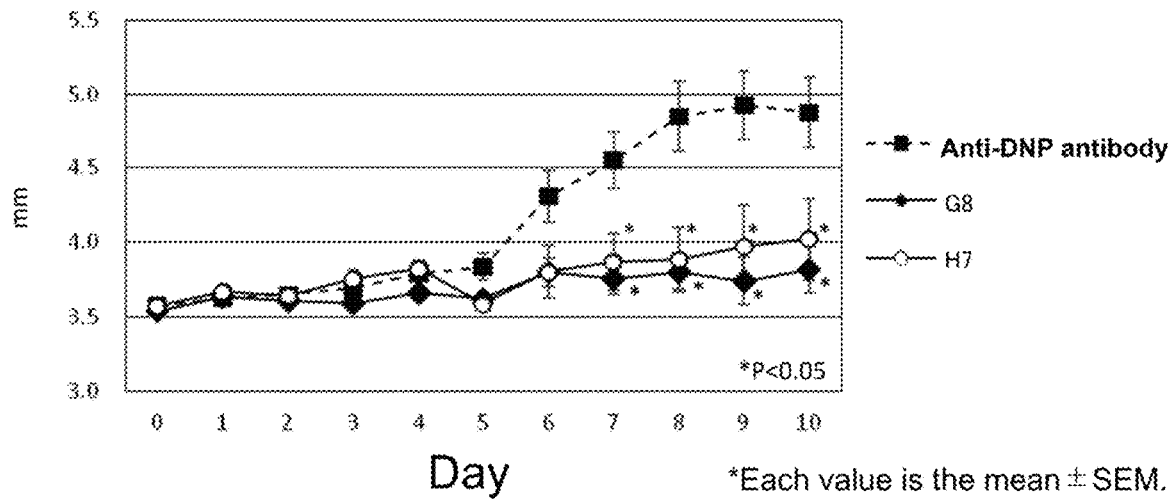
Figure 24A:
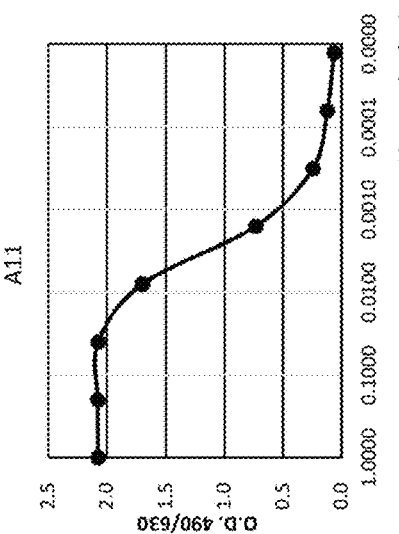
FIGS. 24A-24E are a table and graphs showing the results of ELISA.
Figure 24D:
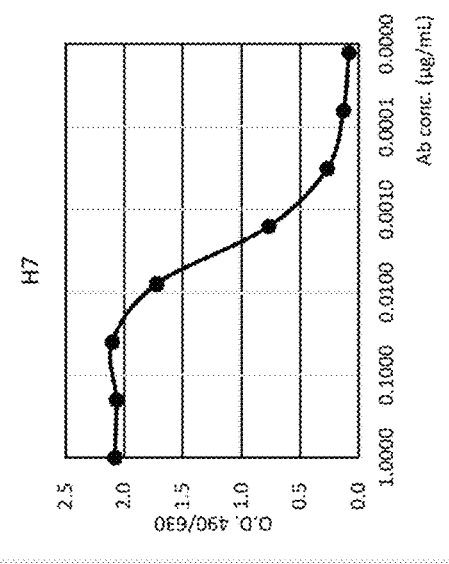
Figure 24E:
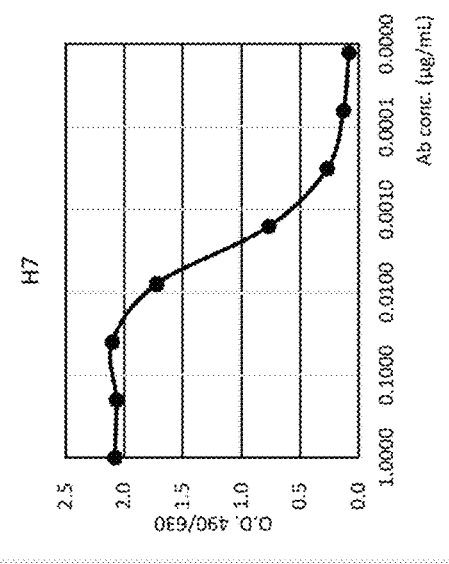
Figure 24C:
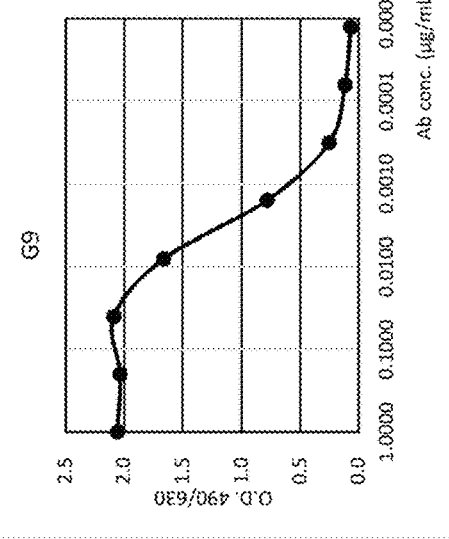
Figure 24B:
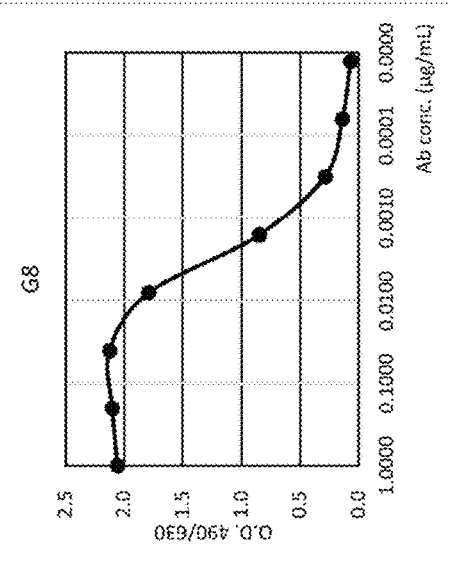

Tables 14 to 15 and FIG. 14 show the results of evaluating the size of swelling. Table 16 and FIG. 15 show the results of evaluating the arthritis score. As seen from the results, G8 and H7 exerted an increased therapeutic effect on RA.

TABLE 14

| The size of swelling of an instep (the anti-DNP antibody: n = 5; G8: n = 7; H7: n = 5) | | | | | | | | | | | |
|---|---|---|---|---|---|---|---|---|---|---|---|
| Day | 0 | 1 | 2 | 3 | 4 | 5 | 6 | 7 | 8 | 9 | 10 |
| | | | | | Average (mm) | | | | | | |
| Anti-DNP antibody | 2.90 | 2.93 | 3.13 | 3.15 | 3.18 | 3.07 | 3.45 | 3.41 | 3.42 | 3.34 | 3.44 |
| G8 | 2.90 | 2.95 | 3.04 | 3.08 | 3.13 | 3.11 | 3.13 | 3.05 | 3.02 | 2.93 | 3.05 |
| H7 | 2.85 | 2.98 | 3.00 | 3.04 | 3.07 | 2.91 | 2.94 | 2.88 | 2.94 | 2.95 | 3.08 |

TABLE 14-continued

The size of swelling of an instep (the anti-DNP antibody:
n = 5; G8: n = 7; H7: n = 5)

| Day | 0 | 1 | 2 | 3 | 4 | 5 | 6 | 7 | 8 | 9 | 10 |
|---|---|---|---|---|---|---|---|---|---|---|---|
| SEM | | | | | | | | | | | |
| Anti-DNP antibody | 0.02 | 0.02 | 0.07 | 0.11 | 0.10 | 0.09 | 0.11 | 0.07 | 0.15 | 0.08 | 0.13 |
| G8 | 0.02 | 0.02 | 0.06 | 0.05 | 0.04 | 0.06 | 0.13 | 0.10 | 0.12 | 0.10 | 0.11 |
| H7 | 0.02 | 0.03 | 0.02 | 0.03 | 0.01 | 0.06 | 0.13 | 0.06 | 0.09 | 0.08 | 0.08 |

TABLE 15

The size of swelling of a joint (the anti-DNP antibody: n = 5; G8: n = 7; H7: n = 5)

| Day | 0 | 1 | 2 | 3 | 4 | 5 | 6 | 7 | 8 | 9 | 10 |
|---|---|---|---|---|---|---|---|---|---|---|---|
| Average (mm) | | | | | | | | | | | |
| Anti-DNP antibody | 3.57 | 3.63 | 3.65 | 3.69 | 3.79 | 3.83 | 4.31 | 4.55 | 4.85 | 4.92 | 4.88 |
| G8 | 3.54 | 3.63 | 3.61 | 3.59 | 3.66 | 3.62 | 3.80 | 3.76 | 3.80 | 3.74 | 3.82 |
| H7 | 3.57 | 3.67 | 3.64 | 3.76 | 3.83 | 3.59 | 3.80 | 3.87 | 3.89 | 3.97 | 4.02 |
| SEM | | | | | | | | | | | |
| Anti-DNP antibody | 0.01 | 0.03 | 0.02 | 0.04 | 0.03 | 0.09 | 0.18 | 0.19 | 0.24 | 0.24 | 0.24 |
| G8 | 0.02 | 0.02 | 0.04 | 0.04 | 0.04 | 0.05 | 0.10 | 0.11 | 0.11 | 0.16 | 0.15 |
| H7 | 0.02 | 0.01 | 0.01 | 0.05 | 0.05 | 0.04 | 0.17 | 0.19 | 0.22 | 0.27 | 0.27 |

TABLE 16

Arthritis score (the anti-DNP antibody: n = 5; G8: n = 7; H7: n = 5)

| Day | 0 | 1 | 2 | 3 | 4 | 5 | 6 | 7 | 8 | 9 | 10 |
|---|---|---|---|---|---|---|---|---|---|---|---|
| Average | | | | | | | | | | | |
| Anti-DNP antibody | 0 | 3.0 | 5.4 | 5.8 | 4.6 | 7.0 | 12.8 | 17.2 | 14.6 | 16.2 | 16.2 |
| G8 | 0 | 3.6 | 6.0 | 5.1 | 4.6 | 7.1 | 8.9 | 10.4 | 10.1 | 9.6 | 11.9 |
| H7 | 0 | 3.8 | 5.4 | 5.8 | 2.6 | 5.4 | 6.6 | 8.0 | 7.4 | 8.0 | 8.8 |
| SEM | | | | | | | | | | | |
| Anti-DNP antibody | 0 | 0.6 | 0.4 | 0.5 | 0.9 | 0.5 | 1.4 | 1.9 | 1.5 | 1.8 | 2.1 |
| G8 | 0 | 0.8 | 0.4 | 0.6 | 0.2 | 0.4 | 1.4 | 2.4 | 2.6 | 2.4 | 2.6 |
| H7 | 0 | 1.0 | 0.7 | 1.1 | 0.6 | 0.9 | 1.6 | 1.9 | 2.0 | 2.1 | 2.3 |

<Example 7> Evaluation of Humanized Anti-PAD4 Antibodies (1) Generation of Humanized Anti-PAD4 Antibodies (IgG1κ)

The antibodies were humanized with reference to Nishibori et al., Mol Immunol. 2006 February; 43(6):634-42. When G8 and H7 were used to generate humanized anti-PAD4 antibodies, 4.00, 4.15, or 4.32 H-chain template described in the above literatures was used for each H-chain. Regarding the L-chain of G8, 4.00, 4.06, 4.17, or 4.29 template was used. Regarding the L-chain of H7, 4.00, 4.06, 4.15, 4.17, or 4.29 template was used. The variable regions of the humanized antibodies were designed such that with respect to the sequences of CDRs 1, 2, and 3 of the H- and L-chains of each antibody, the respective CDRs are inserted into sites corresponding to each template. The designed variable regions were synthesized using a service from Invitrogen, Inc. The nucleotide sequences encoding the variable regions of the G8 or H7 as so designed are set forth in respective SEQ ID NOs: 135 to 146. The variable region sequences synthesized were PCR-amplified using: primers (1) and (2) for amplifying each H-chain variable region; and primers (3) and (4) for amplifying each L-chain variable region.

```
H-chain forward primer (1)
                              (SEQ ID NO: 147)
5'-ATATAGGCGCGCCGAGGTGCAGCTGTTGGAG-3'

Reverse primer (2)
                              (SEQ ID NO: 148)
5'-TATATGGATCCTCACCTGAGGAGACGGTGA-3'

L-chain forward primer (3)
                              (SEQ ID NO: 149)
5'-ATATAGGCGCGCCAGCTATGAGCTGACTCAGCCA-3'

Reverse primer (4)
                              (SEQ ID NO: 150)
5'-TATATGGATCCACTCACCCAGGACGGTCAG-3'
```

Each PCR amplification product and the expression vectors in which a human IgG1 constant region was cloned were digested by AscI and BamHI (R0558S, R0136S) and were used for subcloning. The expression vectors having an H-chain or L-chain constant region sequence were disclosed in JP-A-2005-245337. The final constructs were sequenced to confirm that they each had a sequence of interest. In these constructs, the H-chain sequence was converted to IgG1 form and the L-chain sequence was converted to κ form. Further, corresponding constructs for A11 and G9 were likewise constructed. The nucleotide sequence encoding the variable region of the A11 or G9 as so designed is set forth in SEQ ID NO: 151 (A11-H4.00) or 152 (G9-L4.29), respectively. Eventually, all the IgG1κ-type antibodies had an H-chain with H4.00 framework and an L-chain with L4.29 framework. Note that A11 and G9 share the L-chain sequence and G8, G9, and H7 share the H-chain sequence.

FIG. 16 shows the amino acid sequences of the constant regions of the H-chain (IgG1) and the L-chain (κ) of a humanized antibody. FIG. 17 shows the sequences of variable regions of a humanized antibody G8. FIG. 18 shows the sequences of variable regions of a humanized antibody H7 (the H-chain sequence is the same as of G8). FIGS. 19 and 20 show the full-length amino acid sequences of humanized antibodies derived from G8, H7, A11, and G9. The amino acid sequences of the heavy chain of each of the humanized antibodies derived from G8, H7, A11, and G9 are the amino acid sequences set forth in SEQ ID NOs: 172, 176, 170, and 174, respectively. The amino acid sequences of the light chain are the amino acid sequences set forth in SEQ ID NOs: 173, 177, 171, and 175, respectively.

The respective humanized anti-PAD4 antibody expression vectors as obtained through the above experiments were used to prepare purified antibodies. In terms of the technique, the H-chain and L-chain expression vectors were transfected into mammalian cultured cells using an Expi293 Expression system (Thermo Fisher Scientific, A14635). Then, each antibody expressed was purified using rProtein A Sepharose Fast Flow (GE healthcare, 17-127-902). The resulting purified antibody was used for ELISA using human PAD4 as an antigen to examine its reactivity.

(2) Reactivity of Each Humanized Anti-PAD4 Antibody Toward Human PAD4

The humanized anti-PAD4 antibodies derived from G8 and H7 were each used for ELISA to examine their reactivity. At that time, three types of the H-chain and four types of the L-chain were used (Table 17). The class of each antibody was IgG1κ. Table 18 shows the experimental conditions. The experimental results are shown in FIGS. 21 to 23. Any of the humanized anti-PAD4 antibodies exhibited a high affinity toward human PAD4.

TABLE 17

| G8 | | H7 | |
|---|---|---|---|
| VH | VL | VH | VL |
| H4.00 | L4.00 | H4.00 | L4.00 |
| H4.00 | L4.06 | H4.00 | L4.06 |
| H4.00 | L4.17 | H4.00 | L4.15 |
| H4.00 | L4.29 | H4.00 | L4.17 |
| H4.15 | L4.00 | H4.15 | L4.00 |
| H4.15 | L4.06 | H4.15 | L4.06 |
| H4.15 | L4.17 | H4.15 | L4.15 |
| H4.15 | L4.29 | H4.15 | L4.17 |
| H4.32 | L4.00 | H4.32 | L4.00 |
| H4.32 | L4.06 | H4.32 | L4.06 |

TABLE 17-continued

| G8 | | H7 | |
|---|---|---|---|
| VH | VL | VH | VL |
| H4.32 | L4.17 | H4.32 | L4.15 |
| H4.32 | L4.29 | H4.32 | L4.17 |

TABLE 18

| 1 | Solid-phase antigen immobilization: | 50 μL/well | O/N at 4° C. | 5 μg/mL human PAD4 |
|---|---|---|---|---|
| 2 | Blocking: | 250 μL/well | 60 min at 37° C. | 25% Block Ace/PBS |
| 3 | Primary Ab: | 50 μL/well | 60 min at 37° C. | Each antibody at 1 μg/mL was diluted 2 fold/10% Block Ace |
| 4 | Secondary Ab: | 50 μL/well | 60 min at 37° C. | HRP-labeled anti-human IgG (H + L) in 10% Block Ace/PBS (1:1000) |
| 5 | Chromogenic substrate: | 50 μL/well | 30 min at RT | OPD solution |
| 6 | Stop solution: | 50 μL/well | | 2N $H_2SO_4$ |
| 7 | Wavelength 490 nm/630 nm | | | |

(3) Reactivity of Humanized Anti-PAD4 Antibody Toward Human PAD4

The humanized anti-PAD4 antibodies derived from G8, H7, A11, and G9 were each used for ELISA to examine their reactivity. At that time, the combination of the variable region frameworks was such that the H-chain framework was H4.00 and the L-chain framework was L4.293. The class of each antibody was IgG1κ. Table 19 shows the experimental conditions. The experimental results are shown in FIG. 24. Any of the humanized anti-PAD4 antibodies exhibited a high affinity toward human PAD4.

TABLE 19

| 1 | Solid-phase antigen immobilization: | 50 μL/well | O/N at 4° C. | 5 μg/mL human PAD4 |
|---|---|---|---|---|
| 2 | Blocking: | 250 μL/well | 60 min at 37° C. | 25% Block Ace/PBS |
| 3 | Primary Ab: | 50 μL/well | 60 min at 37° C. | Each antibody at 1 μg/mL was diluted 5 fold/10% Block Ace |
| 4 | Secondary Ab: | 50 μL/well | 60 min at 37° C. | HRP-labeled anti-human IgG (H + L) in 10% Block Ace/PBS (1:1000) |
| 5 | Chromogenic substrate: | 50 μL/well | 30 min at RT | OPD solution |
| 6 | Stop solution: | 50 μL/well | | 2N $H_2SO_4$ |
| 7 | Wavelength 490 nm/630 nm | | | |

(4) Generation of Humanized Anti-PAD4 Antibody (IgG4λ) and Evaluation of its Reactivity The same procedure as of the above "(1) Generation of Humanized Anti-PAD4 Antibodies (IgG1κ)" was used to generate a humanized anti-PAD4 antibody (IgG4λ) derived from H7. In this regard, however, the DNA strands shown in FIG. 25 were synthesized for vector construction. FIG. 26 shows the amino acid sequences of the variable region and the constant region of the H-chain and the variable region and the constant region of the light chain.

Next, the H7-derived, humanized anti-PAD4 antibody (IgG4λ) was used for ELISA to examine its reactivity. At that time, the combination of the variable region frames was such that the H-chain framework was H4.00 and the L-chain framework was L4.29. The class of the antibody was IgG4λ. Table 20 shows the experimental conditions. The experimental results are shown in FIG. 27. The H7-derived, humanized anti-PAD4 antibody (IgG4λ) exhibited a high affinity toward human PAD4.

TABLE 20

| 1 | Solid-phase antigen immobilization: | 50 μL/well | O/N at 4° C. | 5 μg/mL human PAD4 |
|---|---|---|---|---|
| 2 | Blocking: | 250 μL/well | 60 min at 37° C. | 25% Block Ace/PBS |
| 3 | Primary Ab: | 50 μL/well | 60 min at 37° C. | Each antibody at 1 μg/mL was diluted 5 fold/10% Block Ace |
| 4 | Secondary Ab: | 50 μL/well | 60 min at 37° C. | HRP-labeled anti-human IgG (H + L) in 10% Block Ace/PBS (1:1000) |
| 5 | Chromogenic substrate: | 50 μL/well | 30 min at RT | TMB solution |
| 6 | Stop solution: | 50 μL/well | | TMB stop solution |
| 7 | | | Wavelength 450 nm/650 nm | |

(5) Affinity Assay

The humanized anti-PAD4 antibodies derived from G8 and H7 were subjected to Biacore (GE Healthcare, Biacore T200) assay to evaluate their affinity. At that time, the combination of the frameworks was such that the H-chain framework was H4.00 and the L-chain framework was L4.29. The class of each antibody used was IgG1κ. Full-length recombinant human PAD4 was used as an antigen. A Human Antibody Capture kit (GE Healthcare, BR-1008-39) was used for the affinity assay. Specifically, in accordance with the standard protocol provided by the manufacture, NHS/EDC was used and an amine coupling method, in which a free carboxyl group is fixed on a surface of a CM5 chip, was used to immobilize a rabbit anti-human polyclonal antibody on the surface of a CM5 chip. Next, the humanized anti-PAD4 antibodies were each captured by the rabbit anti-human polyclonal antibody. Human PAD4 at each concentration was subjected to Biacore T200 measurement to create a kinetic sensorgram.

Table 21 shows the results of affinity assay. As seen from the results, any of the humanized anti-PAD4 antibodies derived from G8 and H7 exhibited a high affinity. When the KD (M) thereof was measured, in particular, any of them had a high affinity of $9.0 \times 10^{-9}$ or less.

TABLE 21

| | kd (1/s) | ka (1/Ms) | KD (M) |
|---|---|---|---|
| Humanized Ab #G8-H4.00/L4.29 | 2.00E−04 | 1.03E+05 | 1.95E−09 |
| Humanized Ab #H7-H4.00/L4.29 | 5.07E−04 | 6.13E+05 | 8.28E−09 |

(6) Evaluation of Citrullination Activity-Inhibitory Function.

The following conditions were used to evaluate the ability of each of the humanized anti-PAD4 antibodies derived from A11 etc. to inhibit the citrullination activity of PAD4.

(6-1) Materials

Recombinant protein: full-length recombinant human PAD4

Substrate: BAEE (Nα-benzoyl-L-arginine ethyl ester hydrochloride)

Antibodies: a humanized anti-DNP antibody (negative control), humanized anti-PAD4 antibodies clones derived from A11, G8, G9, and H7 (the combination of all the frameworks of each antibody were H4.00-L4.29; the class of each antibody was IgG1κ)

(6-2) Experimental Conditions

An antibody solution containing 120, 60, 30, 15, or 7.5 nM of each of the generated humanized anti-PAD4 antibodies (derived from A11, G8, G9, and H7) and the anti-DNP antibody (negative control) was prepared. This antibody solution was mixed with 5 μL of 3.75 ng/μL (50 nM) human PAD4 into 20 mM Tris-HCl buffer solution (pH 7.6) containing 1 mM EDTA and 1 mM DTT, such that the total volume was 44 μL. The resulting solution was allowed to stand at 37° C. for 30 min. Then, 5 μL of 100 mM BAEE (benzoyl arginine ethyl ester) was added under stirring and 1 of 0.5 M CaCl$_2$ was further added and well stirred (the total volume: 50 μL; the final concentration of BAEE: 10 mM; the final concentration of calcium ion: 10 mM). This solution was allowed to stand (in a warm water bath) at 37° C. for 3 h. After that, 12.5 μL of 5 M perchloric acid was added to stop the reaction. This solution was allowed to stand for 5 min on ice and centrifuged at 4° C. for 5 min (at 15,000 rpm). Finally, citrullinated BAEE included in the supernatant was subjected to colorimetric quantitative assay.

(6-3) Experimental Conditions

FIG. 28 shows relative activity when the amount (4.9 nmol/16 μL of a reaction solution) of production of citrulline by using 0 nM of the anti-DNP antibody was set to 100%. Each humanized anti-PAD4 antibody exhibited a concentration-dependent, citrullination activity-inhibitory function.

<Example 8> Study on Combined Administration of Humanized Anti-PAD4 Antibody and TNFα Inhibitor (1) Materials The humanized anti-PAD4 antibody (IgG1κ) clone derived from H7 and a TNFα inhibitor Etanercept were used to conduct an experiment to test an arthritis inhibitory effect in D1CC mice (a transgenic non-human mammal in which the pathology of human rheumatoid arthritis can be reproduced; WO2005/085438).

(2) Conditions

As the first immunization, Freund's complete adjuvant containing bovine type II collagen (10 ng) was administered to each mouse. As the second immunization, Freund's incomplete adjuvant containing the same bovine type II collagen (10 ng) was administered. After the second immunization, the above test substances were each administered intraperitoneally twice every week over 8 weeks. After the administration, swelling of a joint portion was macroscopically observed and then scored.

(3) Test Groups

αDNP Ab: 500 μg/mouse (25 mg/kg)

αPAD4 Ab. 100 μg: 100 μg (5 mg/kg)

αPAD4 Ab. 500 μg: 500 μg (25 mg/kg)

ETN. 100 μg: 100 μg (5 mg/kg)

ETN. 500 μg: 500 μg (25 mg/kg)

Combination: αPAD4 Ab. 100 μg+ETN. 100 μg (4) Results

It was observed that combined administration of the humanized anti-PAD4 antibody and the TNFα inhibitor provides a significantly higher therapeutic benefit than single drug dosing (p<0.05). In addition, it was also observed that this combined administration exerted a synergistic therapeutic effect when compared with the single drug dosing. This demonstrated that the combined use of the humanized anti-PAD4 antibody and the TNFα inhibitor allowed for a low-dose setting and made it possible to achieve treatment having excellent safety and efficacy. Moreover, no clear side effects due to the antibody administration were observed.

DISCUSSION

The above Examples have revealed that the anti-PAD4 antibodies which specifically bind to an epitope containing positions 345, 347, and 348 of PAD4 exert potent therapeutic effects on RA. In addition, these antibodies have stronger affinity toward PAD4 and higher citrullination activity-inhibitory function than the known conventional antibody L207.

It was further revealed that the combined administration of the anti-PAD4 antibody and the TNFα inhibitor exerted a synergistic therapeutic effect on RA.

Hereinabove, the present invention has been described based on the Examples. These Examples are absolutely examples. It should be understood by those skilled in the art that various modifications are allowed, and those modifications are also within the scope of the present invention.

The invention claimed is:

1. An anti-PAD4 (peptidylarginine deiminase 4) monoclonal antibody which specifically binds to positions 345, 347, and 348 of human PAD4, and wherein said antibody inhibits citrullination activity of PAD4 and binds human PAD4 with a KD (M) of $9.0 \times 10^{-9}$ or less.

2. The anti-PAD4 monoclonal antibody according to claim 1, wherein the positions are identified by alanine scan in which a single amino acid is replaced.

3. The anti-PAD4 monoclonal antibody according to claim 1, wherein the antibody is a humanized antibody.

4. The anti-PAD4 monoclonal antibody according to claim 1, wherein the antibody is an antigen-binding fragment.

5. A polynucleotide or vector which encodes the anti-PAD4 antibody according to claim 1.

6. A process for producing an anti-PAD4 antibody, comprising introducing the polynucleotide or vector of claim 5 into a cell and culturing said cell to express the antibody.

7. A composition comprising the anti-PAD4 monoclonal antibody according to claim 1.

8. A method of inhibiting citrullination activity of human PAD4, comprising contacting human PAD4 with the anti-PAD4 antibody according to claim 1.

9. A method of treating rheumatoid arthritis, comprising administering to a patient in need thereof the anti-PAD4 antibody according to claim 1.

10. The anti-PAD4 monoclonal antibody according to claim 1, wherein the antibody binds to a peptide, the amino acid sequence of which is set forth in SEQ ID NO: 1, but cannot bind to a peptide, the amino acid sequence of which is set forth in SEQ ID NO: 32, 34, or 35.

11. An anti-PAD4 antibody comprising:
heavy chain CDRs 1 to 3 and light chain CDRs 1 to 3 comprising amino acid sequences set forth in SEQ ID NOs: 50 to 55, respectively;
heavy chain CDRs 1 to 3 and light chain CDRs 1 to 3 comprising amino acid sequences set forth in SEQ ID NOs: 56 to 61, respectively;
heavy chain CDRs 1 to 3 and light chain CDRs 1 to 3 comprising amino acid sequences set forth in SEQ ID NOs: 62 to 67, respectively;
heavy chain CDRs 1 to 3 and light chain CDRs 1 to 3 comprising amino acid sequences set forth in SEQ ID NOs: 68 to 73, respectively;
heavy chain CDRs 1 to 3 and light chain CDRs 1 to 3 comprising amino acid sequences set forth in SEQ ID NOs: 74 to 79, respectively; or
heavy chain CDRs 1 to 3 and light chain CDRs 1 to 3 comprising amino acid sequences set forth in SEQ ID NOs: 80 to 85, respectively.

12. The anti-PAD4 antibody according to claim 11, wherein the antibody inhibits citrullination activity of PAD4.

13. The anti-PAD4 antibody according to claim 11, wherein the antibody is a humanized antibody.

14. The anti-PAD4 antibody according to claim 11, wherein a KD (M) between the antibody and PAD4 is $9.0 \times 10^{-9}$ or less.

15. The anti-PAD4 antibody according to claim 11, wherein the antibody is a monoclonal antibody.

16. The anti-PAD4 antibody according to claim 11, wherein the antibody is an antigen-binding fragment.

17. A polynucleotide or vector which encodes the anti-PAD4 antibody according to claim 11.

18. A process for producing an anti-PAD4 antibody, comprising introducing the polynucleotide or vector of claim 17 into a cell and culturing said cell to express the antibody.

19. A composition comprising the anti-PAD4 antibody according to claim 11.

20. A method of inhibiting citrullination activity of human PAD4, comprising contacting human PAD4 with the anti-PAD4 antibody according to claim 11.

21. A method of treating rheumatoid arthritis, comprising administering to a patient in need thereof the anti-PAD4 antibody according to claim 11.

* * * * *

SEQUENCE LISTING

```
<160> NUMBER OF SEQ ID NOS: 197

<210> SEQ ID NO 1
<211> LENGTH: 17
<212> TYPE: PRT
<213> ORGANISM: Artificial Sequence
<220> FEATURE:
<223> OTHER INFORMATION: peptide antigen

<400> SEQUENCE: 1

Glu Glu Asn Met Asp Asp Gln Trp Met Gln Asp Glu Met Glu Ile Gly
1               5                   10                  15

Tyr

<210> SEQ ID NO 2
<211> LENGTH: 663
<212> TYPE: PRT
<213> ORGANISM: Homo sapiens

<400> SEQUENCE: 2

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
                20                  25                  30

Ala Pro Glu Asp Cys Thr Ser Phe Ser Ile Asn Ala Ser Pro Gly Val
            35                  40                  45

Val Val Asp Ile Ala His Gly Pro Pro Ala Lys Lys Lys Ser Thr Gly
        50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
```

```
                 210                 215                 220
Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                    245                 250                 255

Pro Asp Thr Asp Phe Pro Gly Leu Ile Thr Leu Thr Ile Ser Leu Leu
                260                 265                 270

Asp Thr Ser Asn Leu Glu Leu Pro Glu Ala Val Val Phe Gln Asp Ser
                275                 280                 285

Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                    325                 330                 335

Cys Pro Glu Glu Glu Asn Met Asp Asp Gln Trp Met Gln Asp Glu Met
                340                 345                 350

Glu Ile Gly Tyr Ile Gln Ala Pro His Lys Thr Leu Pro Val Val Phe
                355                 360                 365

Asp Ser Pro Arg Asn Arg Gly Leu Lys Glu Phe Pro Ile Lys Arg Val
                370                 375                 380

Met Gly Pro Asp Phe Gly Tyr Val Thr Arg Gly Pro Gln Thr Gly Gly
385                 390                 395                 400

Ile Ser Gly Leu Asp Ser Phe Gly Asn Leu Glu Val Ser Pro Pro Val
                    405                 410                 415

Thr Val Arg Gly Lys Glu Tyr Pro Leu Gly Arg Ile Leu Phe Gly Asp
                420                 425                 430

Ser Cys Tyr Pro Ser Asn Asp Ser Arg Gln Met His Gln Ala Leu Gln
            435                 440                 445

Asp Phe Leu Ser Ala Gln Gln Val Gln Ala Pro Val Lys Leu Tyr Ser
    450                 455                 460

Asp Trp Leu Ser Val Gly His Val Asp Glu Phe Leu Ser Phe Val Pro
465                 470                 475                 480

Ala Pro Asp Arg Lys Gly Phe Arg Leu Leu Leu Ala Ser Pro Arg Ser
                485                 490                 495

Cys Tyr Lys Leu Phe Gln Glu Gln Gln Asn Glu Gly His Gly Glu Ala
                500                 505                 510

Leu Leu Phe Glu Gly Ile Lys Lys Lys Gln Gln Lys Ile Lys Asn
                515                 520                 525

Ile Leu Ser Asn Lys Thr Leu Arg Glu His Asn Ser Phe Val Glu Arg
                530                 535                 540

Cys Ile Asp Trp Asn Arg Glu Leu Leu Lys Arg Glu Leu Gly Leu Ala
545                 550                 555                 560

Glu Ser Asp Ile Ile Asp Ile Pro Gln Leu Phe Lys Leu Lys Glu Phe
                565                 570                 575

Ser Lys Ala Glu Ala Phe Phe Pro Asn Met Val Asn Met Leu Val Leu
                580                 585                 590

Gly Lys His Leu Gly Ile Pro Lys Pro Phe Gly Pro Val Ile Asn Gly
                595                 600                 605

Arg Cys Cys Leu Glu Glu Lys Val Cys Ser Leu Leu Glu Pro Leu Gly
                610                 615                 620

Leu Gln Cys Thr Phe Ile Asn Asp Phe Phe Thr Tyr His Ile Arg His
625                 630                 635                 640
```

Gly Glu Val His Cys Gly Thr Asn Val Arg Arg Lys Pro Phe Ser Phe
                645                 650                 655
Lys Trp Trp Asn Met Val Pro
            660

<210> SEQ ID NO 3
<211> LENGTH: 119
<212> TYPE: PRT
<213> ORGANISM: chicken

<400> SEQUENCE: 3

Ala Val Thr Leu Asp Glu Ser Gly Gly Leu Gln Thr Pro Gly Gly
1               5                   10                  15
Ala Leu Ser Leu Val Cys Lys Ala Ser Gly Phe Asp Phe Ser Ser Tyr
            20                  25                  30
Gly Met Gly Trp Met Arg Gln Ala Pro Gly Lys Gly Leu Glu Tyr Val
        35                  40                  45
Ala Ala Ile Arg Asn Asp Gly Ser Trp Thr Gly Tyr Gly Ala Ala Val
    50                  55                  60
Lys Gly His Ala Thr Ile Ser Arg Asp Asn Gly Gln Ser Thr Val Arg
65                  70                  75                  80
Leu Gln Leu Asn Asn Leu Arg Ala Glu Asp Thr Gly Thr Tyr Tyr Cys
                85                  90                  95
Ala Lys Thr Thr Gly Ser Arg Gly Ser Ile Asp Ala Trp Gly His
            100                 105                 110
Gly Thr Glu Val Ile Val Ser
        115

<210> SEQ ID NO 4
<211> LENGTH: 119
<212> TYPE: PRT
<213> ORGANISM: chicken

<400> SEQUENCE: 4

Ala Val Thr Leu Asp Glu Ser Gly Gly Leu Gln Thr Pro Gly Gly
1               5                   10                  15
Thr Leu Ser Leu Val Cys Lys Gly Ser Gly Phe Thr Phe Ser Ser Tyr
            20                  25                  30
Gly Met Gly Trp Met Arg Gln Ala Pro Gly Lys Gly Leu Glu Tyr Val
        35                  40                  45
Ala Ala Ile Arg Asn Asp Gly Ser Trp Thr Gly Tyr Gly Ser Ala Val
    50                  55                  60
Lys Gly Arg Ala Thr Ile Ser Arg Asp Asn Gly Gln Ser Thr Val Arg
65                  70                  75                  80
Leu Gln Leu Asn Asn Leu Arg Ala Glu Asp Thr Ala Thr Tyr Tyr Cys
                85                  90                  95
Ala Lys Thr Ser Gly Ser Gly Gly Ser Val Asp Ala Trp Gly His
            100                 105                 110
Gly Thr Glu Val Ile Val Ser
        115

<210> SEQ ID NO 5
<211> LENGTH: 119
<212> TYPE: PRT
<213> ORGANISM: chicken

<400> SEQUENCE: 5

```
Ala Val Thr Leu Asp Glu Ser Gly Gly Gly Leu Gln Thr Pro Gly Gly
 1               5                  10                 15
Ala Leu Ser Leu Val Cys Lys Ala Ser Gly Phe Thr Phe Ser Ser Tyr
            20                  25                 30
Gly Met Glu Trp Val Arg Gln Ala Pro Gly Lys Gly Leu Glu Tyr Val
        35                  40                  45
Ala Ala Ile Arg Asn Asp Gly Ser Trp Thr Gly Tyr Gly Ala Ala Val
    50                  55                  60
Lys Gly Arg Ala Thr Ile Ser Arg Asp Asp Gly Gln Ser Thr Leu Arg
65                  70                  75                  80
Leu Gln Leu Asn Asn Leu Arg Ala Glu Asp Thr Ala Thr Tyr Tyr Cys
                85                  90                  95
Ala Lys Thr Thr Gly Ser Ser Gly Ser Ile Asp Ala Trp Gly His
            100                 105                 110
Gly Thr Glu Val Ile Val Ser
            115

<210> SEQ ID NO 6
<211> LENGTH: 119
<212> TYPE: PRT
<213> ORGANISM: chicken

<400> SEQUENCE: 6

Ala Val Thr Leu Asp Glu Ser Gly Gly Gly Leu Gln Thr Pro Gly Gly
 1               5                  10                 15
Ala Leu Ser Leu Val Cys Lys Ala Ser Gly Phe Thr Phe Ser Thr Tyr
            20                  25                 30
Ala Met Gly Trp Met Arg Gln Ala Pro Gly Lys Gly Leu Glu Tyr Val
        35                  40                  45
Ala Ala Ile Arg Asn Asp Gly Ser Trp Thr Gly Tyr Gly Ala Ala Val
    50                  55                  60
Lys Gly Arg Ala Thr Ile Leu Arg Asp Asn Gly Gln Ser Thr Val Arg
65                  70                  75                  80
Leu Gln Leu Ser Asn Leu Arg Ala Glu Asp Thr Gly Thr Tyr Tyr Cys
                85                  90                  95
Ala Lys Tyr Thr Gly Ser Ser Gly Ser Ile Gly Ala Trp Gly His
            100                 105                 110
Gly Thr Glu Val Ile Val Ser
            115

<210> SEQ ID NO 7
<211> LENGTH: 119
<212> TYPE: PRT
<213> ORGANISM: chicken

<400> SEQUENCE: 7

Ala Val Thr Leu Asp Glu Ser Gly Gly Gly Leu Gln Thr Pro Gly Gly
 1               5                  10                 15
Ala Leu Ser Leu Val Cys Lys Ala Ser Gly Phe Thr Phe Ser Thr Tyr
            20                  25                 30
Ala Met Gly Trp Met Arg Gln Ala Pro Gly Lys Gly Leu Glu Tyr Val
        35                  40                  45
Ala Ala Ile Arg Asn Asp Gly Ser Trp Thr Gly Tyr Gly Ala Ala Val
    50                  55                  60
Lys Gly Arg Ala Thr Ile Leu Arg Asp Asn Gly Gln Ser Thr Val Arg
65                  70                  75                  80
```

-continued

Leu Gln Leu Ser Asn Leu Arg Ala Glu Asp Thr Gly Thr Tyr Tyr Cys
            85                  90                  95

Ala Lys Tyr Thr Gly Ser Ser Gly Gly Ser Ile Gly Ala Trp Gly His
        100                 105                 110

Gly Thr Glu Val Ile Val Ser
        115

<210> SEQ ID NO 8
<211> LENGTH: 119
<212> TYPE: PRT
<213> ORGANISM: chicken

<400> SEQUENCE: 8

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Thr Tyr
            20                  25                  30

Ala Met Gly Trp Met Arg Gln Ala Pro Gly Lys Gly Leu Glu Tyr Val
        35                  40                  45

Ala Ala Ile Arg Asn Asp Gly Ser Trp Thr Gly Tyr Gly Ala Ala Val
    50                  55                  60

Lys Gly Arg Ala Thr Ile Leu Arg Asp Asn Gly Gln Ser Thr Val Arg
65                  70                  75                  80

Leu Gln Leu Ser Asn Leu Arg Ala Glu Asp Thr Gly Thr Tyr Tyr Cys
            85                  90                  95

Ala Lys Tyr Thr Gly Ser Ser Gly Ser Ile Gly Ala Trp Gly His
        100                 105                 110

Gly Thr Glu Val Ile Val Ser
        115

<210> SEQ ID NO 9
<211> LENGTH: 357
<212> TYPE: DNA
<213> ORGANISM: chicken

<400> SEQUENCE: 9
gcggtgacgt tggacgagtc cggggcggc ctccagacgc ccggaggagc gctcagcctc        60
gtctgcaagg cctccgggtt tgacttcagt agttatggca tgggatggat gcgccaggcg      120
cccggcaagg ggctggaata cgttgcagct attaggaatg atggcagttg acaggctac       180 ggggcggcgg tgaagggcca tgccaccatc tcgagggaca acgggcagag cacagtgagg      240
ctgcagctga caaccctcag ggctgaggac accggcacct actactgcgc caaaactact      300
ggtagtcgtg gtggtagcat cgacgcatgg ggccacggga ccgaagtcat cgtctcc         357

<210> SEQ ID NO 10
<211> LENGTH: 357
<212> TYPE: DNA
<213> ORGANISM: chicken

<400> SEQUENCE: 10
gcggtgacgt tggacgagtc cggggcggc ctccagacgc ccggaggaac gctcagcctc        60
gtctgcaagg gctccgggtt caccttcagt agttatggca tgggatggat gcgccaggcg      120
cccggcaagg ggctggaata cgttgcagct atcaggaatg atggtagttg acaggctac       180 gggtcggcgg tgaagggccg tgccaccatc tcgagggaca acgggcagag cacagtgagg      240
ctgcagttga caaccctcag ggctgaggac accgccacct actactgcgc caaaactagt      300

```
ggtagtagtg gtggtagcgt cgacgcatgg ggccacggga ccgaagtcat cgtctcc       357
```

<210> SEQ ID NO 11
<211> LENGTH: 357
<212> TYPE: PRT
<213> ORGANISM: chicken

<400> SEQUENCE: 11

```
Gly Cys Gly Gly Thr Gly Ala Cys Gly Thr Gly Gly Ala Cys Gly
1               5                   10                  15

Ala Gly Thr Cys Cys Gly Gly Gly Gly Cys Gly Gly Cys Cys Thr
                20                  25                  30

Cys Cys Ala Gly Ala Cys Gly Cys Cys Gly Gly Ala Gly Gly Ala
                35                  40                  45

Gly Cys Gly Cys Thr Cys Ala Gly Cys Cys Thr Cys Gly Thr Cys Thr
            50                  55                  60

Gly Cys Ala Ala Gly Gly Cys Cys Thr Cys Cys Gly Gly Thr Thr
65                  70                  75                  80

Cys Ala Cys Cys Thr Thr Cys Ala Gly Thr Ala Gly Thr Thr Ala Thr
                    85                  90                  95

Gly Gly Cys Ala Thr Gly Ala Gly Thr Gly Gly Thr Gly Cys
                100                 105                 110

Gly Ala Cys Ala Gly Cys Gly Cys Cys Gly Gly Cys Ala Ala
            115                 120                 125

Gly Gly Gly Gly Cys Thr Gly Gly Ala Ala Thr Ala Cys Gly Thr Thr
            130                 135                 140

Gly Cys Ala Gly Cys Thr Ala Thr Thr Ala Gly Ala Ala Thr Gly
145                 150                 155                 160

Ala Thr Gly Gly Thr Ala Gly Thr Thr Gly Gly Ala Cys Ala Gly Gly
                    165                 170                 175

Cys Thr Ala Cys Gly Gly Gly Cys Gly Gly Cys Gly Gly Thr Gly
                180                 185                 190

Ala Ala Gly Gly Gly Cys Cys Gly Thr Gly Cys Cys Ala Cys Cys Ala
            195                 200                 205

Thr Cys Thr Cys Gly Ala Gly Gly Gly Ala Cys Gly Ala Cys Gly Gly
        210                 215                 220

Gly Cys Ala Gly Ala Gly Cys Ala Cys Ala Cys Thr Gly Ala Gly Gly
225                 230                 235                 240

Cys Thr Gly Cys Ala Gly Cys Thr Gly Ala Ala Cys Ala Ala Cys Cys
                    245                 250                 255

Thr Cys Ala Gly Gly Cys Thr Gly Ala Gly Gly Ala Cys Ala Cys
                260                 265                 270

Cys Gly Cys Cys Ala Cys Thr Ala Cys Thr Ala Cys Thr Gly Cys
            275                 280                 285

Gly Cys Cys Ala Ala Ala Cys Thr Ala Cys Thr Gly Gly Thr Ala
            290                 295                 300

Gly Thr Ala Gly Thr Gly Gly Thr Gly Gly Thr Ala Gly Cys Ala Thr
305                 310                 315                 320

Cys Gly Ala Cys Gly Cys Ala Thr Gly Gly Gly Cys Cys Ala Cys
                325                 330                 335

Gly Gly Gly Ala Cys Cys Gly Ala Ala Gly Thr Cys Ala Thr Cys Gly
            340                 345                 350

Thr Cys Thr Cys Cys
                355
```

<210> SEQ ID NO 12
<211> LENGTH: 357
<212> TYPE: DNA
<213> ORGANISM: chicken

<400> SEQUENCE: 12

```
gcggtgacgt tggacgagtc cgggggcggc ctccagacgc ccggaggagc gctcagcctc    60
gtctgcaagg cctccgggtt caccttcagt acttatgcca tgggttggat gcgccaggca   120
cccggcaagg ggctggagta tgtcgcagct attaggaatg atggtagttg dacaggctac   180
ggggcggcgg tgaagggccg tgccaccatc ttgagggaca cgggcagag cacagtgagg    240
ctgcagctga gcaacctcag ggctgaggac accggcacct actactgcgc caaatatact   300
ggtagtagtg gtggtagcat cggcgcatgg ggccacggga ccgaagtcat cgtctcc      357
```

<210> SEQ ID NO 13
<211> LENGTH: 357
<212> TYPE: DNA
<213> ORGANISM: chicken

<400> SEQUENCE: 13

```
gccgtgacgt tggacgagtc cgggggcggc ctccagacgc ccggaggagc gctcagcctc    60
gtctgcaagg cctccgggtt caccttcagt acttatgcca tgggttggat gcgccaggca   120
cccggcaagg ggctggagta tgtcgcagct attaggaatg atggtagttg dacaggctac   180
ggggcggcgg tgaagggccg tgccaccatc ttgagggaca cgggcagag cacagtgagg    240
ctgcagctga gcaacctcag ggctgaggac accggcacct actactgcgc caaatatact   300
ggtagtagtg gtggtagcat cggcgcatgg ggccacggga ccgaagtcat cgtctcc      357
```

<210> SEQ ID NO 14
<211> LENGTH: 357
<212> TYPE: DNA
<213> ORGANISM: chicken

<400> SEQUENCE: 14

```
gcggtgacgt tggacgagtc cgggggcggc ctccagacgc ccggaggagc gctcagcctc    60
gtctgcaagg cctccgggtt caccttcagt acttatgcca tgggttggat gcgccaggca   120
cccggcaagg ggctggagta tgtcgcagct attaggaatg atggtagttg dacaggctac   180
ggggcggcgg tgaagggccg tgccaccatc ttgagggaca cgggcagag cacagtgagg    240
ctgcagctga gcaacctcag ggctgaggac accggcacct actactgcgc caaatatact   300
ggtagtagtg gtggtagcat cggcgcatgg ggccacggga ccgaagtcat cgtctcc      357
```

<210> SEQ ID NO 15
<211> LENGTH: 103
<212> TYPE: PRT
<213> ORGANISM: chicken

<400> SEQUENCE: 15

Ala Ser Thr Gln Pro Ser Ser Val Ser Ala Asn Leu Gly Gly Thr Val
1               5                   10                  15

Glu Ile Thr Cys Ser Gly Gly Gly Arg Tyr Tyr Tyr Gly Trp Tyr Gln
            20                  25                  30

Gln Lys Ser Pro Gly Ser Ala Pro Val Thr Val Ile Tyr Ala Asn Asp
        35                  40                  45

Lys Arg Pro Ser Asp Ile Pro Ser Arg Phe Ser Gly Ser Lys Ser Gly
    50                  55                  60

Ser Thr Gly Thr Leu Thr Ile Thr Gly Val Gln Ala Glu Asp Glu Ala
65                  70                  75                  80

Val Tyr Phe Cys Gly Ser Ala Glu Thr Ser Ser Tyr Val Phe Gly Ala
                85                  90                  95

Gly Thr Leu Thr Val Leu
            100

<210> SEQ ID NO 16
<211> LENGTH: 103
<212> TYPE: PRT
<213> ORGANISM: chicken

<400> SEQUENCE: 16

Ala Ser Thr Gln Pro Ser Ser Val Ser Ala Asn Leu Gly Gly Thr Val
1               5                   10                  15

Glu Ile Thr Cys Ser Gly Gly Arg Tyr Tyr Tyr Gly Trp Tyr Gln
                20                  25                  30

Gln Lys Ser Pro Gly Ser Ala Pro Val Thr Val Ile Tyr Ala Asn Asp
            35                  40                  45

Lys Arg Pro Ser Asp Ile Pro Ser Arg Phe Ser Gly Ser Lys Ser Gly
        50                  55                  60

Ser Thr Gly Thr Leu Thr Ile Thr Gly Val Gln Ala Glu Asp Glu Ala
65                  70                  75                  80

Val Tyr Phe Cys Gly Ser Ala Glu Thr Ser Ser Tyr Val Phe Gly Ala
                85                  90                  95

Gly Thr Leu Thr Val Leu
            100

<210> SEQ ID NO 17
<211> LENGTH: 103
<212> TYPE: PRT
<213> ORGANISM: chicken

<400> SEQUENCE: 17

Ala Ser Thr Gln Pro Ser Ser Val Ser Ala Asn Leu Gly Glu Thr Val
1               5                   10                  15

Lys Ile Thr Cys Ser Gly Gly Asn Tyr Tyr Tyr Gly Trp Tyr Gln
                20                  25                  30

Gln Lys Ser Pro Gly Ser Ala Pro Val Thr Leu Ile Tyr Ala Asn Asp
            35                  40                  45

Lys Arg Pro Ser Asn Ile Pro Ser Arg Phe Ser Gly Ser Lys Ser Gly
        50                  55                  60

Ser Thr Gly Thr Leu Thr Ile Thr Gly Val Gln Ala Glu Asp Glu Ala
65                  70                  75                  80

Val Tyr Phe Cys Gly Thr Ala Asp Thr Gly Lys Tyr Val Phe Gly Ala
                85                  90                  95

Gly Thr Thr Leu Thr Val Leu
            100

<210> SEQ ID NO 18
<211> LENGTH: 104
<212> TYPE: PRT
<213> ORGANISM: chicken

<400> SEQUENCE: 18

Ala Ser Thr Gln Pro Ser Ser Val Ser Ala Asn Leu Gly Gly Thr Val
1               5                   10                  15

```
Glu Ile Thr Cys Ser Gly Gly Asn Arg Asn Tyr Tyr Tyr Gly Trp Tyr
                20                  25                  30

Gln Gln Lys Ser Pro Gly Ser Ala Pro Val Thr Leu Ile Tyr Ala Asn
            35                  40                  45

Asp Lys Arg Pro Ser Asn Ile Pro Ser Arg Phe Ser Gly Ser Lys Ser
 50                  55                  60

Gly Ser Thr Gly Thr Leu Thr Ile Thr Gly Val Gln Ala Glu Asp Glu
 65                  70                  75                  80

Ala Val Tyr Phe Cys Gly Thr Ala Asp Thr Gly Lys Tyr Val Phe Gly
                85                  90                  95

Ala Gly Thr Thr Leu Thr Val Leu
            100
```

<210> SEQ ID NO 19
<211> LENGTH: 103
<212> TYPE: PRT
<213> ORGANISM: chicken

<400> SEQUENCE: 19

```
Ala Val Thr Gln Pro Ala Ser Val Ser Ala Asn Leu Gly Gly Thr Val
1               5                   10                  15

Glu Ile Thr Cys Ser Gly Gly Arg Tyr Tyr Tyr Gly Trp Tyr Gln
                20                  25                  30

Gln Lys Ser Pro Gly Ser Ala Pro Val Thr Val Ile Tyr Ala Asn Asp
            35                  40                  45

Lys Arg Pro Ser Asp Ile Pro Ser Arg Phe Ser Gly Ser Lys Ser Gly
 50                  55                  60

Ser Thr Gly Thr Leu Thr Ile Thr Gly Val Gln Ala Glu Asp Glu Ala
65                  70                  75                  80

Val Tyr Phe Cys Gly Ser Ala Glu Thr Ser Ser Tyr Val Phe Gly Ala
                85                  90                  95

Gly Thr Thr Leu Thr Val Leu
            100
```

<210> SEQ ID NO 20
<211> LENGTH: 104
<212> TYPE: PRT
<213> ORGANISM: chicken

<400> SEQUENCE: 20

```
Ala Ser Thr Gln Pro Ser Ser Val Ser Ala Asn Pro Gly Gly Thr Val
1               5                   10                  15

Glu Ile Thr Cys Ser Gly Gly Ser Gly Arg Tyr Tyr Tyr Gly Trp Tyr
                20                  25                  30

Gln Gln Lys Ser Pro Gly Ser Ala Pro Val Thr Val Ile Tyr Ser Ser
            35                  40                  45

Thr His Arg Pro Ser Asn Ile Pro Ser Arg Phe Ser Gly Ser Lys Ser
 50                  55                  60

Gly Ser Thr Ala Thr Leu Thr Ile Thr Gly Val Gln Ala Glu Asp Glu
 65                  70                  75                  80

Ala Val Tyr Phe Cys Gly Thr Ala Asp Ser Ser Tyr Val Phe Gly
                85                  90                  95

Ala Gly Thr Thr Leu Thr Val Leu
            100
```

<210> SEQ ID NO 21
<211> LENGTH: 309

<212> TYPE: DNA
<213> ORGANISM: chicken

<400> SEQUENCE: 21
gctagcactc agccgtcctc ggtgtcagca aacctgggag gaaccgtcga gatcacctgc        60
tccgggggtg gcaggtacta ttatggctgg taccagcaga agtctcctgg cagtgccct       120 gtcactgtga tctatgctaa cgacaagaga ccctcggaca tcccttcacg attctccggt      180
tccaaatccg gctccacggg cacattgacc atcactgggg tccaagccga ggacgaggct      240
gtctatttct gtgggagtgc agagaccagc agctatgtat ttggggccgg gacaaccctg      300
accgtccta                                                              309

<210> SEQ ID NO 22
<211> LENGTH: 309
<212> TYPE: DNA
<213> ORGANISM: chicken

<400> SEQUENCE: 22
gctagcactc agccgtcctc ggtgtcagca aacctgggag gaaccgtcga gatcacctgc        60
tccgggggtg gcaggtacta ttatggctgg taccagcaga agtctcctgg cagtgccct       120 gtcactgtga tctatgctaa cgacaagaga ccctcggaca tcccttcacg attctccggt      180
tccaaatccg gctccacggg cacattgacc atcactgggg tccaagccga agacgaggct      240
gtctatttct gtgggagtgc agagaccagc agctatgtat ttggggccgg gacaaccctg      300
accgtccta                                                              309

<210> SEQ ID NO 23
<211> LENGTH: 309
<212> TYPE: DNA
<213> ORGANISM: chicken

<400> SEQUENCE: 23
gctagcactc agccgtcctc ggtgtcagca aaccgggag aaaccgtcaa gatcacctgc         60
tccgggggtg gcaattatta ctatggctgg taccagcaga agtcacctgg cagtgccct        120 gtcactctga tctatgctaa cgacaagaga ccctcgaaca tcccttcacg attctccggt      180
tccaaatccg gctccacagg cacattaacc atcactgggg tccaagccga ggacgaggct      240
gtctatttct gtgggaccgc agacaccggg aagtatgtat ttggggccgg gacaaccctg      300
accgtccta                                                              309

<210> SEQ ID NO 24
<211> LENGTH: 312
<212> TYPE: DNA
<213> ORGANISM: chicken

<400> SEQUENCE: 24
gctagcactc agccgtcctc ggtgtcagca aacctgggag gaaccgtcga gatcacctgc        60
tccgggggga ataggaacta ctactatggc tggtaccagc agaagtcacc tggcagtgcc      120
cctgtcactc tgatctatgc taacgacaag agaccctcga acatcccttc acgattctcc      180
ggttccaaat ccggctccac aggcacatta accatcactg ggtccaagc cgaggacgag       240 gctgtctatt tctgtgggac cgcagacacc gggaagtatg tatttggggc cgggacaacc      300
ctgaccgtcc ta                                                          312

<210> SEQ ID NO 25

```
<211> LENGTH: 309
<212> TYPE: DNA
<213> ORGANISM: chicken

<400> SEQUENCE: 25
gcagtgactc agccggcctc agtgtcagca aacctgggag gaaccgtcga gatcacctgc        60 tccggggtg gcaggtacta ttatggctgg taccagcaga agtctcctgg cagtgcccct       120
gtcactgtga tctatgctaa cgacaagaga ccctcggaca tcccttcacg attctccggt       180
tccaaatccg gctccacggg cacattgacc atcactgggg tccaagcaga ggacgaggct       240
gtctatttct gtgggagtgc agagaccagc agctatgtat ttggggccgg acaaccctg       300 accgtcctc                                                               309

<210> SEQ ID NO 26
<211> LENGTH: 312
<212> TYPE: DNA
<213> ORGANISM: chicken

<400> SEQUENCE: 26
gctagcactc agccgtcctc ggtgtcagca aacccaggag gaaccgtcga gatcacctgc        60
tccgggggta gtggcaggta ctattatggc tggtaccagc agaagtctcc tggcagtgcc       120
cctgtcactg tgatctatag cagcacccac agaccctcaa acatcccttc acgattctcc       180
ggttccaaat ccggctccac ggccacatta ccatcactg gggtccaagc cgaggacgag       240
gctgtctatt tctgtgggac tgcagacagc agcagctatg tctttggggc cgggacaacc       300
ctgaccgtcc ta                                                           312

<210> SEQ ID NO 27
<211> LENGTH: 17
<212> TYPE: PRT
<213> ORGANISM: Artificial Sequence
<220> FEATURE:
<223> OTHER INFORMATION: peptide

<400> SEQUENCE: 27

Ala Glu Asn Met Asp Asp Gln Trp Met Gln Asp Glu Met Glu Ile Gly
1               5                   10                  15

Tyr

<210> SEQ ID NO 28
<211> LENGTH: 17
<212> TYPE: PRT
<213> ORGANISM: Artificial Sequence
<220> FEATURE:
<223> OTHER INFORMATION: peptide

<400> SEQUENCE: 28

Glu Ala Asn Met Asp Asp Gln Trp Met Gln Asp Glu Met Glu Ile Gly
1               5                   10                  15

Tyr

<210> SEQ ID NO 29
<211> LENGTH: 17
<212> TYPE: PRT
<213> ORGANISM: Artificial Sequence
<220> FEATURE:
<223> OTHER INFORMATION: peptide

<400> SEQUENCE: 29

Glu Glu Ala Met Asp Asp Gln Trp Met Gln Asp Glu Met Glu Ile Gly
```

<210> SEQ ID NO 30
<211> LENGTH: 17
<212> TYPE: PRT
<213> ORGANISM: Artificial Sequence
<220> FEATURE:
<223> OTHER INFORMATION: peptide

<400> SEQUENCE: 30

Glu Glu Asn Ala Asp Asp Gln Trp Met Gln Asp Glu Met Glu Ile Gly
1               5                   10                  15
Tyr

<210> SEQ ID NO 31
<211> LENGTH: 17
<212> TYPE: PRT
<213> ORGANISM: Artificial Sequence
<220> FEATURE:
<223> OTHER INFORMATION: peptide

<400> SEQUENCE: 31

Glu Glu Asn Met Ala Asp Gln Trp Met Gln Asp Glu Met Glu Ile Gly
1               5                   10                  15
Tyr

<210> SEQ ID NO 32
<211> LENGTH: 17
<212> TYPE: PRT
<213> ORGANISM: Artificial Sequence
<220> FEATURE:
<223> OTHER INFORMATION: peptide

<400> SEQUENCE: 32

Glu Glu Asn Met Asp Ala Gln Trp Met Gln Asp Glu Met Glu Ile Gly
1               5                   10                  15
Tyr

<210> SEQ ID NO 33
<211> LENGTH: 17
<212> TYPE: PRT
<213> ORGANISM: Artificial Sequence
<220> FEATURE:
<223> OTHER INFORMATION: peptide

<400> SEQUENCE: 33

Glu Glu Asn Met Asp Asp Ala Trp Met Gln Asp Glu Met Glu Ile Gly
1               5                   10                  15
Tyr

<210> SEQ ID NO 34
<211> LENGTH: 17
<212> TYPE: PRT
<213> ORGANISM: Artificial Sequence
<220> FEATURE:
<223> OTHER INFORMATION: peptide

<400> SEQUENCE: 34

Glu Glu Asn Met Asp Asp Gln Ala Met Gln Asp Glu Met Glu Ile Gly
1               5                   10                  15
Tyr

```
<210> SEQ ID NO 35
<211> LENGTH: 17
<212> TYPE: PRT
<213> ORGANISM: Artificial Sequence
<220> FEATURE:
<223> OTHER INFORMATION: peptide

<400> SEQUENCE: 35

Glu Glu Asn Met Asp Asp Gln Trp Ala Gln Asp Glu Met Glu Ile Gly
1               5                   10                  15

Tyr

<210> SEQ ID NO 36
<211> LENGTH: 17
<212> TYPE: PRT
<213> ORGANISM: Artificial Sequence
<220> FEATURE:
<223> OTHER INFORMATION: peptide

<400> SEQUENCE: 36

Glu Glu Asn Met Asp Asp Gln Trp Met Ala Asp Glu Met Glu Ile Gly
1               5                   10                  15

Tyr

<210> SEQ ID NO 37
<211> LENGTH: 17
<212> TYPE: PRT
<213> ORGANISM: Artificial Sequence
<220> FEATURE:
<223> OTHER INFORMATION: peptide

<400> SEQUENCE: 37

Glu Glu Asn Met Asp Asp Gln Trp Met Gln Ala Glu Met Glu Ile Gly
1               5                   10                  15

Tyr

<210> SEQ ID NO 38
<211> LENGTH: 17
<212> TYPE: PRT
<213> ORGANISM: Artificial Sequence
<220> FEATURE:
<223> OTHER INFORMATION: peptide

<400> SEQUENCE: 38

Glu Glu Asn Met Asp Asp Gln Trp Met Gln Asp Ala Met Glu Ile Gly
1               5                   10                  15

Tyr

<210> SEQ ID NO 39
<211> LENGTH: 17
<212> TYPE: PRT
<213> ORGANISM: Artificial Sequence
<220> FEATURE:
<223> OTHER INFORMATION: peptide

<400> SEQUENCE: 39

Glu Glu Asn Met Asp Asp Gln Trp Met Gln Asp Glu Ala Glu Ile Gly
1               5                   10                  15

Tyr

<210> SEQ ID NO 40
<211> LENGTH: 17
<212> TYPE: PRT
```

```
<213> ORGANISM: Artificial Sequence
<220> FEATURE:
<223> OTHER INFORMATION: peptide

<400> SEQUENCE: 40

Glu Glu Asn Met Asp Asp Gln Trp Met Gln Asp Glu Met Ala Ile Gly
1               5                   10                  15

Tyr

<210> SEQ ID NO 41
<211> LENGTH: 17
<212> TYPE: PRT
<213> ORGANISM: Artificial Sequence
<220> FEATURE:
<223> OTHER INFORMATION: peptide

<400> SEQUENCE: 41

Glu Glu Asn Met Asp Asp Gln Trp Met Gln Asp Glu Met Glu Ala Gly
1               5                   10                  15

Tyr

<210> SEQ ID NO 42
<211> LENGTH: 17
<212> TYPE: PRT
<213> ORGANISM: Artificial Sequence
<220> FEATURE:
<223> OTHER INFORMATION: peptide

<400> SEQUENCE: 42

Glu Glu Asn Met Asp Asp Gln Trp Met Gln Asp Glu Met Glu Ile Ala
1               5                   10                  15

Tyr

<210> SEQ ID NO 43
<211> LENGTH: 17
<212> TYPE: PRT
<213> ORGANISM: Artificial Sequence
<220> FEATURE:
<223> OTHER INFORMATION: peptide

<400> SEQUENCE: 43

Glu Glu Asn Met Asp Asp Gln Trp Met Gln Asp Glu Met Glu Ile Gly
1               5                   10                  15

Ala

<210> SEQ ID NO 44
<211> LENGTH: 17
<212> TYPE: PRT
<213> ORGANISM: Artificial Sequence
<220> FEATURE:
<223> OTHER INFORMATION: peptide

<400> SEQUENCE: 44

Ala Ala Ala Met Asp Asp Gln Trp Met Gln Asp Glu Met Glu Ile Gly
1               5                   10                  15

Tyr

<210> SEQ ID NO 45
<211> LENGTH: 17
<212> TYPE: PRT
<213> ORGANISM: Artificial Sequence
<220> FEATURE:
<223> OTHER INFORMATION: peptide
```

```
<400> SEQUENCE: 45

Glu Glu Asn Ala Ala Ala Gln Trp Met Gln Asp Glu Met Glu Ile Gly
1               5                   10                  15

Tyr

<210> SEQ ID NO 46
<211> LENGTH: 17
<212> TYPE: PRT
<213> ORGANISM: Artificial Sequence
<220> FEATURE:
<223> OTHER INFORMATION: peptide

<400> SEQUENCE: 46

Glu Glu Asn Met Asp Asp Ala Ala Ala Gln Asp Glu Met Glu Ile Gly
1               5                   10                  15

Tyr

<210> SEQ ID NO 47
<211> LENGTH: 17
<212> TYPE: PRT
<213> ORGANISM: Artificial Sequence
<220> FEATURE:
<223> OTHER INFORMATION: peptide

<400> SEQUENCE: 47

Glu Glu Asn Met Asp Asp Gln Trp Met Ala Ala Ala Met Glu Ile Gly
1               5                   10                  15

Tyr

<210> SEQ ID NO 48
<211> LENGTH: 17
<212> TYPE: PRT
<213> ORGANISM: Artificial Sequence
<220> FEATURE:
<223> OTHER INFORMATION: peptide

<400> SEQUENCE: 48

Glu Glu Asn Met Asp Asp Gln Trp Met Gln Asp Glu Ala Ala Ala Gly
1               5                   10                  15

Tyr

<210> SEQ ID NO 49
<211> LENGTH: 17
<212> TYPE: PRT
<213> ORGANISM: Artificial Sequence
<220> FEATURE:
<223> OTHER INFORMATION: peptide

<400> SEQUENCE: 49

Glu Glu Asn Met Asp Asp Gln Trp Met Gln Asp Glu Met Glu Ile Ala
1               5                   10                  15

Ala

<210> SEQ ID NO 50
<211> LENGTH: 5
<212> TYPE: PRT
<213> ORGANISM: chicken

<400> SEQUENCE: 50

Ser Tyr Gly Met Gly
1               5
```

```
<210> SEQ ID NO 51
<211> LENGTH: 17
<212> TYPE: PRT
<213> ORGANISM: chicken

<400> SEQUENCE: 51

Ala Ile Arg Asn Asp Gly Ser Trp Thr Gly Tyr Gly Ala Ala Val Lys
1               5                   10                  15

Gly

<210> SEQ ID NO 52
<211> LENGTH: 11
<212> TYPE: PRT
<213> ORGANISM: chicken

<400> SEQUENCE: 52

Thr Thr Gly Ser Arg Gly Gly Ser Ile Asp Ala
1               5                   10

<210> SEQ ID NO 53
<211> LENGTH: 9
<212> TYPE: PRT
<213> ORGANISM: chicken

<400> SEQUENCE: 53

Ser Gly Gly Gly Arg Tyr Tyr Tyr Gly
1               5

<210> SEQ ID NO 54
<211> LENGTH: 7
<212> TYPE: PRT
<213> ORGANISM: chicken

<400> SEQUENCE: 54

Ala Asn Asp Lys Arg Pro Ser
1               5

<210> SEQ ID NO 55
<211> LENGTH: 9
<212> TYPE: PRT
<213> ORGANISM: chicken

<400> SEQUENCE: 55

Gly Ser Ala Glu Thr Ser Ser Tyr Val
1               5

<210> SEQ ID NO 56
<211> LENGTH: 5
<212> TYPE: PRT
<213> ORGANISM: chicken

<400> SEQUENCE: 56

Ser Tyr Gly Met Gly
1               5

<210> SEQ ID NO 57
<211> LENGTH: 17
<212> TYPE: PRT
<213> ORGANISM: chicken

<400> SEQUENCE: 57

Ala Ile Arg Asn Asp Gly Ser Trp Thr Gly Tyr Gly Ser Ala Val Lys
1               5                   10                  15

Gly
```

<210> SEQ ID NO 58
<211> LENGTH: 11
<212> TYPE: PRT
<213> ORGANISM: chicken

<400> SEQUENCE: 58

Thr Ser Gly Ser Ser Gly Gly Ser Val Asp Ala
1               5                   10

<210> SEQ ID NO 59
<211> LENGTH: 9
<212> TYPE: PRT
<213> ORGANISM: chicken

<400> SEQUENCE: 59

Ser Gly Gly Gly Arg Tyr Tyr Tyr Gly
1               5

<210> SEQ ID NO 60
<211> LENGTH: 7
<212> TYPE: PRT
<213> ORGANISM: chicken

<400> SEQUENCE: 60

Ala Asn Asp Lys Arg Pro Ser
1               5

<210> SEQ ID NO 61
<211> LENGTH: 9
<212> TYPE: PRT
<213> ORGANISM: chicken

<400> SEQUENCE: 61

Gly Ser Ala Glu Thr Ser Ser Tyr Val
1               5

<210> SEQ ID NO 62
<211> LENGTH: 5
<212> TYPE: PRT
<213> ORGANISM: chicken

<400> SEQUENCE: 62

Ser Tyr Gly Met Glu
1               5

<210> SEQ ID NO 63
<211> LENGTH: 17
<212> TYPE: PRT
<213> ORGANISM: chicken

<400> SEQUENCE: 63

Ala Ile Arg Asn Asp Gly Ser Trp Thr Gly Tyr Gly Ala Ala Val Lys
1               5                   10                  15

Gly

<210> SEQ ID NO 64
<211> LENGTH: 11
<212> TYPE: PRT
<213> ORGANISM: chicken

<400> SEQUENCE: 64

Thr Thr Gly Ser Ser Gly Gly Ser Ile Asp Ala
1               5                   10

```
<210> SEQ ID NO 65
<211> LENGTH: 9
<212> TYPE: PRT
<213> ORGANISM: chicken

<400> SEQUENCE: 65

Ser Gly Gly Gly Asn Tyr Tyr Tyr Gly
1               5

<210> SEQ ID NO 66
<211> LENGTH: 7
<212> TYPE: PRT
<213> ORGANISM: chicken

<400> SEQUENCE: 66

Ala Asn Asp Lys Arg Pro Ser
1               5

<210> SEQ ID NO 67
<211> LENGTH: 9
<212> TYPE: PRT
<213> ORGANISM: chicken

<400> SEQUENCE: 67

Gly Thr Ala Asp Thr Gly Lys Tyr Val
1               5

<210> SEQ ID NO 68
<211> LENGTH: 5
<212> TYPE: PRT
<213> ORGANISM: chicken

<400> SEQUENCE: 68

Thr Tyr Ala Met Gly
1               5

<210> SEQ ID NO 69
<211> LENGTH: 17
<212> TYPE: PRT
<213> ORGANISM: chicken

<400> SEQUENCE: 69

Ala Ile Arg Asn Asp Gly Ser Trp Thr Gly Tyr Gly Ala Ala Val Lys
1               5                   10                  15

Gly

<210> SEQ ID NO 70
<211> LENGTH: 11
<212> TYPE: PRT
<213> ORGANISM: chicken

<400> SEQUENCE: 70

Tyr Thr Gly Ser Ser Gly Gly Ser Ile Gly Ala
1               5                   10

<210> SEQ ID NO 71
<211> LENGTH: 10
<212> TYPE: PRT
<213> ORGANISM: chicken

<400> SEQUENCE: 71

Ser Gly Gly Asn Arg Asn Tyr Tyr Tyr Gly
1               5                   10
```

<210> SEQ ID NO 72
<211> LENGTH: 7
<212> TYPE: PRT
<213> ORGANISM: chicken

<400> SEQUENCE: 72

Ala Asn Asp Lys Arg Pro Ser
1               5

<210> SEQ ID NO 73
<211> LENGTH: 9
<212> TYPE: PRT
<213> ORGANISM: chicken

<400> SEQUENCE: 73

Gly Thr Ala Asp Thr Gly Lys Tyr Val
1               5

<210> SEQ ID NO 74
<211> LENGTH: 5
<212> TYPE: PRT
<213> ORGANISM: chicken

<400> SEQUENCE: 74

Thr Tyr Ala Met Gly
1               5

<210> SEQ ID NO 75
<211> LENGTH: 17
<212> TYPE: PRT
<213> ORGANISM: chicken

<400> SEQUENCE: 75

Ala Ile Arg Asn Asp Gly Ser Trp Thr Gly Tyr Gly Ala Ala Val Lys
1               5                   10                  15
Gly

<210> SEQ ID NO 76
<211> LENGTH: 11
<212> TYPE: PRT
<213> ORGANISM: chicken

<400> SEQUENCE: 76

Tyr Thr Gly Ser Ser Gly Gly Ser Ile Gly Ala
1               5                   10

<210> SEQ ID NO 77
<211> LENGTH: 9
<212> TYPE: PRT
<213> ORGANISM: chicken

<400> SEQUENCE: 77

Ser Gly Gly Gly Arg Tyr Tyr Tyr Gly
1               5

<210> SEQ ID NO 78
<211> LENGTH: 7
<212> TYPE: PRT
<213> ORGANISM: chicken

<400> SEQUENCE: 78

Ala Asn Asp Lys Arg Pro Ser
1               5

<210> SEQ ID NO 79
<211> LENGTH: 9
<212> TYPE: PRT
<213> ORGANISM: chicken

<400> SEQUENCE: 79

Gly Ser Ala Glu Thr Ser Ser Tyr Val
1               5

<210> SEQ ID NO 80
<211> LENGTH: 5
<212> TYPE: PRT
<213> ORGANISM: chicken

<400> SEQUENCE: 80

Thr Tyr Ala Met Gly
1               5

<210> SEQ ID NO 81
<211> LENGTH: 17
<212> TYPE: PRT
<213> ORGANISM: chicken

<400> SEQUENCE: 81

Ala Ile Arg Asn Asp Gly Ser Trp Thr Gly Tyr Gly Ala Ala Val Lys
1               5                   10                  15

Gly

<210> SEQ ID NO 82
<211> LENGTH: 11
<212> TYPE: PRT
<213> ORGANISM: chicken

<400> SEQUENCE: 82

Tyr Thr Gly Ser Ser Gly Gly Ser Ile Gly Ala
1               5                   10

<210> SEQ ID NO 83
<211> LENGTH: 10
<212> TYPE: PRT
<213> ORGANISM: chicken

<400> SEQUENCE: 83

Ser Gly Gly Ser Gly Arg Tyr Tyr Tyr Gly
1               5                   10

<210> SEQ ID NO 84
<211> LENGTH: 7
<212> TYPE: PRT
<213> ORGANISM: chicken

<400> SEQUENCE: 84

Ser Ser Thr His Arg Pro Ser
1               5

<210> SEQ ID NO 85
<211> LENGTH: 9
<212> TYPE: PRT
<213> ORGANISM: chicken

<400> SEQUENCE: 85

Gly Thr Ala Asp Ser Ser Ser Tyr Val
1               5

<210> SEQ ID NO 86
<211> LENGTH: 30
<212> TYPE: PRT
<213> ORGANISM: chicken

<400> SEQUENCE: 86

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Asp Phe Ser
            20                  25                  30

<210> SEQ ID NO 87
<211> LENGTH: 14
<212> TYPE: PRT
<213> ORGANISM: chicken

<400> SEQUENCE: 87

Trp Met Arg Gln Ala Pro Gly Lys Gly Leu Glu Tyr Val Ala
1               5                   10

<210> SEQ ID NO 88
<211> LENGTH: 32
<212> TYPE: PRT
<213> ORGANISM: chicken

<400> SEQUENCE: 88

His Ala Thr Ile Ser Arg Asp Asn Gly Gln Ser Thr Val Arg Leu Gln
1               5                   10                  15

Leu Asn Asn Leu Arg Ala Glu Asp Thr Gly Thr Tyr Tyr Cys Ala Lys
            20                  25                  30

<210> SEQ ID NO 89
<211> LENGTH: 10
<212> TYPE: PRT
<213> ORGANISM: chicken

<400> SEQUENCE: 89

Trp Gly His Gly Thr Glu Val Ile Val Ser
1               5                   10

<210> SEQ ID NO 90
<211> LENGTH: 20
<212> TYPE: PRT
<213> ORGANISM: chicken

<400> SEQUENCE: 90

Ala Ser Thr Gln Pro Ser Ser Val Ser Ala Asn Leu Gly Gly Thr Val
1               5                   10                  15

Glu Ile Thr Cys
            20

<210> SEQ ID NO 91
<211> LENGTH: 16
<212> TYPE: PRT
<213> ORGANISM: chicken

<400> SEQUENCE: 91

Trp Tyr Gln Gln Lys Ser Pro Gly Ser Ala Pro Val Thr Val Ile Tyr
1               5                   10                  15

<210> SEQ ID NO 92
<211> LENGTH: 31

```
<212> TYPE: PRT
<213> ORGANISM: chicken

<400> SEQUENCE: 92

Asp Ile Pro Ser Arg Phe Ser Gly Ser Lys Ser Gly Ser Thr Gly Thr
1               5                   10                  15

Leu Thr Ile Thr Gly Val Gln Ala Glu Asp Glu Ala Val Tyr Phe
            20                  25                  30

<210> SEQ ID NO 93
<211> LENGTH: 10
<212> TYPE: PRT
<213> ORGANISM: chicken

<400> SEQUENCE: 93

Phe Gly Ala Gly Thr Thr Leu Thr Val Leu
1               5                   10

<210> SEQ ID NO 94
<211> LENGTH: 30
<212> TYPE: PRT
<213> ORGANISM: chicken

<400> SEQUENCE: 94

Ala Val Thr Leu Asp Glu Ser Gly Gly Leu Gln Thr Pro Gly Gly
1               5                   10                  15

Thr Leu Ser Leu Val Cys Lys Gly Ser Gly Phe Thr Phe Ser
            20                  25                  30

<210> SEQ ID NO 95
<211> LENGTH: 14
<212> TYPE: PRT
<213> ORGANISM: chicken

<400> SEQUENCE: 95

Trp Met Arg Gln Ala Pro Gly Lys Gly Leu Glu Tyr Val Ala
1               5                   10

<210> SEQ ID NO 96
<211> LENGTH: 32
<212> TYPE: PRT
<213> ORGANISM: chicken

<400> SEQUENCE: 96

Arg Ala Thr Ile Ser Arg Asp Asn Gly Gln Ser Thr Val Arg Leu Gln
1               5                   10                  15

Leu Asn Asn Leu Arg Ala Glu Asp Thr Ala Thr Tyr Tyr Cys Ala Lys
            20                  25                  30

<210> SEQ ID NO 97
<211> LENGTH: 10
<212> TYPE: PRT
<213> ORGANISM: chicken

<400> SEQUENCE: 97

Trp Gly His Gly Thr Glu Val Ile Val Ser
1               5                   10

<210> SEQ ID NO 98
<211> LENGTH: 20
<212> TYPE: PRT
<213> ORGANISM: chicken

<400> SEQUENCE: 98
```

```
Ala Ser Thr Gln Pro Ser Ser Val Ser Ala Asn Leu Gly Gly Thr Val
1               5                   10                  15

Glu Ile Thr Cys
            20
```

<210> SEQ ID NO 99
<211> LENGTH: 16
<212> TYPE: PRT
<213> ORGANISM: chicken

<400> SEQUENCE: 99

```
Trp Tyr Gln Gln Lys Ser Pro Gly Ser Ala Pro Val Thr Val Ile Tyr
1               5                   10                  15
```

<210> SEQ ID NO 100
<211> LENGTH: 32
<212> TYPE: PRT
<213> ORGANISM: chicken

<400> SEQUENCE: 100

```
Asp Ile Pro Ser Arg Phe Ser Gly Ser Lys Ser Gly Ser Thr Gly Thr
1               5                   10                  15

Leu Thr Ile Thr Gly Val Gln Ala Glu Asp Glu Ala Val Tyr Phe Cys
            20                  25                  30
```

<210> SEQ ID NO 101
<211> LENGTH: 10
<212> TYPE: PRT
<213> ORGANISM: chicken

<400> SEQUENCE: 101

```
Phe Gly Ala Gly Thr Thr Leu Thr Val Leu
1               5                   10
```

<210> SEQ ID NO 102
<211> LENGTH: 30
<212> TYPE: PRT
<213> ORGANISM: chicken

<400> SEQUENCE: 102

```
Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser
            20                  25                  30
```

<210> SEQ ID NO 103
<211> LENGTH: 14
<212> TYPE: PRT
<213> ORGANISM: chicken

<400> SEQUENCE: 103

```
Trp Val Arg Gln Ala Pro Gly Lys Gly Leu Glu Tyr Val Ala
1               5                   10
```

<210> SEQ ID NO 104
<211> LENGTH: 32
<212> TYPE: PRT
<213> ORGANISM: chicken

<400> SEQUENCE: 104

```
Arg Ala Thr Ile Ser Arg Asp Asp Gly Gln Ser Thr Leu Arg Leu Gln
1               5                   10                  15
```

-continued

Leu Asn Asn Leu Arg Ala Glu Asp Thr Ala Thr Tyr Tyr Cys Ala Lys
            20                  25                  30

<210> SEQ ID NO 105
<211> LENGTH: 10
<212> TYPE: PRT
<213> ORGANISM: chicken

<400> SEQUENCE: 105

Trp Gly His Gly Thr Glu Val Ile Val Ser
1               5                   10

<210> SEQ ID NO 106
<211> LENGTH: 20
<212> TYPE: PRT
<213> ORGANISM: chicken

<400> SEQUENCE: 106

Ala Ser Thr Gln Pro Ser Ser Val Ser Ala Asn Leu Gly Glu Thr Val
1               5                   10                  15

Lys Ile Thr Cys
            20

<210> SEQ ID NO 107
<211> LENGTH: 16
<212> TYPE: PRT
<213> ORGANISM: chicken

<400> SEQUENCE: 107

Trp Tyr Gln Gln Lys Ser Pro Gly Ser Ala Pro Val Thr Leu Ile Tyr
1               5                   10                  15

<210> SEQ ID NO 108
<211> LENGTH: 32
<212> TYPE: PRT
<213> ORGANISM: chicken

<400> SEQUENCE: 108

Asn Ile Pro Ser Arg Phe Ser Gly Ser Lys Ser Gly Ser Thr Gly Thr
1               5                   10                  15

Leu Thr Ile Thr Gly Val Gln Ala Glu Asp Glu Ala Val Tyr Phe Cys
            20                  25                  30

<210> SEQ ID NO 109
<211> LENGTH: 10
<212> TYPE: PRT
<213> ORGANISM: chicken

<400> SEQUENCE: 109

Phe Gly Ala Gly Thr Thr Leu Thr Val Leu
1               5                   10

<210> SEQ ID NO 110
<211> LENGTH: 30
<212> TYPE: PRT
<213> ORGANISM: chicken

<400> SEQUENCE: 110

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser
            20                  25                  30

```
<210> SEQ ID NO 111
<211> LENGTH: 14
<212> TYPE: PRT
<213> ORGANISM: chicken

<400> SEQUENCE: 111

Trp Met Arg Gln Ala Pro Gly Lys Gly Leu Glu Tyr Val Ala
1               5                   10

<210> SEQ ID NO 112
<211> LENGTH: 32
<212> TYPE: PRT
<213> ORGANISM: chicken

<400> SEQUENCE: 112

Arg Ala Thr Ile Leu Arg Asp Asn Gly Gln Ser Thr Val Arg Leu Gln
1               5                   10                  15

Leu Ser Asn Leu Arg Ala Glu Asp Thr Gly Thr Tyr Tyr Cys Ala Lys
            20                  25                  30

<210> SEQ ID NO 113
<211> LENGTH: 10
<212> TYPE: PRT
<213> ORGANISM: chicken

<400> SEQUENCE: 113

Trp Gly His Gly Thr Glu Val Ile Val Ser
1               5                   10

<210> SEQ ID NO 114
<211> LENGTH: 19
<212> TYPE: PRT
<213> ORGANISM: chicken

<400> SEQUENCE: 114

Ala Ser Thr Gln Pro Ser Ser Val Ser Ala Asn Leu Gly Gly Thr Val
1               5                   10                  15

Glu Ile Thr

<210> SEQ ID NO 115
<211> LENGTH: 16
<212> TYPE: PRT
<213> ORGANISM: chicken

<400> SEQUENCE: 115

Trp Tyr Gln Gln Lys Ser Pro Gly Ser Ala Pro Val Thr Leu Ile Tyr
1               5                   10                  15

<210> SEQ ID NO 116
<211> LENGTH: 31
<212> TYPE: PRT
<213> ORGANISM: chicken

<400> SEQUENCE: 116

Asn Ile Pro Ser Arg Phe Ser Gly Ser Lys Ser Gly Ser Thr Gly Thr
1               5                   10                  15

Leu Thr Ile Thr Gly Val Gln Ala Glu Asp Glu Ala Val Tyr Phe
            20                  25                  30

<210> SEQ ID NO 117
<211> LENGTH: 10
<212> TYPE: PRT
<213> ORGANISM: chicken
```

<400> SEQUENCE: 117

Phe Gly Ala Gly Thr Thr Leu Thr Val Leu
1               5                   10

<210> SEQ ID NO 118
<211> LENGTH: 30
<212> TYPE: PRT
<213> ORGANISM: chicken

<400> SEQUENCE: 118

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser
            20                  25                  30

<210> SEQ ID NO 119
<211> LENGTH: 14
<212> TYPE: PRT
<213> ORGANISM: chicken

<400> SEQUENCE: 119

Trp Met Arg Gln Ala Pro Gly Lys Gly Leu Glu Tyr Val Ala
1               5                   10

<210> SEQ ID NO 120
<211> LENGTH: 32
<212> TYPE: PRT
<213> ORGANISM: chicken

<400> SEQUENCE: 120

Arg Ala Thr Ile Leu Arg Asp Asn Gly Gln Ser Thr Val Arg Leu Gln
1               5                   10                  15

Leu Ser Asn Leu Arg Ala Glu Asp Thr Gly Thr Tyr Tyr Cys Ala Lys
            20                  25                  30

<210> SEQ ID NO 121
<211> LENGTH: 10
<212> TYPE: PRT
<213> ORGANISM: chicken

<400> SEQUENCE: 121

Trp Gly His Gly Thr Glu Val Ile Val Ser
1               5                   10

<210> SEQ ID NO 122
<211> LENGTH: 20
<212> TYPE: PRT
<213> ORGANISM: chicken

<400> SEQUENCE: 122

Ala Val Thr Gln Pro Ala Ser Val Ser Ala Asn Leu Gly Gly Thr Val
1               5                   10                  15

Glu Ile Thr Cys
            20

<210> SEQ ID NO 123
<211> LENGTH: 16
<212> TYPE: PRT
<213> ORGANISM: chicken

<400> SEQUENCE: 123

Trp Tyr Gln Gln Lys Ser Pro Gly Ser Ala Pro Val Thr Val Ile Tyr
1               5                   10                  15

<210> SEQ ID NO 124
<211> LENGTH: 32
<212> TYPE: PRT
<213> ORGANISM: chicken

<400> SEQUENCE: 124

Asp Ile Pro Ser Arg Phe Ser Gly Ser Lys Ser Gly Ser Thr Gly Thr
1               5                   10                  15
Leu Thr Ile Thr Gly Val Gln Ala Glu Asp Glu Ala Val Tyr Phe Cys
            20                  25                  30

<210> SEQ ID NO 125
<211> LENGTH: 10
<212> TYPE: PRT
<213> ORGANISM: chicken

<400> SEQUENCE: 125

Phe Gly Ala Gly Thr Thr Leu Thr Val Leu
1               5                   10

<210> SEQ ID NO 126
<211> LENGTH: 30
<212> TYPE: PRT
<213> ORGANISM: chicken

<400> SEQUENCE: 126

Ala Val Thr Leu Asp Glu Ser Gly Gly Gly Leu Gln Thr Pro Gly Gly
1               5                   10                  15
Ala Leu Ser Leu Val Cys Lys Ala Ser Gly Phe Thr Phe Ser
            20                  25                  30

<210> SEQ ID NO 127
<211> LENGTH: 14
<212> TYPE: PRT
<213> ORGANISM: chicken

<400> SEQUENCE: 127

Trp Met Arg Gln Ala Pro Gly Lys Gly Leu Glu Tyr Val Ala
1               5                   10

<210> SEQ ID NO 128
<211> LENGTH: 32
<212> TYPE: PRT
<213> ORGANISM: chicken

<400> SEQUENCE: 128

Arg Ala Thr Ile Leu Arg Asp Asn Gly Gln Ser Thr Val Arg Leu Gln
1               5                   10                  15
Leu Ser Asn Leu Arg Ala Glu Asp Thr Gly Thr Tyr Tyr Cys Ala Lys
            20                  25                  30

<210> SEQ ID NO 129
<211> LENGTH: 10
<212> TYPE: PRT
<213> ORGANISM: chicken

<400> SEQUENCE: 129

Trp Gly His Gly Thr Glu Val Ile Val Ser
1               5                   10

<210> SEQ ID NO 130
<211> LENGTH: 20

```
<212> TYPE: PRT
<213> ORGANISM: chicken

<400> SEQUENCE: 130

Ala Ser Thr Gln Pro Ser Ser Val Ser Ala Asn Pro Gly Gly Thr Val
1               5                   10                  15

Glu Ile Thr Cys
            20

<210> SEQ ID NO 131
<211> LENGTH: 16
<212> TYPE: PRT
<213> ORGANISM: chicken

<400> SEQUENCE: 131

Trp Tyr Gln Gln Lys Ser Pro Gly Ser Ala Pro Val Thr Val Ile Tyr
1               5                   10                  15

<210> SEQ ID NO 132
<211> LENGTH: 32
<212> TYPE: PRT
<213> ORGANISM: chicken

<400> SEQUENCE: 132

Asn Ile Pro Ser Arg Phe Ser Gly Ser Lys Ser Gly Ser Thr Ala Thr
1               5                   10                  15

Leu Thr Ile Thr Gly Val Gln Ala Glu Asp Glu Ala Val Tyr Phe Cys
            20                  25                  30

<210> SEQ ID NO 133
<211> LENGTH: 10
<212> TYPE: PRT
<213> ORGANISM: chicken

<400> SEQUENCE: 133

Phe Gly Ala Gly Thr Thr Leu Thr Val Leu
1               5                   10

<210> SEQ ID NO 134
<211> LENGTH: 15
<212> TYPE: PRT
<213> ORGANISM: Artificial Sequence
<220> FEATURE:
<223> OTHER INFORMATION: linker

<400> SEQUENCE: 134

Gly Gly Gly Gly Ser Gly Gly Gly Gly Ser Gly Gly Gly Gly Ser
1               5                   10                  15

<210> SEQ ID NO 135
<211> LENGTH: 379
<212> TYPE: DNA
<213> ORGANISM: Artificial Sequence
<220> FEATURE:
<223> OTHER INFORMATION: Variable region

<400> SEQUENCE: 135
ggcgcgccga ggtgcagctg ttggagtctg ggggaggctt ggtacagcct ggggggtccc      60
tgagactctc ctgtgcagcc tctggattca ccttcagcac ttatgccatg ggttgggtcc    120
gccaggcgcc cggcaagggg ctggagttcg tcgccgctat taggaatgat ggtagttgga    180
caggctacgg ggcggcggtg aagggccgtt tcaccatctc cagagacaat tccaagaaca    240
cgctctatct gcaaatgaac agcctgagag cagaggacac ggctgtgtat tactgcgcca    300
```

```
aatatactgg tagtagtggt ggtagcatcg gcgcatgggg ccagggaacc ctggtcaccg    360
tctcctcagg tgaggatcc                                                 379

<210> SEQ ID NO 136
<211> LENGTH: 379
<212> TYPE: DNA
<213> ORGANISM: Artificial Sequence
<220> FEATURE:
<223> OTHER INFORMATION: Variable region

<400> SEQUENCE: 136
ggcgcgccga ggtgcagctg ttggagtctg ggggaggctt ggtacagcct ggggggtccc     60
tgagactctc ctgtgcagcc tctggattca ccttcagcac ttatgccatg ggttgggtcc    120
gccaggcgcc cggcaagggg ctggagttcg tcagcgctat taggaatgat ggtagttgga    180
caggctacgg ggcggcggtg aagggccgtt tcaccatctc cagagacaat tccaagaaca    240
cggtatatct gcaaatgaac agcctgagag cagaggacac ggctgtgtat tactgcgcca    300
aatatactgg tagtagtggt ggtagcatcg gcgcatgggg ccagggaacc ctggtcaccg    360
tctcctcagg tgaggatcc                                                 379

<210> SEQ ID NO 137
<211> LENGTH: 379
<212> TYPE: DNA
<213> ORGANISM: Artificial Sequence
<220> FEATURE:
<223> OTHER INFORMATION: Variable region

<400> SEQUENCE: 137
ggcgcgccga ggtgcagctg ttggagtctg ggggaggctt ggtacagcct ggggggtccc     60
tgagactctc ctgtgcagcc tctggattca ccttcagcac ttatgccatg ggttgggtcc    120
gccaggcgcc cggcaagggg ctggagttcg tcgctgctat taggaatgat ggtagttgga    180
caggctacgg ggcggcggtg aagggccgtg tcaccatctc cagagacaat tccaagaaca    240
cggtatatct gcaaatgaac agcctgagag cagaggacac ggctgtgtat tactgcgcca    300
aatatactgg tagtagtggt ggtagcatcg gcgcatgggg ccagggaacc ctggtcaccg    360
tctcctcagg tgaggatcc                                                 379

<210> SEQ ID NO 138
<211> LENGTH: 336
<212> TYPE: DNA
<213> ORGANISM: Artificial Sequence
<220> FEATURE:
<223> OTHER INFORMATION: Variable region

<400> SEQUENCE: 138
ggcgcgccag ctatgagctg actcagccac cctcggtgtc agtgtcccca ggacagacgg     60
ccaggatcac ctgctccggg gggaatagga actactacta tggctggtac cagcagaagc    120
caggccaggc ccctgtgctg gtgatatatg ctaacgacaa gagaccctcg ggaatccctg    180
agcgattctc tggctcctca tcagggacaa cagtgacgtt gaccatcagt ggagtccagg    240
cagaagatga ggctgactat tactgtggga ccgcagacac cggaagtat gtattcggcg    300 gagggaccaa gctgaccgtc ctgggtgagt ggatcc                              336

<210> SEQ ID NO 139
<211> LENGTH: 336
<212> TYPE: DNA
```

<213> ORGANISM: Artificial Sequence
<220> FEATURE:
<223> OTHER INFORMATION: Variable region

<400> SEQUENCE: 139

```
ggcgcgccag ctatgagctg actcagccac cctcggtgtc agtgtcccca ggacagacgg      60
ccaggatcac ctgctccggg gggaatagga actactacta tggctggtac cagcagaagc    120
caggccaggc ccctgtgacc gtgatatatg ctaacgacaa gagaccctcg ggaatccctg    180
agcgattctc tggctcctac tcagggaaca caaccacgtt gaccatcagt ggagtccagg    240
cagaagatga ggctgactat tactgtggga ccgcagacac cgggaagtat gtattcggcg    300
gagggaccaa gctgaccgtc ctgggtgagt ggatcc                              336
```

<210> SEQ ID NO 140
<211> LENGTH: 336
<212> TYPE: DNA
<213> ORGANISM: Artificial Sequence
<220> FEATURE:
<223> OTHER INFORMATION: Variable region

<400> SEQUENCE: 140

```
ggcgcgccag ctatgagctg actcagccac cctcggtgtc agtgtcccca ggacagacgg      60
ccaggatcac ctgctccggg gggaatagga actactacta tggctggtac cagcagaagc    120
caggccaggc ccctgtgacc gtgatatatg ctaacgacaa gagaccctcg ggaatccctg    180
agcgattctc tggctccacc tcagggaaca caaccacgtt gaccatcagt ggagtccagg    240
cagaagatga ggctgactat tactgtggga ccgcagacac cgggaagtat gtattcggcg    300
gagggaccaa gctgaccgtc ctgggtgagt ggatcc                              336
```

<210> SEQ ID NO 141
<211> LENGTH: 336
<212> TYPE: DNA
<213> ORGANISM: Artificial Sequence
<220> FEATURE:
<223> OTHER INFORMATION: Variable region

<400> SEQUENCE: 141

```
ggcgcgccag ctatgagctg actcagccac cctcggtgtc agtgtcccca ggacagacgg      60
ccaggatcac ctgctccggg gggaatagga actactacta tggctggtac cagcagaagc    120
caggccaggc ccctgtgacc gtgatatatg ctaacgacaa gagaccctcg ggaatccctg    180
agcgattctc tggctccaac tcagggtcaa caaccacgtt gaccatcagt ggagtccagg    240
cagaagatga ggctgactat tactgtggga ccgcagacac cgggaagtat gtattcggcg    300
gagggaccaa gctgaccgtc ctgggtgagt ggatcc                              336
```

<210> SEQ ID NO 142
<211> LENGTH: 336
<212> TYPE: DNA
<213> ORGANISM: Artificial Sequence
<220> FEATURE:
<223> OTHER INFORMATION: Variable region

<400> SEQUENCE: 142

```
ggcgcgccag ctatgagctg actcagccac cctcggtgtc agtgtcccca ggacagacgg      60
ccaggatcac ctgctccggg ggtagtggca ggtactatta tggctggtac cagcagaagc    120
caggccaggc ccctgtgctg gtgatatata gcagcaccca cagaccctca ggaatccctg    180
agcgattctc tggctcctca tcaggdacaa cagtgacgtt gaccatcagt ggagtccagg    240
```

| | |
|---|---|
| cagaagatga ggctgactat tactgtggga ctgcagacag cagcagctat gtcttcggcg | 300 |
| gagggaccaa gctgaccgtc ctgggtgagt ggatcc | 336 |

<210> SEQ ID NO 143
<211> LENGTH: 336
<212> TYPE: DNA
<213> ORGANISM: Artificial Sequence
<220> FEATURE:
<223> OTHER INFORMATION: Variable region

<400> SEQUENCE: 143

| | |
|---|---|
| ggcgcgccag ctatgagctg actcagccac cctcggtgtc agtgtcccca ggacagacgg | 60 |
| ccaggatcac ctgctccggg ggtagtggca ggtactatta tggctggtac cagcagaagc | 120 |
| caggccaggc ccctgtgacc gtgatatata gcagcaccca cagaccctca ggaatccctg | 180 |
| agcgattctc tggctcctat tcagggaata caaccacgtt gaccatcagt ggagtccagg | 240 |
| cagaagatga ggctgactat tactgtggga ctgcagacag cagcagctat gtcttcggcg | 300 |
| gagggaccaa gctgaccgtc ctgggtgagt ggatcc | 336 |

<210> SEQ ID NO 144
<211> LENGTH: 336
<212> TYPE: DNA
<213> ORGANISM: Artificial Sequence
<220> FEATURE:
<223> OTHER INFORMATION: Variable region

<400> SEQUENCE: 144

| | |
|---|---|
| ggcgcgccag ctatgagctg actcagccac cctcggtgtc agtgtcccca ggacagacgg | 60 |
| ccaggatcac ctgctccggg ggtagtggca ggtactatta tggctggtac cagcagaagc | 120 |
| caggccaggc ccctgtgacc gtgatatata gcagcaccca cagaccctca ggaatccctg | 180 |
| agcgattctc tggctccaat tcagggaata caaccacgtt gaccatcagt ggagtccagg | 240 |
| cagaagatga ggctgactat tactgtggga ctgcagacag cagcagctat gtcttcggcg | 300 |
| gagggaccaa gctgaccgtc ctgggtgagt ggatcc | 336 |

<210> SEQ ID NO 145
<211> LENGTH: 336
<212> TYPE: DNA
<213> ORGANISM: Artificial Sequence
<220> FEATURE:
<223> OTHER INFORMATION: Variable region

<400> SEQUENCE: 145

| | |
|---|---|
| ggcgcgccag ctatgagctg actcagccac cctcggtgtc agtgtcccca ggacagacgg | 60 |
| ccaggatcac ctgctccggg ggtagtggca ggtactatta tggctggtac cagcagaagc | 120 |
| caggccaggc ccctgtgacc gtgatatata gcagcaccca cagaccctca ggaatccctg | 180 |
| agcgattctc tggctccacc tcagggaata caaccacgtt gaccatcagt ggagtccagg | 240 |
| cagaagatga ggctgactat tactgtggga ctgcagacag cagcagctat gtcttcggcg | 300 |
| gagggaccaa gctgaccgtc ctgggtgagt ggatcc | 336 |

<210> SEQ ID NO 146
<211> LENGTH: 336
<212> TYPE: DNA
<213> ORGANISM: Artificial Sequence
<220> FEATURE:
<223> OTHER INFORMATION: Variable region

<400> SEQUENCE: 146

```
ggcgcgccag ctatgagctg actcagccac cctcggtgtc agtgtcccca ggacagacgg      60
ccaggatcac ctgctccggg ggtagtggca ggtactatta tggctggtac cagcagaagc     120
caggccaggc ccctgtgacc gtgatatata gcagcaccca cagaccctca ggaatccctg     180
agcgattctc tggctccaat tcagggagca caaccacgtt gaccatcagt ggagtccagg     240
cagaagatga ggctgactat tactgtggga ctgcagacag cagcagctat gtcttcggcg     300
gagggaccaa gctgaccgtc ctgggtgagt ggatcc                                336
```

<210> SEQ ID NO 147
<211> LENGTH: 31
<212> TYPE: DNA
<213> ORGANISM: Artificial Sequence
<220> FEATURE:
<223> OTHER INFORMATION: Primer

<400> SEQUENCE: 147

```
atataggcgc gccgaggtgc agctgttgga g                                     31
```

<210> SEQ ID NO 148
<211> LENGTH: 30
<212> TYPE: DNA
<213> ORGANISM: Artificial Sequence
<220> FEATURE:
<223> OTHER INFORMATION: Primer

<400> SEQUENCE: 148

```
tatatggatc ctcacctgag gagacggtga                                       30
```

<210> SEQ ID NO 149
<211> LENGTH: 34
<212> TYPE: DNA
<213> ORGANISM: Artificial Sequence
<220> FEATURE:
<223> OTHER INFORMATION: Primer

<400> SEQUENCE: 149

```
atataggcgc gccagctatg agctgactca gcca                                  34
```

<210> SEQ ID NO 150
<211> LENGTH: 30
<212> TYPE: DNA
<213> ORGANISM: Artificial Sequence
<220> FEATURE:
<223> OTHER INFORMATION: Primer

<400> SEQUENCE: 150

```
tatatggatc cactcaccca ggacggtcag                                       30
```

<210> SEQ ID NO 151
<211> LENGTH: 379
<212> TYPE: DNA
<213> ORGANISM: Artificial Sequence
<220> FEATURE:
<223> OTHER INFORMATION: Variable region

<400> SEQUENCE: 151

```
ggcgcgccga ggtgcagctg ttggagtctg ggggaggctt ggtacagcct ggggggtccc      60
tgagactctc ctgtgcagcc tctggattca ccttcagcag ttatggcatg ggatgggtcc     120
gccaggcgcc cggcaagggg ctggagttcg tcgccgctat taggaatgat ggcagttgga     180
caggctacgg ggcggcggtg aagggccgtt tcaccatctc cagagacaat tccaagaaca     240
```

```
cgctctatct gcaaatgaac agcctgagag cagaggacac ggctgtgtat tactgcgcca      300
aaactactgg tagtcgtggt ggtagcatcg acgcatgggg ccagggaacc ctggtcaccg      360
tctcctcagg tgaggatcc                                                   379
```

<210> SEQ ID NO 152
<211> LENGTH: 333
<212> TYPE: DNA
<213> ORGANISM: Artificial Sequence
<220> FEATURE:
<223> OTHER INFORMATION: Variable region

<400> SEQUENCE: 152

```
ggcgcgccag ctatgagctg actcagccac cctcggtgtc agtgtcccca ggacagacgg       60
ccaggatcac ctgctccggg ggtggcaggt actattatgg ctggtaccag cagaagccag      120
gccaggcccc tgtgaccgtg atatatgcta acgacaagag accctcggga atccctgagc      180
gattctctgg ctccaactca gggtcaacaa ccacgttgac catcagtgga gtccaggcag      240
aagatgaggc tgactattac tgtgggagtg cagagaccag cagctatgta ttcggcggag      300
ggaccaagct gaccgtcctg ggtgagtgga tcc                                  333
```

<210> SEQ ID NO 153
<211> LENGTH: 330
<212> TYPE: PRT
<213> ORGANISM: Artificial Sequence
<220> FEATURE:
<223> OTHER INFORMATION: Heavy chain constant region

<400> SEQUENCE: 153

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
                210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 154
<211> LENGTH: 107
<212> TYPE: PRT
<213> ORGANISM: Artificial Sequence
<220> FEATURE:
<223> OTHER INFORMATION: Light chain constant region

<400> SEQUENCE: 154

Gly Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 155
<211> LENGTH: 120
<212> TYPE: PRT
<213> ORGANISM: Artificial Sequence
<220> FEATURE:
<223> OTHER INFORMATION: Variable region

<400> SEQUENCE: 155

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Phe Val
        35                  40                  45

Ala Ala Ile Arg Asn Asp Gly Ser Trp Thr Gly Tyr Gly Ala Ala Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Tyr Thr Gly Ser Ser Gly Gly Ser Ile Gly Ala Trp Gly Gln
            100                 105                 110

Gly Thr Leu Val Thr Val Ser Ser
        115                 120

<210> SEQ ID NO 156
<211> LENGTH: 120
<212> TYPE: PRT
<213> ORGANISM: Artificial Sequence
<220> FEATURE:
<223> OTHER INFORMATION: Variable region

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Phe Val
        35                  40                  45

Ser Ala Ile Arg Asn Asp Gly Ser Trp Thr Gly Tyr Gly Ala Ala Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Ser Ser Gly Gly Ser Ile Gly Ala Trp Gly Gln
            100                 105                 110

Gly Thr Leu Val Thr Val Ser Ser
        115                 120

<210> SEQ ID NO 157
<211> LENGTH: 120
<212> TYPE: PRT
<213> ORGANISM: Artificial Sequence
<220> FEATURE:
<223> OTHER INFORMATION: Variable region

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Phe Val
        35                  40                  45

Ala Ala Ile Arg Asn Asp Gly Ser Trp Thr Gly Tyr Gly Ala Ala Val
    50                  55                  60

Lys Gly Arg Val Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Ser Ser Gly Gly Ser Ile Gly Ala Trp Gly Gln
            100                 105                 110

Gly Thr Leu Val Thr Val Ser Ser
        115                 120

<210> SEQ ID NO 158
```

```
<211> LENGTH: 105
<212> TYPE: PRT
<213> ORGANISM: Artificial Sequence
<220> FEATURE:
<223> OTHER INFORMATION: Variable region

<400> SEQUENCE: 158

Ser Tyr Glu Leu Thr Gln Pro Pro Ser Val Ser Val Ser Pro Gly Gln
1               5                   10                  15

Thr Ala Arg Ile Thr Cys Ser Gly Gly Asn Arg Asn Tyr Tyr Tyr Gly
            20                  25                  30

Trp Tyr Gln Gln Lys Pro Gly Gln Ala Pro Val Leu Val Ile Tyr Ala
        35                  40                  45

Asn Asp Lys Arg Pro Ser Gly Ile Pro Glu Arg Phe Ser Gly Ser Ser
    50                  55                  60

Ser Gly Thr Thr Val Thr Leu Thr Ile Ser Gly Val Gln Ala Glu Asp
65                  70                  75                  80

Glu Ala Asp Tyr Tyr Cys Gly Thr Ala Asp Thr Gly Lys Tyr Val Phe
                85                  90                  95

Gly Gly Gly Thr Lys Leu Thr Val Leu
            100                 105

<210> SEQ ID NO 159
<211> LENGTH: 105
<212> TYPE: PRT
<213> ORGANISM: Artificial Sequence
<220> FEATURE:
<223> OTHER INFORMATION: Variable region

<400> SEQUENCE: 159

Ser Tyr Glu Leu Thr Gln Pro Pro Ser Val Ser Val Ser Pro Gly Gln
1               5                   10                  15

Thr Ala Arg Ile Thr Cys Ser Gly Gly Asn Arg Asn Tyr Tyr Tyr Gly
            20                  25                  30

Trp Tyr Gln Gln Lys Pro Gly Gln Ala Pro Val Thr Val Ile Tyr Ala
        35                  40                  45

Asn Asp Lys Arg Pro Ser Gly Ile Pro Glu Arg Phe Ser Gly Ser Tyr
    50                  55                  60

Ser Gly Asn Thr Thr Leu Thr Ile Ser Gly Val Gln Ala Glu Asp
65                  70                  75                  80

Glu Ala Asp Tyr Tyr Cys Gly Thr Ala Asp Thr Gly Lys Tyr Val Phe
                85                  90                  95

Gly Gly Gly Thr Lys Leu Thr Val Leu
            100                 105

<210> SEQ ID NO 160
<211> LENGTH: 105
<212> TYPE: PRT
<213> ORGANISM: Artificial Sequence
<220> FEATURE:
<223> OTHER INFORMATION: Variable region

<400> SEQUENCE: 160

Ser Tyr Glu Leu Thr Gln Pro Pro Ser Val Ser Val Ser Pro Gly Gln
1               5                   10                  15

Thr Ala Arg Ile Thr Cys Ser Gly Gly Asn Arg Asn Tyr Tyr Tyr Gly
            20                  25                  30

Trp Tyr Gln Gln Lys Pro Gly Gln Ala Pro Val Thr Val Ile Tyr Ala
        35                  40                  45
```

```
Asn Asp Lys Arg Pro Ser Gly Ile Pro Glu Arg Phe Ser Gly Ser Thr
 50                  55                  60
Ser Gly Asn Thr Thr Thr Leu Thr Ile Ser Gly Val Gln Ala Glu Asp
 65                  70                  75                  80
Glu Ala Asp Tyr Tyr Cys Gly Thr Ala Asp Thr Gly Lys Tyr Val Phe
                 85                  90                  95
Gly Gly Gly Thr Lys Leu Thr Val Leu
            100                 105
```

<210> SEQ ID NO 161
<211> LENGTH: 105
<212> TYPE: PRT
<213> ORGANISM: Artificial Sequence
<220> FEATURE:
<223> OTHER INFORMATION: Variable region

<400> SEQUENCE: 161

```
Ser Tyr Glu Leu Thr Gln Pro Pro Ser Val Ser Val Ser Pro Gly Gln
 1               5                  10                  15
Thr Ala Arg Ile Thr Cys Ser Gly Gly Asn Arg Asn Tyr Tyr Tyr Gly
                 20                  25                  30
Trp Tyr Gln Gln Lys Pro Gly Gln Ala Pro Val Thr Val Ile Tyr Ala
             35                  40                  45
Asn Asp Lys Arg Pro Ser Gly Ile Pro Glu Arg Phe Ser Gly Ser Asn
 50                  55                  60
Ser Gly Ser Thr Thr Thr Leu Thr Ile Ser Gly Val Gln Ala Glu Asp
 65                  70                  75                  80
Glu Ala Asp Tyr Tyr Cys Gly Thr Ala Asp Thr Gly Lys Tyr Val Phe
                 85                  90                  95
Gly Gly Gly Thr Lys Leu Thr Val Leu
            100                 105
```

<210> SEQ ID NO 162
<211> LENGTH: 120
<212> TYPE: PRT
<213> ORGANISM: Artificial Sequence
<220> FEATURE:
<223> OTHER INFORMATION: Variable region

<400> SEQUENCE: 162

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Thr Tyr
                 20                  25                  30
Ala Met Gly Trp Val Arg Gln Ala Pro Gly Lys Gly Leu Glu Phe Val
             35                  40                  45
Ala Ala Ile Arg Asn Asp Gly Ser Trp Thr Gly Tyr Gly Ala Ala Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Tyr Thr Gly Ser Ser Gly Ser Ile Gly Ala Trp Gly Gln
            100                 105                 110
Gly Thr Leu Val Thr Val Ser Ser
            115                 120
```

<210> SEQ ID NO 163

```
<211> LENGTH: 120
<212> TYPE: PRT
<213> ORGANISM: Artificial Sequence
<220> FEATURE:
<223> OTHER INFORMATION: Variable region

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Phe Val
        35                  40                  45

Ser Ala Ile Arg Asn Asp Gly Ser Trp Thr Gly Tyr Gly Ala Ala Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Ser Ser Gly Gly Ser Ile Gly Ala Trp Gly Gln
            100                 105                 110

Gly Thr Leu Val Thr Val Ser Ser
            115                 120

<210> SEQ ID NO 164
<211> LENGTH: 120
<212> TYPE: PRT
<213> ORGANISM: Artificial Sequence
<220> FEATURE:
<223> OTHER INFORMATION: Variable region

<400> SEQUENCE: 164

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Phe Val
        35                  40                  45

Ala Ala Ile Arg Asn Asp Gly Ser Trp Thr Gly Tyr Gly Ala Ala Val
    50                  55                  60

Lys Gly Arg Val Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Ser Ser Gly Gly Ser Ile Gly Ala Trp Gly Gln
            100                 105                 110

Gly Thr Leu Val Thr Val Ser Ser
            115                 120

<210> SEQ ID NO 165
<211> LENGTH: 105
<212> TYPE: PRT
<213> ORGANISM: Artificial Sequence
<220> FEATURE:
<223> OTHER INFORMATION: Variable region

<400> SEQUENCE: 165

Ser Tyr Glu Leu Thr Gln Pro Pro Ser Val Ser Val Pro Gly Gln
1               5                   10                  15
```

```
Thr Ala Arg Ile Thr Cys Ser Gly Gly Ser Gly Arg Tyr Tyr Tyr Gly
            20                  25                  30

Trp Tyr Gln Gln Lys Pro Gly Gln Ala Pro Val Leu Val Ile Tyr Ser
        35                  40                  45

Ser Thr His Arg Pro Ser Gly Ile Pro Glu Arg Phe Ser Gly Ser Ser
    50                  55                  60

Ser Gly Thr Thr Val Thr Leu Thr Ile Ser Gly Val Gln Ala Glu Asp
65                  70                  75                  80

Glu Ala Asp Tyr Tyr Cys Gly Thr Ala Asp Ser Ser Ser Tyr Val Phe
                85                  90                  95

Gly Gly Gly Thr Lys Leu Thr Val Leu
            100                 105
```

<210> SEQ ID NO 166
<211> LENGTH: 105
<212> TYPE: PRT
<213> ORGANISM: Artificial Sequence
<220> FEATURE:
<223> OTHER INFORMATION: Variable region

<400> SEQUENCE: 166

```
Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Arg Tyr Tyr Tyr Gly
            20                  25                  30

Trp Tyr Gln Gln Lys Pro Gly Gln Ala Pro Val Thr Val Ile Tyr Ser
        35                  40                  45

Ser Thr His Arg Pro Ser Gly Ile Pro Glu Arg Phe Ser Gly Ser Tyr
    50                  55                  60

Ser Gly Asn Thr Thr Thr Leu Thr Ile Ser Gly Val Gln Ala Glu Asp
65                  70                  75                  80

Glu Ala Asp Tyr Tyr Cys Gly Thr Ala Asp Ser Ser Ser Tyr Val Phe
                85                  90                  95

Gly Gly Gly Thr Lys Leu Thr Val Leu
            100                 105
```

<210> SEQ ID NO 167
<211> LENGTH: 105
<212> TYPE: PRT
<213> ORGANISM: Artificial Sequence
<220> FEATURE:
<223> OTHER INFORMATION: Variable region

<400> SEQUENCE: 167

```
Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Arg Tyr Tyr Tyr Gly
            20                  25                  30

Trp Tyr Gln Gln Lys Pro Gly Gln Ala Pro Val Thr Val Ile Tyr Ser
        35                  40                  45

Ser Thr His Arg Pro Ser Gly Ile Pro Glu Arg Phe Ser Gly Ser Asn
    50                  55                  60

Ser Gly Asn Thr Thr Thr Leu Thr Ile Ser Gly Val Gln Ala Glu Asp
65                  70                  75                  80

Glu Ala Asp Tyr Tyr Cys Gly Thr Ala Asp Ser Ser Ser Tyr Val Phe
                85                  90                  95

Gly Gly Gly Thr Lys Leu Thr Val Leu
            100                 105
```

<210> SEQ ID NO 168
<211> LENGTH: 105
<212> TYPE: PRT
<213> ORGANISM: Artificial Sequence
<220> FEATURE:
<223> OTHER INFORMATION: Variable region

<400> SEQUENCE: 168

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Arg Tyr Tyr Tyr Gly
            20                  25                  30

Trp Tyr Gln Gln Lys Pro Gly Gln Ala Pro Val Thr Val Ile Tyr Ser
        35                  40                  45

Ser Thr His Arg Pro Ser Gly Ile Pro Glu Arg Phe Ser Gly Ser Thr
    50                  55                  60

Ser Gly Asn Thr Thr Thr Leu Thr Ile Ser Gly Val Gln Ala Glu Asp
65                  70                  75                  80

Glu Ala Asp Tyr Tyr Cys Gly Thr Ala Asp Ser Ser Ser Tyr Val Phe
                85                  90                  95

Gly Gly Gly Thr Lys Leu Thr Val Leu
            100                 105

<210> SEQ ID NO 169
<211> LENGTH: 105
<212> TYPE: PRT
<213> ORGANISM: Artificial Sequence
<220> FEATURE:
<223> OTHER INFORMATION: Variable region

<400> SEQUENCE: 169

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Arg Tyr Tyr Tyr Gly
            20                  25                  30

Trp Tyr Gln Gln Lys Pro Gly Gln Ala Pro Val Thr Val Ile Tyr Ser
        35                  40                  45

Ser Thr His Arg Pro Ser Gly Ile Pro Glu Arg Phe Ser Gly Ser Asn
    50                  55                  60

Ser Gly Ser Thr Thr Thr Leu Thr Ile Ser Gly Val Gln Ala Glu Asp
65                  70                  75                  80

Glu Ala Asp Tyr Tyr Cys Gly Thr Ala Asp Ser Ser Ser Tyr Val Phe
                85                  90                  95

Gly Gly Gly Thr Lys Leu Thr Val Leu
            100                 105

<210> SEQ ID NO 170
<211> LENGTH: 450
<212> TYPE: PRT
<213> ORGANISM: Artificial Sequence
<220> FEATURE:
<223> OTHER INFORMATION: Heavy chain

<400> SEQUENCE: 170

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

-continued

Gly Met Gly Trp Val Arg Gln Ala Pro Gly Lys Gly Leu Glu Phe Val
    35                  40                  45

Ala Ala Ile Arg Asn Asp Gly Ser Trp Thr Gly Tyr Gly Ala Ala Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Thr Gly Ser Arg Gly Gly Ser Ile Asp Ala Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys

```
                    450

<210> SEQ ID NO 171
<211> LENGTH: 211
<212> TYPE: PRT
<213> ORGANISM: Artificial Sequence
<220> FEATURE:
<223> OTHER INFORMATION: Light chain

<400> SEQUENCE: 171

Ser Tyr Glu Leu Thr Gln Pro Pro Ser Val Ser Val Ser Pro Gly Gln
1               5                   10                  15

Thr Ala Arg Ile Thr Cys Ser Gly Gly Arg Tyr Tyr Tyr Gly Trp
            20                  25                  30

Tyr Gln Gln Lys Pro Gly Gln Ala Pro Val Thr Val Ile Tyr Ala Asn
        35                  40                  45

Asp Lys Arg Pro Ser Gly Ile Pro Glu Arg Phe Ser Gly Ser Asn Ser
    50                  55                  60

Gly Ser Thr Thr Thr Leu Thr Ile Ser Gly Val Gln Ala Glu Asp Glu
65                  70                  75                  80

Ala Asp Tyr Tyr Cys Gly Ser Ala Glu Thr Ser Ser Tyr Val Phe Gly
                85                  90                  95

Gly Gly Thr Lys Leu Thr Val Leu Gly Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 172
<211> LENGTH: 450
<212> TYPE: PRT
<213> ORGANISM: Artificial Sequence
<220> FEATURE:
<223> OTHER INFORMATION: Heavy chain

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Phe Val
        35                  40                  45

Ala Ala Ile Arg Asn Asp Gly Ser Trp Thr Gly Tyr Gly Ala Ala Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95
Ala Lys Tyr Thr Gly Ser Ser Gly Gly Ser Ile Gly Ala Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
    450

<210> SEQ ID NO 173
<211> LENGTH: 212
<212> TYPE: PRT
<213> ORGANISM: Artificial Sequence
<220> FEATURE:
<223> OTHER INFORMATION: Light chain
```

<400> SEQUENCE: 173

Ser Tyr Glu Leu Thr Gln Pro Pro Ser Val Ser Val Ser Pro Gly Gln
1               5                   10                  15

Thr Ala Arg Ile Thr Cys Ser Gly Gly Asn Arg Asn Tyr Tyr Tyr Gly
                20                  25                  30

Trp Tyr Gln Gln Lys Pro Gly Gln Ala Pro Val Thr Val Ile Tyr Ala
            35                  40                  45

Asn Asp Lys Arg Pro Ser Gly Ile Pro Glu Arg Phe Ser Gly Ser Asn
        50                  55                  60

Ser Gly Ser Thr Thr Thr Leu Thr Ile Ser Gly Val Gln Ala Glu Asp
65                  70                  75                  80

Glu Ala Asp Tyr Tyr Cys Gly Thr Ala Asp Thr Gly Lys Tyr Val Phe
                85                  90                  95

Gly Gly Gly Thr Lys Leu Thr Val Leu Gly Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
        210

<210> SEQ ID NO 174
<211> LENGTH: 450
<212> TYPE: PRT
<213> ORGANISM: Artificial Sequence
<220> FEATURE:
<223> OTHER INFORMATION: Heavy chain

<400> SEQUENCE: 174

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Gly Trp Val Arg Gln Ala Pro Gly Lys Gly Leu Glu Phe Val
            35                  40                  45

Ala Ala Ile Arg Asn Asp Gly Ser Trp Thr Gly Tyr Gly Ala Ala Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Ser Ser Gly Ser Ile Gly Ala Trp Gly Gln
            100                 105                 110

Gly Thr Leu Val Thr Val Ser Ser Ala Ser Thr Lys Gly Pro Ser Val
        115                 120                 125

```
Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 175
<211> LENGTH: 211
<212> TYPE: PRT
<213> ORGANISM: Artificial Sequence
<220> FEATURE:
<223> OTHER INFORMATION: Light chain

<400> SEQUENCE: 175

Ser Tyr Glu Leu Thr Gln Pro Pro Ser Val Ser Val Ser Pro Gly Gln
1               5                   10                  15

Thr Ala Arg Ile Thr Cys Ser Gly Gly Arg Tyr Tyr Gly Trp
            20                  25                  30
```

```
Tyr Gln Gln Lys Pro Gly Gln Ala Pro Val Thr Val Ile Tyr Ala Asn
            35                  40                  45

Asp Lys Arg Pro Ser Gly Ile Pro Glu Arg Phe Ser Gly Ser Asn Ser
 50                  55                  60

Gly Ser Thr Thr Thr Leu Thr Ile Ser Gly Val Gln Ala Glu Asp Glu
 65                  70                  75                  80

Ala Asp Tyr Tyr Cys Gly Ser Ala Glu Thr Ser Ser Tyr Val Phe Gly
                 85                  90                  95

Gly Gly Thr Lys Leu Thr Val Leu Gly Thr Val Ala Ala Pro Ser Val
            100                 105                 110

Phe Ile Phe Pro Pro Ser Asp Glu Gln Leu Lys Ser Gly Thr Ala Ser
            115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
            195                 200                 205

Gly Glu Cys
        210

<210> SEQ ID NO 176
<211> LENGTH: 450
<212> TYPE: PRT
<213> ORGANISM: Artificial Sequence
<220> FEATURE:
<223> OTHER INFORMATION: Heavy chain

<400> SEQUENCE: 176

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
             20                  25                  30

Ala Met Gly Trp Val Arg Gln Ala Pro Gly Lys Gly Leu Glu Phe Val
            35                  40                  45

Ala Ala Ile Arg Asn Asp Gly Ser Trp Thr Gly Tyr Gly Ala Ala Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Thr Gly Ser Ser Gly Gly Ser Ile Gly Ala Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 177
<211> LENGTH: 212
<212> TYPE: PRT
<213> ORGANISM: Artificial Sequence
<220> FEATURE:
<223> OTHER INFORMATION: Light chain

<400> SEQUENCE: 177

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Arg Tyr Tyr Tyr Gly
            20                  25                  30

Trp Tyr Gln Gln Lys Pro Gly Gln Ala Pro Val Thr Val Ile Tyr Ser
            35                  40                  45

Ser Thr His Arg Pro Ser Gly Ile Pro Glu Arg Phe Ser Gly Ser Asn
        50                  55                  60

Ser Gly Ser Thr Thr Thr Leu Thr Ile Ser Gly Val Gln Ala Glu Asp
65                  70                  75                  80
```

```
Glu Ala Asp Tyr Tyr Cys Gly Thr Ala Asp Ser Ser Tyr Val Phe
             85                  90                  95

Gly Gly Gly Thr Lys Leu Thr Val Leu Gly Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210
```

<210> SEQ ID NO 178
<211> LENGTH: 360
<212> TYPE: DNA
<213> ORGANISM: Artificial Sequence
<220> FEATURE:
<223> OTHER INFORMATION: Variable region

<400> SEQUENCE: 178
gaggtgcagc tgttggagtc tgggggagga ctggtgcagc ctggcggaag cctgagactg    60
tcttgtgccg ccagcggctt caccttcagc acctatgcca tgggctgggt gcgccaggcc    120
cctggaaagg gcctggaatt tgtggccgcc atccggaacg atggcagctg acaggatat    180 ggcgccgctg tgaagggccg gttcaccatc agccgggaca cagcaagaa cacccctgtac    240 ctgcagatga acagcctgcg ggccgaggac accgccgtgt actactgtgc caagtacacc    300
ggcagcagcg gcggctctat tggagcttgg ggacagggaa ccctggtcac cgtctcctca    360

<210> SEQ ID NO 179
<211> LENGTH: 984
<212> TYPE: DNA
<213> ORGANISM: Artificial Sequence
<220> FEATURE:
<223> OTHER INFORMATION: Heavy chain constant region

<400> SEQUENCE: 179
gccagcacca agggccccag cgtgttccct ctggcccctt gtagcagaag caccagcgag    60
tctacagccg ccctgggctg cctcgtgaag gactactttc ccgagcccgt gaccgtgtcc    120
tggaactctg gcgctctgac aagcggcgtg cacacctttc agccgtgct gcagagcagc    180 ggcctgtact ctctgagcag cgtcgtgact gtgcccagca gctctctggg caccaagacc    240
tacacctgta acgtggacca caagcccagc aacaccaagg tggacaagcg ggtggaatct    300
aagtacggcc ctccctgccc tccttgccca gcccctgaat ttctgggcgg accctccgtg    360
ttcctgttcc ccccaaagcc caaggacacc ctgatgatca gccggacccc cgaagtgacc    420
tgcgtggtgg tggatgtgtc ccaggaagat cccgaggtgc agttcaattg gtacgtggac    480
ggcgtggaag tgcacaacgc caagaccaag cctagagagg aacagttcaa cagcacctac    540
cgggtggtgt ccgtgctgac agtgctgcat caggactggc tgaacggcaa agagtacaag    600

```
tgcaaggtgt ccaacaaggg cctgcccagc tccatcgaga aaaccatcag caaggccaag    660
ggccagcccc gcgaacccca ggtgtacaca ctgcctccaa gccaggaaga gatgaccaag    720
aaccaggtgt ccctgacctg tctcgtgaaa ggcttctacc cctccgatat cgccgtggaa    780
tgggagagca acggccagcc cgagaacaac tacaagacaa ccccccctgt gctggacagc    840
gacggctcat tcttcctgta cagcagactg accgtggaca agagccggtg gcaggaaggc    900
aacgtgttca gctgcagcgt gatgcacgag gccctgcaca accactacac ccagaagtcc    960
ctgtctctga gcctgggcaa gtga                                          984

<210> SEQ ID NO 180
<211> LENGTH: 315
<212> TYPE: DNA
<213> ORGANISM: Artificial Sequence
<220> FEATURE:
<223> OTHER INFORMATION: Variable region

<400> SEQUENCE: 180
agctatgagc tgactcagcc accctcggtg tcagtgtctc ctggccagac cgccagaatc     60
acatgtagcg gcggcagcgg ccggtactac tacggctggt atcagcagaa gcccggccag    120
gcccctgtga ccgtgatcta cagcagcacc cacagaccca cggcatccc cgagagattc     180 agcggcagca atagcggctc caccaccacc ctgacaatca gcggagtgca ggccgaggac    240
gaggccgatt actactgtgg caccgccgac agcagcagct acgtgttcgg cggaggaacc    300
aagctgaccg tcctg                                                    315

<210> SEQ ID NO 181
<211> LENGTH: 321
<212> TYPE: PRT
<213> ORGANISM: Artificial Sequence
<220> FEATURE:
<223> OTHER INFORMATION: Light chain constant region

<400> SEQUENCE: 181

Gly Gly Thr Cys Ala Gly Cys Cys Cys Ala Ala Gly Gly Cys Thr Gly
1               5                   10                  15

Cys Cys Cys Cys Cys Thr Cys Gly Gly Thr Cys Ala Cys Thr Cys Thr
            20                  25                  30

Gly Thr Thr Cys Cys Cys Gly Cys Cys Thr Cys Cys Thr Cys Thr
        35                  40                  45

Gly Ala Gly Gly Ala Gly Cys Thr Thr Cys Ala Ala Gly Cys Cys Ala
    50                  55                  60

Ala Cys Ala Ala Gly Gly Cys Cys Ala Cys Cys Thr Gly Gly Thr
65                  70                  75                  80

Gly Thr Gly Thr Cys Thr Cys Ala Thr Ala Gly Thr Gly Ala Cys
                85                  90                  95

Thr Thr Cys Thr Ala Cys Cys Gly Gly Ala Gly Cys Cys Gly
            100                 105                 110

Thr Gly Ala Cys Ala Gly Thr Gly Gly Cys Cys Thr Gly Ala Ala
        115                 120                 125

Gly Gly Cys Ala Gly Ala Thr Ala Gly Cys Ala Gly Cys Cys Cys
    130                 135                 140

Gly Thr Cys Ala Ala Gly Gly Cys Gly Gly Ala Gly Thr Gly Gly
145                 150                 155                 160

Ala Gly Ala Cys Cys Ala Cys Cys Ala Cys Cys Cys Thr Cys
                165                 170                 175
```

```
Cys Ala Ala Ala Cys Ala Ala Gly Cys Ala Ala Cys Ala Ala Cys
                180                 185                 190

Ala Ala Gly Thr Ala Cys Gly Cys Gly Cys Ala Gly Cys Ala
            195                 200                 205

Gly Cys Thr Ala Thr Cys Thr Gly Ala Gly Cys Cys Thr Gly Ala Cys
    210                 215                 220

Gly Cys Cys Thr Gly Ala Gly Cys Ala Gly Thr Gly Gly Ala Ala Gly
225                 230                 235                 240

Thr Cys Cys Cys Ala Cys Ala Gly Ala Ala Gly Cys Thr Ala Cys Ala
                245                 250                 255

Gly Cys Thr Gly Cys Cys Ala Gly Cys Ala Gly Thr Gly Cys Gly Cys Ala
        260                 265                 270

Thr Gly Ala Ala Gly Gly Ala Gly Cys Ala Cys Cys Gly Thr Gly
            275                 280                 285

Gly Ala Gly Ala Ala Gly Ala Cys Ala Gly Thr Gly Gly Cys Cys Cys
    290                 295                 300

Cys Thr Ala Cys Ala Gly Ala Ala Thr Gly Thr Thr Cys Ala Thr Ala
305                 310                 315                 320

Gly
```

<210> SEQ ID NO 182
<211> LENGTH: 120
<212> TYPE: PRT
<213> ORGANISM: Artificial Sequence
<220> FEATURE:
<223> OTHER INFORMATION: Variable region

<400> SEQUENCE: 182

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Phe Val
        35                  40                  45

Ala Ala Ile Arg Asn Asp Gly Ser Trp Thr Tyr Gly Ala Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Ser Ser Gly Gly Ser Ile Gly Ala Trp Gly Gln
            100                 105                 110

Gly Thr Leu Val Thr Val Ser Ser
        115                 120
```

<210> SEQ ID NO 183
<211> LENGTH: 327
<212> TYPE: PRT
<213> ORGANISM: Artificial Sequence
<220> FEATURE:
<223> OTHER INFORMATION: Heavy chain constant region

<400> SEQUENCE: 183

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 184
<211> LENGTH: 105
<212> TYPE: PRT
<213> ORGANISM: Artificial Sequence
<220> FEATURE:
<223> OTHER INFORMATION: Variable region

<400> SEQUENCE: 184

Ser Tyr Glu Leu Thr Gln Pro Pro Ser Val Ser Val Ser Pro Gly Gln
 1               5                  10                  15

Thr Ala Arg Ile Thr Cys Ser Gly Gly Ser Gly Arg Tyr Tyr Tyr Gly
             20                  25                  30

Trp Tyr Gln Gln Lys Pro Gly Gln Ala Pro Val Thr Val Ile Tyr Ser
             35                  40                  45

Ser Thr His Arg Pro Ser Gly Ile Pro Glu Arg Phe Ser Gly Ser Asn
 50                  55                  60
```

```
Ser Gly Ser Thr Thr Thr Leu Thr Ile Ser Gly Val Gln Ala Glu Asp
 65                  70                  75                  80

Glu Ala Asp Tyr Tyr Cys Gly Thr Ala Asp Ser Ser Tyr Val Phe
                 85                  90                  95

Gly Gly Gly Thr Lys Leu Thr Val Leu
            100                 105

<210> SEQ ID NO 185
<211> LENGTH: 106
<212> TYPE: PRT
<213> ORGANISM: Artificial Sequence
<220> FEATURE:
<223> OTHER INFORMATION: Light chain constant region

<400> SEQUENCE: 185

Gly Gln Pro Lys Ala Ala Pro Ser Val Thr Leu Phe Pro Pro Ser Ser
  1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 186
<211> LENGTH: 120
<212> TYPE: PRT
<213> ORGANISM: Artificial Sequence
<220> FEATURE:
<223> OTHER INFORMATION: Variable region

<400> SEQUENCE: 186

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Gly Met Gly Trp Val Arg Gln Ala Pro Gly Lys Gly Leu Glu Phe Val
             35                  40                  45

Ala Ala Ile Arg Asn Asp Gly Ser Trp Thr Gly Tyr Gly Ala Ala Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Thr Thr Gly Ser Arg Gly Gly Ser Ile Asp Ala Trp Gly Gln
            100                 105                 110

Gly Thr Leu Val Thr Val Ser Ser
            115                 120

<210> SEQ ID NO 187
<211> LENGTH: 104
<212> TYPE: PRT
<213> ORGANISM: Artificial Sequence
```

-continued

<220> FEATURE:
<223> OTHER INFORMATION: Variable region

<400> SEQUENCE: 187

Ser Tyr Glu Leu Thr Gln Pro Pro Ser Val Ser Val Ser Pro Gly Gln
1               5                   10                  15

Thr Ala Arg Ile Thr Cys Ser Gly Gly Arg Tyr Tyr Tyr Gly Trp
            20                  25                  30

Tyr Gln Gln Lys Pro Gly Gln Ala Pro Val Thr Val Ile Tyr Ala Asn
        35                  40                  45

Asp Lys Arg Pro Ser Gly Ile Pro Glu Arg Phe Ser Gly Ser Asn Ser
    50                  55                  60

Gly Ser Thr Thr Thr Leu Thr Ile Ser Gly Val Gln Ala Glu Asp Glu
65                  70                  75                  80

Ala Asp Tyr Tyr Cys Ser Ala Glu Thr Ser Ser Tyr Val Phe Gly
                85                  90                  95

Gly Gly Thr Lys Leu Thr Val Leu
            100

<210> SEQ ID NO 188
<211> LENGTH: 120
<212> TYPE: PRT
<213> ORGANISM: Artificial Sequence
<220> FEATURE:
<223> OTHER INFORMATION: Variable region

<400> SEQUENCE: 188

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Phe Val
        35                  40                  45

Ala Ala Ile Arg Asn Asp Gly Ser Trp Thr Gly Tyr Gly Ala Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Ser Ser Gly Ser Ile Gly Ala Trp Gly Gln
            100                 105                 110

Gly Thr Leu Val Thr Val Ser Ser
        115                 120

<210> SEQ ID NO 189
<211> LENGTH: 105
<212> TYPE: PRT
<213> ORGANISM: Artificial Sequence
<220> FEATURE:
<223> OTHER INFORMATION: Variable region

<400> SEQUENCE: 189

Ser Tyr Glu Leu Thr Gln Pro Pro Ser Val Ser Val Ser Pro Gly Gln
1               5                   10                  15

Thr Ala Arg Ile Thr Cys Ser Gly Gly Asn Arg Asn Tyr Tyr Tyr Gly
            20                  25                  30

Trp Tyr Gln Gln Lys Pro Gly Gln Ala Pro Val Thr Val Ile Tyr Ala
        35                  40                  45

```
Asn Asp Lys Arg Pro Ser Gly Ile Pro Glu Arg Phe Ser Gly Ser Asn
        50                  55                  60

Ser Gly Ser Thr Thr Thr Leu Thr Ile Ser Gly Val Gln Ala Glu Asp
 65                  70                  75                  80

Glu Ala Asp Tyr Tyr Cys Gly Thr Ala Asp Thr Gly Lys Tyr Val Phe
                85                  90                  95

Gly Gly Gly Thr Lys Leu Thr Val Leu
            100                 105
```

<210> SEQ ID NO 190
<211> LENGTH: 120
<212> TYPE: PRT
<213> ORGANISM: Artificial Sequence
<220> FEATURE:
<223> OTHER INFORMATION: Variable region

<400> SEQUENCE: 190

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Phe Val
        35                  40                  45

Ala Ala Ile Arg Asn Asp Gly Ser Trp Thr Gly Tyr Gly Ala Ala Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Tyr Thr Gly Ser Ser Gly Gly Ser Ile Gly Ala Trp Gly Gln
            100                 105                 110

Gly Thr Leu Val Thr Val Ser Ser
        115                 120
```

<210> SEQ ID NO 191
<211> LENGTH: 104
<212> TYPE: PRT
<213> ORGANISM: Artificial Sequence
<220> FEATURE:
<223> OTHER INFORMATION: Variable region

<400> SEQUENCE: 191

```
Ser Tyr Glu Leu Thr Gln Pro Pro Ser Val Ser Val Ser Pro Gly Gln
 1               5                   10                  15

Thr Ala Arg Ile Thr Cys Ser Gly Gly Arg Tyr Tyr Tyr Gly Trp
            20                  25                  30

Tyr Gln Gln Lys Pro Gly Gln Ala Pro Val Thr Val Ile Tyr Ala Asn
        35                  40                  45

Asp Lys Arg Pro Ser Gly Ile Pro Glu Arg Phe Ser Gly Ser Asn Ser
    50                  55                  60

Gly Ser Thr Thr Thr Leu Thr Ile Ser Gly Val Gln Ala Glu Asp Glu
 65                  70                  75                  80

Ala Asp Tyr Tyr Cys Gly Ser Ala Glu Thr Ser Ser Tyr Val Phe Gly
                85                  90                  95

Gly Gly Thr Lys Leu Thr Val Leu
            100
```

<210> SEQ ID NO 192

<211> LENGTH: 120
<212> TYPE: PRT
<213> ORGANISM: Artificial Sequence
<220> FEATURE:
<223> OTHER INFORMATION: Variable region

<400> SEQUENCE: 192

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Phe Val
        35                  40                  45

Ala Ala Ile Arg Asn Asp Gly Ser Trp Thr Gly Tyr Gly Ala Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Ser Ser Gly Ser Ile Gly Ala Trp Gly Gln
            100                 105                 110

Gly Thr Leu Val Thr Val Ser Ser
        115                 120

<210> SEQ ID NO 193
<211> LENGTH: 105
<212> TYPE: PRT
<213> ORGANISM: Artificial Sequence
<220> FEATURE:
<223> OTHER INFORMATION: Variable region

<400> SEQUENCE: 193

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Arg Tyr Tyr Tyr Gly
            20                  25                  30

Trp Tyr Gln Gln Lys Pro Gly Gln Ala Pro Val Thr Val Ile Tyr Ser
        35                  40                  45

Ser Thr His Arg Pro Ser Gly Ile Pro Glu Arg Phe Ser Gly Ser Asn
    50                  55                  60

Ser Gly Ser Thr Thr Thr Leu Thr Ile Ser Gly Val Gln Ala Glu Asp
65                  70                  75                  80

Glu Ala Asp Tyr Tyr Cys Gly Thr Ala Asp Ser Ser Ser Tyr Val Phe
                85                  90                  95

Gly Gly Gly Thr Lys Leu Thr Val Leu
            100                 105

<210> SEQ ID NO 194
<211> LENGTH: 120
<212> TYPE: PRT
<213> ORGANISM: Artificial Sequence
<220> FEATURE:
<223> OTHER INFORMATION: Variable region

<400> SEQUENCE: 194

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

```
Ala Met Gly Trp Val Arg Gln Ala Pro Gly Lys Gly Leu Glu Phe Val
            35                  40                  45

Ala Ala Ile Arg Asn Asp Gly Ser Trp Thr Gly Tyr Gly Ala Ala Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Thr Gly Ser Ser Gly Gly Ser Ile Gly Ala Trp Gly Gln
            100                 105                 110

Gly Thr Leu Val Thr Val Ser Ser
            115                 120

<210> SEQ ID NO 195
<211> LENGTH: 105
<212> TYPE: PRT
<213> ORGANISM: Artificial Sequence
<220> FEATURE:
<223> OTHER INFORMATION: Variable region

<400> SEQUENCE: 195

Ser Tyr Glu Leu Thr Gln Pro Pro Ser Val Ser Val Ser Pro Gly Gln
 1               5                  10                  15

Thr Ala Arg Ile Thr Cys Ser Gly Gly Ser Gly Arg Tyr Tyr Tyr Gly
            20                  25                  30

Trp Tyr Gln Gln Lys Pro Gly Gln Ala Pro Val Thr Val Ile Tyr Ser
        35                  40                  45

Ser Thr His Arg Pro Ser Gly Ile Pro Glu Arg Phe Ser Gly Ser Asn
 50                  55                  60

Ser Gly Ser Thr Thr Thr Leu Thr Ile Ser Gly Val Gln Ala Glu Asp
 65                  70                  75                  80

Glu Ala Asp Tyr Tyr Cys Gly Thr Ala Asp Ser Ser Ser Tyr Val Phe
                 85                  90                  95

Gly Gly Gly Thr Lys Leu Thr Val Leu
            100                 105

<210> SEQ ID NO 196
<211> LENGTH: 447
<212> TYPE: PRT
<213> ORGANISM: Artificial Sequence
<220> FEATURE:
<223> OTHER INFORMATION: Heavy chain

<400> SEQUENCE: 196

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Phe Val
            35                  40                  45

Ala Ala Ile Arg Asn Asp Gly Ser Trp Thr Gly Tyr Gly Ala Ala Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Thr Gly Ser Ser Gly Gly Ser Ile Gly Ala Trp Gly Gln
            100                 105                 110
```

```
Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 197
<211> LENGTH: 211
<212> TYPE: PRT
<213> ORGANISM: Artificial Sequence
<220> FEATURE:
<223> OTHER INFORMATION: Light chain

<400> SEQUENCE: 197

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Arg Tyr Tyr Tyr Gly
            20                  25                  30
```

```
Trp Tyr Gln Gln Lys Pro Gly Gln Ala Pro Val Thr Val Ile Tyr Ser
            35                  40                  45

Ser Thr His Arg Pro Ser Gly Ile Pro Glu Arg Phe Ser Gly Ser Asn
        50                  55                  60

Ser Gly Ser Thr Thr Thr Leu Thr Ile Ser Gly Val Gln Ala Glu Asp
65                      70                  75                  80

Glu Ala Asp Tyr Tyr Cys Gly Thr Ala Asp Ser Ser Ser Tyr Val Phe
                85                  90                  95

Gly Gly Gly Thr Lys Leu Thr Val Leu Gly Gln Pro Lys Ala Ala Pro
                100                 105                 110

Ser Val Thr Leu Phe Pro Pro Ser Ser Glu Glu Leu Gln Ala Asn Lys
            115                 120                 125

Ala Thr Leu Val Cys Leu Ile Ser Asp Phe Tyr Pro Gly Ala Val Thr
            130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
                180                 185                 190

Gln Val Thr His Glu Gly Ser Thr Val Glu Lys Thr Val Ala Pro Thr
                195                 200                 205

Glu Cys Ser
        210
```